US012692297B2

(12) United States Patent
Stauss et al.

(10) Patent No.: US 12,692,297 B2
(45) Date of Patent: Jul. 28, 2026

(54) ENGINEERED REGULATORY T CELL

(71) Applicant: UCL Business Ltd, London (GB)

(72) Inventors: Hans Stauss, London (GB); Sharyn Thomas, London (GB); Olivier Preham, London (GB)

(73) Assignee: UCL Business Ltd, London (GB)

( * ) Notice: Subject to any disclaimer, the term of this patent is extended or adjusted under 35 U.S.C. 154(b) by 1043 days.

(21) Appl. No.: 17/771,465

(22) PCT Filed: Oct. 22, 2020

(86) PCT No.: PCT/GB2020/052657
§ 371 (c)(1),
(2) Date: Apr. 23, 2022

(87) PCT Pub. No.: WO2021/079120
PCT Pub. Date: Apr. 29, 2021

(65) Prior Publication Data
US 2022/0363733 A1     Nov. 17, 2022

(30) Foreign Application Priority Data

Oct. 23, 2019     (GB) ..................................... 1915359

(51) Int. Cl.
| | |
|---|---|
| *C12N 5/0783* | (2010.01) |
| *A61K 40/11* | (2025.01) |
| *A61K 40/22* | (2025.01) |
| *A61K 40/32* | (2025.01) |
| *A61K 40/41* | (2025.01) |
| *C07K 14/705* | (2006.01) |
| *C12N 15/86* | (2006.01) |

(52) U.S. Cl.
CPC .......... *C07K 14/7051* (2013.01); *A61K 40/11* (2025.01); *A61K 40/22* (2025.01); *A61K 40/32* (2025.01); *A61K 40/416* (2025.01); *C12N 5/0637* (2013.01); *C12N 15/86* (2013.01)

(58) Field of Classification Search
None
See application file for complete search history.

(56) References Cited

U.S. PATENT DOCUMENTS

| | | | |
|---|---|---|---|
| 7,131,958 B2 | 11/2006 | Deverre | |
| 7,147,626 B2 | 12/2006 | Goodman et al. | |
| 12,227,756 B2 * | 2/2025 | Stauss .............. | C07K 14/70539 |
| 2014/0004133 A1 | 1/2014 | Bykovskaia et al. | |

| | | | |
|---|---|---|---|
| 2016/0194605 A1 | 7/2016 | Scott et al. | |
| 2019/0203174 A1 | 7/2019 | Scott et al. | |
| 2019/0225692 A1* | 7/2019 | Sissons ................. | A61K 39/12 |

FOREIGN PATENT DOCUMENTS

| | | |
|---|---|---|
| WO | WO-2009050283 A1 | 4/2009 |
| WO | WO-2014145970 A1 | 9/2014 |
| WO | WO-2014183056 A1 | 11/2014 |
| WO | WO-2016133779 A1 | 8/2016 |
| WO | 2016174461 A1 | 11/2016 |
| WO | WO-2017062035 A1 | 4/2017 |
| WO | 2019/202322 A1 | 10/2019 |
| WO | 2019202323 A1 | 10/2019 |
| WO | 2021079122 A1 | 4/2021 |

OTHER PUBLICATIONS

Thesis submitted in partial fulfilment of the requirements of Edinburgh Napier University, for the award of Master by Research authored by Victoria Riddell, published Jan. 2018, pp. 1-82. (Year: 2018).*
PDB 306F_H TCR beta-1 Chain C Region, pp. 1-4, Aug. 11, 2017. (Year: 2017).*
PDB 306F_G TCR alpha Chain C Region, pp. 1-3, Aug. 11, 2017. (Year: 2017).*
Kuball et al. (Blood.2007;109:2331-2338). (Year: 2007).*
Kouichi Ito (National Institute of Neurological Disorders and Stroke grant No. 5R03NS061375-02, pp. 1-5, 2009). (Year: 2009).*
"NIH reporter database query," Google Gemini AI, p. 1, published Oct. 14, 2025. (Year: 2025).*
Maria Dall'Era, et al., "Adoptive Treg Cell Therapy in a Patient With Systemic Lupus Erythematosus", Arthritis & Rheumatology, 2019, pp. 431-440, vol. 71, No. 3.
Camelia Frantz, et al., "Regulatory T Cells in Systemic Sclerosis", Frontiers in Immunology, 2018, p. 2356, vol. 9.
Martha S. Jordan, et al., "Thymic Selection of CD4+CD25+ Regulatory T Cells Induced by an Agonist Self-Peptide", Nature Immunology, 2001, pp. 301-306, vol. 2, No. 4.
Kaitlyn A. Lagattuta, et al., "Repertoire Analyses Reveal T Cell Antigen Receptor Sequence Features that Influence T Cell Fate", Nature Immunology, 2022, pp. 446-457, vol. 23, No. 3.

(Continued)

*Primary Examiner* — Zachary S Skelding

(74) *Attorney, Agent, or Firm* — Grimes & Yvon LLP

(57) ABSTRACT

The present invention relates to an engineered regulatory T cell (Treg) comprising a T cell receptor (TCR) which is capable of specifically binding to a myelin basic protein (MBP) peptide or variant or fragment thereof when the peptide is presented by a major histocompatibility complex (MHC) molecule. The present invention further relates to methods for providing an engineered Treg and to methods and uses of said engineered Treg and vectors and kits of vectors encoding said Treg.

8 Claims, 26 Drawing Sheets

Specification includes a Sequence Listing.

(56)                    References Cited

OTHER PUBLICATIONS

Marco Romano, et al., "Past, Present, and Future of Regulatory T Cell Therapy in Transplantation and Autoimmunity", Frontiers in Immunology, 2019, p. 43, vol. 10.

Alexander Y. Rudensky, "Regulatory T Cells and Foxp3", Immunological Reviews, 2011, pp. 260-268, vol. 241, No. 1.

Masahiko Akamatsu, et al., "Conversion of Antigen-Specific Effector/Memory T Cells into Foxp3-Expressing Treg Cells by Inhibition of CDK8/19", Science Immunology, 2019, p. eaaw2707, vol. 4, No. 40.

Craig Hall, et al. "Requirements for Cell Surface Expression of the Human TCR/CD3 Complex in Non-T cells", International Immunology, 1991, pp. 359-368, vol. 3, No. 4.

Laura Jardine, et al., "Rapid Detection of Dendritic Cell and Monocyte Disorders Using CD4 as a Lineage Marker of the Human Peripheral Blood Antigen-Presenting Cell Compartment", Frontiers in Immunology, 2013, p. 495, vol. 4.

Zhiyuan Li, et al., "FOXP3+ Regulatory T Cells and their Functional Regulation", Cellular & Molecular Immunology, 2015, pp. 558-565, vol. 12, No. 4.

Jian Peng, et al., "Converting Antigen-Specific Diabetogenic CD4 and CD8 T Cells to TGF-Beta Producing Non-Pathogenic Regulatory Cells Following FoxP3 Transduction", Journal of Autoimmunity, 2007, pp. 188-200, vol. 28, No. 4.

Jenny McGovern, et al., "Forced Fox-P3 Expression Can Improve the Safety and Antigen-Specific Function of Engineered Regulatory T Cells", Journal of Autoimmunity, 2022, p. 102888, vol. 132.

Lucienne Chatenoud, "Natural and Induced T CD4+CD25+ FOXP3+ Regulatory T Cells", Methods in Molecular Biology, 2011, pp. 3-13, vol. 677.

Ming O. Li & Alexander Y. Rudensky, "T Cell Receptor Signalling in the Control of Regulatory T Cell Differentiation and Function", Nature Reviews Immunology, 2016, pp. 220-233, vol. 16, No. 4.

Rafal Pacholczyk & Joanna Kern, "The T-Cell Receptor Repertoire of Regulatory T Cells", Immunology, 2008, pp. 450-458, vol. 125, No. 4.

Victoria Riddell, Generating AG-specific human regulatory T-cell by TCR gene transfer for the treatment of rheumatoid arthritis, Thesis, Jan. 1, 2018, Edinburgh Napier University.

Kim Young Chan, et al., Engineered MBP-specific human Tregs ameliorate MOG-induced EAE through IL-2-triggered inhibition of effector T cells, Journal of Autoimmunity, May 30, 2018, vol. 92, pp. 77-86.

Jacqueline A. Quandt, et al., Unique clinical and pathological features in HLA-DRB1*0401-restricted MBP 111-129-specific humanized TCR transgenic mice, The Journal of Experimental Medicine, Jul. 19, 2004, vol. 200, No. 2, pp. 223-234.

Stefan Luth, et al., Ectopic expression of neural autoantigen in mouse liver suppresses experimental autoimmune neuroinflammation by inducing antigen-specific Tregs, Journal of Clinical Investigation, Sep. 18, 2008, vol. 118, No. 10, pp. 3403-3410.

Moa Fransson et al., CAR/FoxP3-engineered T regulatory cells target the CNS and suppress EAE upon intranasal delivery, Journal of Neuroinflammation, Jan. 1, 2012, vol. 9, No. 1, p. 112.

Lisa M. Bell, et al., "Cytoplasmic tail deletion of T cell receptor (TCR) B-chain results in its . . . ," Journal of Biological Chemistry, 1994, pp. 22758-22763, vol. 269, No. 36.

Roy A. Mariuzza, et al., "The structural basis of T-cell receptor (TCR) activation: an enduring enigma," Journal of Biological Chemistry, 2020, pp. 914-925, vol. 295, No. 4.

Ho-Keun Kwon, et al., "FoxP3 scanning mutagenesis reveals functional variegation and mild mutations with atypical autoimmune . . . ," PNAS, 2018, pp. E253-E262, vol. 115, No. 2.

Reiner K. W. Mailer, "Alternative splicing of FOXP3—virtue and vice," Frontiers in Immunology, 2018, art. 530, vol. 9.

Haruhiko Yagi, et al., "Crucial role of FOXP3 in the development and function of human CD25+CD4+ . . . ," International Immunology, 2004, pp. 1643-1656, vol. 16, No. 11.

Lin Chen, et al., "A humanized TCR retaining authentic specificity and affinity conferred potent anti-tumour cytotoxicity," Immunology, 2018, pp. 121-136, vol. 155.

E. Meinl & R. Hohlfeld, "Immunopathogenesis of multiple sclerosis: MBP and beyond," Clinical and Experimental Immunology, 2002, pp. 395-397, vol. 128, No. 3.

Peter Georgiev, et al., "Regulatory T cells: the many faces of Foxp3," Journal of Clinical Immunology, 2019, pp. 623-640, vol. 39, No. 7.

Andrea T. Nguyen, et al., "The pockets guide to HLA class I molecules," Biochemical Society Transactions, 2021, pp. 2319-2331, vol. 49.

Mindi R. Walker, et al., "Induction of FoxP3 and acquisition of T regulatory activity . . . ," Journal of Clinical Investigation, 2003, pp. 1437-1443, vol. 12, No. 9.

Patrick R. Adair, et al., "Human Tregs made antigen specific by gene modification: the power to treat autoimmunity and antidrug . . . ", Front. Immunol., 2017, vol. 8, p. 1117.

Stephen F. Altschul, et al., "Basic local alignment search tool", J. Mol. Biol., 1990, vol. 215, pp. 403-410.

Frederick M. Ausubel, et al., "Short protocols in molecular biology", 1999, 4th edition, chapter 18.

Frederick M. Ausubel, et al., "Short protocols in molecular biology", 1999, 4th edition, pp. 7-58 to 7-60.

Ute Bank, et al., "Inhibition of alanyl-aminopeptidase on CD4+ CD25+ regulatory T-cells enhances expression of FoxP3 . . . ", Int. J. Mol. Med., 2007, vol. 20, pp. 483-492.

John M. Coffin, et al., "Retroviruses", 1997, Cold Spring Harbour Laboratory Press Eds:, pp. 758-763.

Cyrille J. Cohen, et al., "Enhanced antitumor activity of T cells engineered to express T-cell receptors with a second . . . ", Cancer Res., 2007, vol. 67, pp. 3898-3903.

Nicholas A. J. Dawson, et al., "Engineered tolerance: tailoring development, function and antigen-specificity of regulatory T cells," Front. Immunol., 2017, vol. 8, p. 1460.

John Devereux, et al., "A comprehensive set of sequence analysis programs for the VAX", Nucl. Acid Res., 1984, vol. 12, pp. 387-395.

Michelle L. L., Donnelly, et al., "The 'cleavage' activities of foot-and-mouth disease virus 2A site-directed mutants and . . . ", J. Gen. Virol., 2001, vol. 82, pp. 1027-1041.

Geraldine Folch & Marie-Paule Lefranc, "The human T cell receptor beta variable (TRBV) genes", Exp. Clin. Immunogenet, 2000, vol. 17, pp. 42-54.

GenPept Accession No. 3O6 F_C, Chain C, and T-cell Receptor Alpha Chain Cregion, uploaded Sep. 7, 2011; Retrieved Feb. 13, 2023; URL: https://www.ncbi.nlm.nih.gov/protein . . . /306F_C.

GenPept Accession No. 3O6 F_D, Chain D, and T-cell Receiptor Beta-1 Chain C Region, uploaded Sep. 7, 2011. Retrieved Feb. 13, 2023; URL: https://www.ncbi.nlm.nih.gov/protein . . . /306F_D.

E. Hodges, et al., "Diagnostic role of tests for T cell receptor (TCR) genes", J. Clin. Pathol., 2003, vol. 56, pp. 1-11.

Jianbing Huang, et al., "Histone/protein deacetylase 11 targeting promotes Foxp3+ Treg function", Sci. Rep., 2017, vol. 7, p. 8626.

Jaebong Huh, et al., "Limited repertoire of HLA-DRB1*0401-restricted MBP111-129-specific T cells in HLA-DRB1*0401 Tg mice . . . ", J. Neuroimmunol., 2004, vol. 151, pp. 94-102.

Yong Chan Kim et al., "Engineered myelin basic protein (MBP)-specific human T regulatory cells ameliorate myelin oligodendrocyte . . . " J. Immunol., 2017, vol. 198, p. 15.

Ben F. Koop, et al., "The human T-cell receptor TCRAC/TCRDC (Cα/Cδ) region: organization, sequence and evolution of 97.6 kb of DNA", Genomics, 1994, vol. 19, pp. 478-493.

Jürgen Kuball, et al., "Facilitating matched pairing and expression of TCR chains introduced into human T cells", Blood, 2007, vol. 109, pp. 2331-2338.

Marie-Paule Lefranc, et al., "IMGT unique numbering for immunoglobulin and T cell receptor variable domains and Ig . . . ", Dev. Comp. Immunol., 2003, vol. 27, pp. 55-77.

Paul Lewis, et al., "Human immunodeficiency virus infection of cells arrested in the cell cycle", EMBO J., 1992, vol. 11, pp. 3053-3058.

(56)                        References Cited

OTHER PUBLICATIONS

Yunjie Lu, et al., "Rapamycin regulates iTreg function through CD39 and runx1 pathways", J. Immunol. Res., 2014, vol. 2014, p. 989434.
Divya J. Mekala & Terrence L. Geiger, "Immunotherapy of auto-immune encephalomyelitis with redirected CD4+ CD25+ T lym-phocytes", Blood, 2005, vol. 105, pp. 2090-2092.
Ydivya J. Mekala, et al., "IL-10-dependent infectious tolerance after the treatment of experimental allergic . . . ", Proc. Natl. Acad. Sci. USA, 2005, vol. 102, pp. 11817-11822.
MMDB, 306F: Crystal Structure of a Numan Autominnune Tor Ms2-3c8 bound to Mhc class liSelf-ligand Mbp/hla-dr4, 2011.09; Retrieved Feb. 13, 2023; URL: https://www.ncbi.nlm.nih . . . /306F.
Paolo A. Muraro, et al., "Immunodominance of a low-affinity major histocompatibility complex-binding myelin basic . . . ", J. Clin. Invest., 1997, vol. 100, pp. 339-349.
Carol Papworth, et al., "Highly efficient double-stranded site-directed mutagenesis with the Chameleon kit", Strategies Mol. Biol., 1996, vol. 7, pp. 38-40.
Jiangzhou Peng, et al., "The effect of foxp3-overexpressing Treg cells on non-small cell lung cancer cells", Mol. Med. Rep., 2018, vol. 17, pp. 5860-5868.
Victoria Riddell, "Generating ag-specific human regulatory T-cells by TCR gene transfer for the treatment of rheumatoid arthritis", (Thesis), 2019, Ediburgh Napier Univeristy.
Dominique Scaviner & Marie-Paule Lefranc, "The human T cell receptor alpha variable (TRAV) genes", Exp. Clin. Immunogenet., 2000, vol. 17, pp. 83-96.
Leigh A. Stephens, et al., "Curing CNS autoimmune disease with myelin-reactive Foxp3(+) Treg", Eur. J. Immunol., 2009, vol. 39, pp. 1108-1117.
V. K. Tuohy, et al., "Preemptive targeting of the epitope spreading cascade with genetically modified regulatory T cells induces Tr1 . . . ", FASEB J., 2001, vol. 15, p. A1212.
Graham P. Wright, et al., "Adoptive therapy with redirected primary regulatory T cells results in . . . ", Proc. Natl. Acad. Sci., 2009, vol. 106, pp. 19078-19083.

Yiyuan Yin, et al., "Structure of a TCR with high affinity for sef-antigen reveals basis for escape from negative selection", EMBO J., 2011, vol. 30, pp. 1137-1148.
Guang-Ju Zhao, et al., "Growth arrest-specific 6 enhances the suppressive function of CD4+CD25+ regulatory T cells . . . ", Mediators Inflamm., 2017, vol. 2017, p. 6848430.
Dun Zhou, et al., "High throughput analysis of TCR-β rearrange-ment and gene expression in single T cells", Lab. Invest., 2006, vol. 86, pp. 314-321.
Luming Zhou, et al., "Rare allele enrichment and detection by allele-specific PCR, competitive probe blocking, and melting analy-sis", BioTechniques, 2011, vol. 50, pp. 311-318.
Alla L. Zozulya & Heinz Wiendl, "The role of regulatory T cells in multiple sclerosis", Nat. Clin. Pract. Neurol., 2008, vol. 4, pp. 384-398.
Kailash Singh, et al., "Concomitant analysis of Helios and Neuroilin-1 as a marker to detect thymic derived regulatory T cells in . . . ", Sci. Rep., 2015, vol. 75, p. 7767.
UniProtKB Accession P02686-5, Myelin Basic Protein Human, uploaded Jul. 21, 1986; Retrieved Dec. 13, 2024; URL: https://www.uniprot.org/uniprotkb/P02686/entry.
Lee Rowen, et al., "The Complete 685-Kilobase DNA Sequence of the Human Beta T Cell Receptor Locus", Science, 1996, pp. 1755-1762, vol. 272, No. 5269.
CAS Registry No. 1637420-83-7, TCR αβ (receptor), anti-(human myelin basic protein) (synthetic human single-chain), uploaded Nov. 26, 2014.
Zenichiro Kato, et al., "Positioning of Autoimmune TCR-Ob.2F3 and . . . ", Proceedings of the National Academy Science of the USA, 2008, pp. 15523-15528, vol. 105, No. 40.
Zenichiro Kato, et al., "The Autoimmune TCR-Ob.2F3 Can Bind to MBP85-99/HLA-DR2 Having an Unconventional . . . ", Molecular Immunology, 2010, pp. 314-320, vol. 48, No. 1-3.
Database Geneseq Accession No. BBP99214, Human Myelin Basic Protein (MBP), SEQ2, uploaded Jan. 1, 2015, XP093218717.

* cited by examiner a

| Variable α | Con. α | P2A | Variable β | Con. β | T2A | tmCD19 |
|---|---|---|---|---|---|---|

(cloned into pMP71 vector)

| Variable β | Con. β | P2A | Variable α | Con. α | T2A | tmCD19 |
|---|---|---|---|---|---|---|

(cloned into pMP71 vector)

b

C d d e

A

B

A)

B)

SEQUENCE LISTING

```
<160> NUMBER OF SEQ ID NOS: 33

<210> SEQ ID NO 1
<211> LENGTH: 11
<212> TYPE: PRT
<213> ORGANISM: Artificial Sequence
<220> FEATURE:
<223> OTHER INFORMATION: T cell receptor (TCR) alpha chain
      complementarity determining region (CDR), CDR3alpha

<400> SEQUENCE: 1

Thr Val Tyr Gly Gly Ala Thr Asn Lys Leu Ile
1               5                   10
```

```
<210> SEQ ID NO 2
<211> LENGTH: 12
<212> TYPE: PRT
<213> ORGANISM: Artificial Sequence
<220> FEATURE:
<223> OTHER INFORMATION: TCR beta chain CDR, CDR3beta

<400> SEQUENCE: 2

Ser Ala Arg Gly Gly Ser Tyr Asn Ser Pro Leu His
1               5                   10

<210> SEQ ID NO 3
<211> LENGTH: 7
<212> TYPE: PRT
<213> ORGANISM: Artificial Sequence
<220> FEATURE:
<223> OTHER INFORMATION: TCR alpha chain CDR, CDR1alpha

<400> SEQUENCE: 3

Thr Ile Ser Gly Thr Asp Tyr
1               5

<210> SEQ ID NO 4
<211> LENGTH: 5
<212> TYPE: PRT
<213> ORGANISM: Artificial Sequence
<220> FEATURE:
<223> OTHER INFORMATION: TCR alpha chain CDR, CDR2alpha

<400> SEQUENCE: 4

Gly Leu Thr Ser Asn
1               5

<210> SEQ ID NO 5
<211> LENGTH: 6
<212> TYPE: PRT
<213> ORGANISM: Artificial Sequence
<220> FEATURE:
<223> OTHER INFORMATION: TCR beta chain CDR, CDR1beta

<400> SEQUENCE: 5

Asp Phe Gln Ala Thr Thr
1               5

<210> SEQ ID NO 6
<211> LENGTH: 7
<212> TYPE: PRT
<213> ORGANISM: Artificial Sequence
<220> FEATURE:
<223> OTHER INFORMATION: TCR beta chain CDR, CDR2beta

<400> SEQUENCE: 6

Ser Asn Glu Gly Ser Lys Ala
1               5

<210> SEQ ID NO 7
<211> LENGTH: 111
<212> TYPE: PRT
<213> ORGANISM: Artificial Sequence
<220> FEATURE:
<223> OTHER INFORMATION: illustrative TCR alpha chain variable region

<400> SEQUENCE: 7

Asp Ala Lys Thr Thr Gln Pro Asn Ser Met Glu Ser Asn Glu Glu Glu
1               5                   10                  15

Pro Val His Leu Pro Cys Asn His Ser Thr Ile Ser Gly Thr Asp Tyr
            20                  25                  30
```

-continued

Ile His Trp Tyr Arg Gln Leu Pro Ser Gln Gly Pro Glu Tyr Val Ile
        35                  40                  45

His Gly Leu Thr Ser Asn Val Asn Asn Arg Met Ala Ser Leu Ala Ile
    50                  55                  60

Ala Glu Asp Arg Lys Ser Ser Thr Leu Ile Leu His Arg Ala Thr Leu
65                  70                  75                  80

Arg Asp Ala Ala Val Tyr Tyr Cys Thr Val Tyr Gly Gly Ala Thr Asn
                85                  90                  95

Lys Leu Ile Phe Gly Thr Gly Thr Leu Leu Ala Val Gln Pro Asn
            100                 105                 110

<210> SEQ ID NO 8
<211> LENGTH: 116
<212> TYPE: PRT
<213> ORGANISM: Artificial Sequence
<220> FEATURE:
<223> OTHER INFORMATION: illustrative TCR beta chain variable region

<400> SEQUENCE: 8

Gly Ala Val Val Ser Gln His Pro Ser Trp Val Ile Cys Lys Ser Gly
1               5                   10                  15

Thr Ser Val Lys Ile Glu Cys Arg Ser Leu Asp Phe Gln Ala Thr Thr
                20                  25                  30

Met Phe Trp Tyr Arg Gln Phe Pro Lys Gln Ser Leu Met Leu Met Ala
        35                  40                  45

Thr Ser Asn Glu Gly Ser Lys Ala Thr Tyr Glu Gln Gly Val Glu Lys
    50                  55                  60

Asp Lys Phe Leu Ile Asn His Ala Ser Leu Thr Leu Ser Thr Leu Thr
65                  70                  75                  80

Val Thr Ser Ala His Pro Glu Asp Ser Ser Phe Tyr Ile Cys Ser Ala
                85                  90                  95

Arg Gly Gly Ser Tyr Asn Ser Pro Leu His Phe Gly Asn Gly Thr Arg
            100                 105                 110

Leu Thr Val Thr
        115

<210> SEQ ID NO 9
<211> LENGTH: 251
<212> TYPE: PRT
<213> ORGANISM: Artificial Sequence
<220> FEATURE:
<223> OTHER INFORMATION: illustrative TCR alpha chain

<400> SEQUENCE: 9

Asp Ala Lys Thr Thr Gln Pro Asn Ser Met Glu Ser Asn Glu Glu Glu
1               5                   10                  15

Pro Val His Leu Pro Cys Asn His Ser Thr Ile Ser Gly Thr Asp Tyr
                20                  25                  30

Ile His Trp Tyr Arg Gln Leu Pro Ser Gln Gly Pro Glu Tyr Val Ile
        35                  40                  45

His Gly Leu Thr Ser Asn Val Asn Asn Arg Met Ala Ser Leu Ala Ile
    50                  55                  60

Ala Glu Asp Arg Lys Ser Ser Thr Leu Ile Leu His Arg Ala Thr Leu
65                  70                  75                  80

Arg Asp Ala Ala Val Tyr Tyr Cys Thr Val Tyr Gly Gly Ala Thr Asn
                85                  90                  95

Lys Leu Ile Phe Gly Thr Gly Thr Leu Leu Ala Val Gln Pro Asn Ile

-continued

```
                100                 105                 110
Gln Asn Pro Asp Pro Ala Val Tyr Gln Leu Arg Asp Ser Lys Ser Ser
            115                 120                 125
Asp Lys Ser Val Cys Leu Phe Thr Asp Phe Asp Ser Gln Thr Asn Val
    130                 135                 140
Ser Gln Ser Lys Asp Ser Asp Val Tyr Ile Thr Asp Lys Thr Val Leu
145                 150                 155                 160
Asp Met Arg Ser Met Asp Phe Lys Ser Asn Ser Ala Val Ala Trp Ser
                165                 170                 175
Asn Lys Ser Asp Phe Ala Cys Ala Asn Ala Phe Asn Asn Ser Ile Ile
            180                 185                 190
Pro Glu Asp Thr Phe Phe Pro Ser Pro Glu Ser Ser Cys Asp Val Lys
            195                 200                 205
Leu Val Glu Lys Ser Phe Glu Thr Asp Thr Asn Leu Asn Phe Gln Asn
        210                 215                 220
Leu Ser Val Ile Gly Phe Arg Ile Leu Leu Leu Lys Val Ala Gly Phe
225                 230                 235                 240
Asn Leu Leu Met Thr Leu Arg Leu Trp Ser Ser
                245                 250
```

<210> SEQ ID NO 10
<211> LENGTH: 295
<212> TYPE: PRT
<213> ORGANISM: Artificial Sequence
<220> FEATURE:
<223> OTHER INFORMATION: illustrative TCR beta chain

<400> SEQUENCE: 10

```
Gly Ala Val Val Ser Gln His Pro Ser Trp Val Ile Cys Lys Ser Gly
1               5                   10                  15
Thr Ser Val Lys Ile Glu Cys Arg Ser Leu Asp Phe Gln Ala Thr Thr
            20                  25                  30
Met Phe Trp Tyr Arg Gln Phe Pro Lys Gln Ser Leu Met Leu Met Ala
            35                  40                  45
Thr Ser Asn Glu Gly Ser Lys Ala Thr Tyr Glu Gln Gly Val Glu Lys
    50                  55                  60
Asp Lys Phe Leu Ile Asn His Ala Ser Leu Thr Leu Ser Thr Leu Thr
65                  70                  75                  80
Val Thr Ser Ala His Pro Glu Asp Ser Ser Phe Tyr Ile Cys Ser Ala
                85                  90                  95
Arg Gly Gly Ser Tyr Asn Ser Pro Leu His Phe Gly Asn Gly Thr Arg
            100                 105                 110
Leu Thr Val Thr Glu Asp Leu Lys Asn Val Phe Pro Pro Glu Val Ala
            115                 120                 125
Val Phe Glu Pro Ser Glu Ala Glu Ile Ser His Thr Gln Lys Ala Thr
        130                 135                 140
Leu Val Cys Leu Ala Thr Gly Phe Tyr Pro Asp His Val Glu Leu Ser
145                 150                 155                 160
Trp Trp Val Asn Gly Lys Glu Val His Ser Gly Val Ser Thr Asp Pro
                165                 170                 175
Gln Pro Leu Lys Glu Gln Pro Ala Leu Asn Asp Ser Arg Tyr Cys Leu
            180                 185                 190
Ser Ser Arg Leu Arg Val Ser Ala Thr Phe Trp Gln Asn Pro Arg Asn
            195                 200                 205
His Phe Arg Cys Gln Val Gln Phe Tyr Gly Leu Ser Glu Asn Asp Glu
```

-continued

```
        210                 215                 220

Trp Thr Gln Asp Arg Ala Lys Pro Val Thr Gln Ile Val Ser Ala Glu
225                 230                 235                 240

Ala Trp Gly Arg Ala Asp Cys Gly Phe Thr Ser Glu Ser Tyr Gln Gln
                245                 250                 255

Gly Val Leu Ser Ala Thr Ile Leu Tyr Glu Ile Leu Leu Gly Lys Ala
                260                 265                 270

Thr Leu Tyr Ala Val Leu Val Ser Ala Leu Val Leu Met Ala Met Val
                275                 280                 285

Lys Arg Lys Asp Ser Arg Gly
                290                 295

<210> SEQ ID NO 11
<211> LENGTH: 304
<212> TYPE: PRT
<213> ORGANISM: Homo sapiens

<400> SEQUENCE: 11

Met Gly Asn His Ala Gly Lys Arg Glu Leu Asn Ala Glu Lys Ala Ser
1                 5                  10                 15

Thr Asn Ser Glu Thr Asn Arg Gly Glu Ser Glu Lys Lys Arg Asn Leu
                20                 25                 30

Gly Glu Leu Ser Arg Thr Thr Ser Glu Asp Asn Glu Val Phe Gly Glu
                35                 40                 45

Ala Asp Ala Asn Gln Asn Asn Gly Thr Ser Ser Gln Asp Thr Ala Val
                50                 55                 60

Thr Asp Ser Lys Arg Thr Ala Asp Pro Lys Asn Ala Trp Gln Asp Ala
65                 70                 75                 80

His Pro Ala Asp Pro Gly Ser Arg Pro His Leu Ile Arg Leu Phe Ser
                85                 90                 95

Arg Asp Ala Pro Gly Arg Glu Asp Asn Thr Phe Lys Asp Arg Pro Ser
                100                105                110

Glu Ser Asp Glu Leu Gln Thr Ile Gln Glu Asp Ser Ala Ala Thr Ser
                115                120                125

Glu Ser Leu Asp Val Met Ala Ser Gln Lys Arg Pro Ser Gln Arg His
                130                135                140

Gly Ser Lys Tyr Leu Ala Thr Ala Ser Thr Met Asp His Ala Arg His
145                150                155                160

Gly Phe Leu Pro Arg His Arg Asp Thr Gly Ile Leu Asp Ser Ile Gly
                165                170                175

Arg Phe Phe Gly Gly Asp Arg Gly Ala Pro Lys Arg Gly Ser Gly Lys
                180                185                190

Asp Ser His His Pro Ala Arg Thr Ala His Tyr Gly Ser Leu Pro Gln
                195                200                205

Lys Ser His Gly Arg Thr Gln Asp Glu Asn Pro Val Val His Phe Phe
                210                215                220

Lys Asn Ile Val Thr Pro Arg Thr Pro Pro Pro Ser Gln Gly Lys Gly
225                230                235                240

Arg Gly Leu Ser Leu Ser Arg Phe Ser Trp Gly Ala Glu Gly Gln Arg
                245                250                255

Pro Gly Phe Gly Tyr Gly Gly Arg Ala Ser Asp Tyr Lys Ser Ala His
                260                265                270

Lys Gly Phe Lys Gly Val Asp Ala Gln Gly Thr Leu Ser Lys Ile Phe
                275                280                285
```

```
Lys Leu Gly Gly Arg Asp Ser Arg Ser Gly Ser Pro Met Ala Arg Arg
   290                 295                 300

<210> SEQ ID NO 12
<211> LENGTH: 19
<212> TYPE: PRT
<213> ORGANISM: Homo sapiens

<400> SEQUENCE: 12

Leu Ser Arg Phe Ser Trp Gly Ala Glu Gly Gln Arg Pro Gly Phe Gly
1               5                   10                  15

Tyr Gly Gly

<210> SEQ ID NO 13
<211> LENGTH: 171
<212> TYPE: PRT
<213> ORGANISM: Homo sapiens

<400> SEQUENCE: 13

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Asp Ser His His Pro
    50                  55                  60

Ala Arg Thr Ala His Tyr Gly Ser Leu Pro Gln Lys Ser His Gly Arg
65                  70                  75                  80

Thr Gln Asp Glu Asn Pro Val Val His Phe Phe Lys Asn Ile Val Thr
                85                  90                  95

Pro Arg Thr Pro Pro Pro Ser Gln Gly Lys Gly Arg Gly Leu Ser Leu
            100                 105                 110

Ser Arg Phe Ser Trp Gly Ala Glu Gly Gln Arg Pro Gly Phe Gly Tyr
            115                 120                 125

Gly Gly Arg Ala Ser Asp Tyr Lys Ser Ala His Lys Gly Phe Lys Gly
    130                 135                 140

Val Asp Ala Gln Gly Thr Leu Ser Lys Ile Phe Lys Leu Gly Gly Arg
145                 150                 155                 160

Asp Ser Arg Ser Gly Ser Pro Met Ala Arg Arg
                165                 170

<210> SEQ ID NO 14
<211> LENGTH: 333
<212> TYPE: DNA
<213> ORGANISM: Artificial Sequence
<220> FEATURE:
<223> OTHER INFORMATION: sequence encoding TCR alpha chain variable
      region

<400> SEQUENCE: 14
gacgccaaga ccacacagcc caacagcatg gaaagcaacg aagaggaacc cgtgcatctg      60
ccctgcaacc acagcacaat cagcggcacc gactacatcc actggtacag acagctgccc     120
agccagggac ctgagtatgt gatccacggc ctgaccagca acgtgaacaa cagaatggcc     180
agcctggcta tcgccgagga cagaaagagc agcaccctga tcctgcacag agccacactg     240
agagatgccg ccgtgtacta ctgcaccgtg tatggcggag ccaccaacaa gctgatcttc     300
ggcactggaa cactgctggc cgtgcagccc aat                                 333
```

<210> SEQ ID NO 15
<211> LENGTH: 348
<212> TYPE: DNA
<213> ORGANISM: Artificial Sequence
<220> FEATURE:
<223> OTHER INFORMATION: sequence encoding TCR beta chain variable
      region

<400> SEQUENCE: 15
ggagctgtgg tgtctcagca cccctcttgg gtcatctgca agagcggcac cagcgtgaag        60
atcgagtgca gaagcctgga cttccaggcc accaccatgt tttggtacag gcagttcccc       120
aagcagagcc tgatgctgat ggccacctct aacgagggca gcaaggccac atatgagcag       180
ggcgtcgaga aggacaagtt cctgatcaac cacgccagcc tgacactgag cacactgacc       240
gtgacaagcg cccatcctga ggactccagc ttctacatct gtagcgccag aggcggcagc       300
tacaacagcc ctctgcactt tggcaacggc accagactga cagtgacc                    348

<210> SEQ ID NO 16
<211> LENGTH: 753
<212> TYPE: DNA
<213> ORGANISM: Artificial Sequence
<220> FEATURE:
<223> OTHER INFORMATION: sequence encoding TCR alpha chain

<400> SEQUENCE: 16
gatgctaaga ccacacagcc aaattcaatg gagagtaacg aagaagagcc tgttcacttg        60
ccttgtaacc actccacaat cagtggaact gattacatac attggtatcg acagcttccc       120
tcccagggtc cagagtacgt gattcatggt cttacaagca atgtgaacaa cagaatggcc       180
tctctggcaa tcgctgaaga cagaaagtcc agtaccttga tcctgcaccg tgctaccttg       240
agagatgctg ctgtgtacta ctgcaccgtg tatggcggag ccaccaacaa gctgatcttc       300
ggcactggaa cactgctggc cgtgcagccc aatatccaga ccctgacccc tgccgtgtac       360
cagctgagag actctaaatc cagtgacaag tctgtctgcc tattcaccga ttttgattct       420
caaacaaatg tgtcacaaag taaggattct gatgtgtata tcacagacaa aactgtgcta       480
gacatgaggt ctatggactt caagagcaac agtgctgtgg cctggagcaa caaatctgac       540
tttgcatgtg caaacgcctt caacaacagc attattccag aagacacctt cttccccagc       600
ccagaaagtt cctgtgatgt caagctggtc gagaaaagct ttgaaacaga tacgaaccta       660
aactttcaaa acctgtcagt gattgggttc cgaatcctcc tcctgaaagt ggccgggttt       720
aatctgctca tgacgctgcg gctgtggtcc agc                                    753

<210> SEQ ID NO 17
<211> LENGTH: 885
<212> TYPE: DNA
<213> ORGANISM: Artificial Sequence
<220> FEATURE:
<223> OTHER INFORMATION: sequence encoding TCR beta chain

<400> SEQUENCE: 17
ggtgctgtcg tctctcaaca tccgagctgg gttatctgta agagtggaac ctctgtgaag        60
atcgagtgcc gttccctgga ctttcaggcc acaactatgt tttggtatcg tcagttcccg       120
aaacagagtc tcatgctgat ggcaacttcc aatgagggct ccaaggccac atacgagcaa       180
ggcgtcgaga aggacaagtt tctcatcaac catgcaagcc tgaccttgtc cactctgaca       240
gtgaccagtg cccatcctga agacagcagc ttctacatct gcagtgctag aggcggcagc       300

-continued

```
tacaacagcc ctctgcactt tggcaacggc accagactga cagtgaccga ggacctgaaa      360
aacgtgttcc cacccgaggt cgctgtgttt gagccatcag aagcagagat ctcccacacc      420
caaaaggcca cactggtgtg cctggccaca ggcttctacc ccgaccacgt ggagctgagc      480
tggtgggtga atgggaagga ggtgcacagt ggggtcagca cagacccgca gcccctcaag      540
gagcagcccg ccctcaatga ctccagatac tgcctgagca gccgcctgag ggtctcggcc      600
accttctggc agaacccccg caaccacttc cgctgtcaag tccagttcta cgggctctcg      660
gagaatgacg agtggaccca ggatagggcc aaacctgtca cccagatcgt cagcgccgag      720
gcctggggta gagcagactg tggcttcacc tccgagtctt accagcaagg ggtcctgtct      780
gccaccatcc tctatgagat cttgctaggg aaggccacct tgtatgccgt gctggtcagt      840
gccctcgtgc tgatggccat ggtcaagaga aaggattcca gaggc                     885
```

```
<210> SEQ ID NO 18
<211> LENGTH: 431
<212> TYPE: PRT
<213> ORGANISM: Homo sapiens

<400> SEQUENCE: 18

Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
            260                 265                 270
```

```
Ala Ser Ser Asp Lys Gly Ser Cys Cys Ile Val Ala Ala Gly Ser Gln
        275             280             285

Gly Pro Val Val Pro Ala Trp Ser Gly Pro Arg Glu Ala Pro Asp Ser
        290             295             300

Leu Phe Ala Val Arg Arg His Leu Trp Gly Ser His Gly Asn Ser Thr
305             310             315             320

Phe Pro Glu Phe Leu His Asn Met Asp Tyr Phe Lys Phe His Asn Met
            325             330             335

Arg Pro Pro Phe Thr Tyr Ala Thr Leu Ile Arg Trp Ala Ile Leu Glu
            340             345             350

Ala Pro Glu Lys Gln Arg Thr Leu Asn Glu Ile Tyr His Trp Phe Thr
        355             360             365

Arg Met Phe Ala Phe Phe Arg Asn His Pro Ala Thr Trp Lys Asn Ala
    370             375             380

Ile Arg His Asn Leu Ser Leu His Lys Cys Phe Val Arg Val Glu Ser
385             390             395             400

Glu Lys Gly Ala Val Trp Thr Val Asp Glu Leu Glu Phe Arg Lys Lys
                405             410             415

Arg Ser Gln Arg Pro Ser Arg Cys Ser Asn Pro Thr Pro Gly Pro
            420             425             430
```

<210> SEQ ID NO 19
<211> LENGTH: 441
<212> TYPE: PRT
<213> ORGANISM: Artificial Sequence
<220> FEATURE:
<223> OTHER INFORMATION: FOXP3 polypeptide sequence

<400> SEQUENCE: 19

```
Met Pro Asn Pro Arg Pro Gly Lys Pro Ser Ala Pro Ser Leu Ala Leu
1               5               10              15

Gly Pro Ser Pro Gly Ala Ser Pro Ser Trp Arg Ala Ala Pro Lys Ala
            20              25              30

Ser Asp Leu Leu Gly Ala Arg Gly Pro Gly Gly Thr Phe Gln Gly Arg
        35              40              45

Asp Leu Arg Gly Gly Ala His Ala Ser Ser Ser Leu Asn Pro Met
    50              55              60

Pro Pro Ser Gln Leu Gln Leu Pro Thr Leu Pro Leu Val Met Val Ala
65              70              75              80

Pro Ser Gly Ala Arg Leu Gly Pro Leu Pro His Leu Gln Ala Leu Leu
                85              90              95

Gln Asp Arg Pro His Phe Met His Gln Leu Ser Thr Val Asp Ala His
            100             105             110

Ala Arg Thr Pro Val Leu Gln Val His Pro Leu Glu Ser Pro Ala Met
        115             120             125

Ile Ser Leu Thr Pro Pro Thr Thr Ala Thr Gly Val Phe Ser Leu Lys
    130             135             140

Ala Arg Pro Gly Leu Pro Pro Gly Ile Asn Val Ala Ser Leu Glu Trp
145             150             155             160

Val Ser Arg Glu Pro Ala Leu Leu Cys Thr Phe Pro Asn Pro Ser Ala
                165             170             175

Pro Arg Lys Asp Ser Thr Leu Ser Ala Val Pro Gln Ser Ser Tyr Pro
            180             185             190

Leu Leu Ala Asn Gly Val Cys Lys Trp Pro Gly Cys Glu Lys Val Phe
        195             200             205
```

-continued

```
Glu Glu Pro Glu Asp Phe Leu Lys His Cys Gln Ala Asp His Leu Leu
    210              215             220

Asp Glu Lys Gly Arg Ala Gln Cys Leu Leu Gln Arg Glu Met Val Gln
225              230             235             240

Ser Leu Glu Gln Val Glu Glu Leu Ser Ala Met Gln Ala His Leu Ala
                245             250             255

Gly Lys Met Ala Leu Thr Lys Ala Ser Ser Val Ala Ser Ser Asp Lys
                260             265             270

Gly Ser Cys Cys Ile Val Ala Ala Gly Ser Gln Gly Pro Val Val Pro
                275             280             285

Ala Trp Ser Gly Pro Arg Glu Ala Pro Asp Ser Leu Phe Ala Val Arg
    290              295             300

Arg His Leu Trp Gly Ser His Gly Asn Ser Thr Phe Pro Glu Phe Leu
305              310             315             320

His Asn Met Asp Tyr Phe Lys Phe His Asn Met Arg Pro Pro Phe Thr
                325             330             335

Tyr Ala Thr Leu Ile Arg Trp Ala Ile Leu Glu Ala Pro Glu Lys Gln
                340             345             350

Arg Thr Leu Asn Glu Ile Tyr His Trp Phe Thr Arg Met Phe Ala Phe
                355             360             365

Phe Arg Asn His Pro Ala Thr Trp Lys Asn Ala Ile Arg His Asn Leu
    370              375             380

Ser Leu His Lys Cys Phe Val Arg Val Glu Ser Glu Lys Gly Ala Val
385              390             395             400

Trp Thr Val Asp Glu Leu Glu Phe Arg Lys Lys Arg Ser Gln Arg Pro
                405             410             415

Ser Arg Cys Ser Asn Pro Thr Pro Gly Pro Glu Gly Arg Gly Ser Leu
                420             425             430

Leu Thr Cys Gly Asp Val Glu Glu Asn
                435             440
```

```
<210> SEQ ID NO 20
<211> LENGTH: 1296
<212> TYPE: DNA
<213> ORGANISM: Homo sapiens

<400> SEQUENCE: 20
atgcccaacc ccaggcctgg caagccctcg gccccttcct tggcccttgg cccatcccca      60
ggagcctcgc ccagctggag ggctgcaccc aaagcctcag acctgctggg ggcccgggggc     120 ccagggggaa ccttccaggg ccgagatctt cgaggcgggg cccatgcctc ctcttcttcc     180
ttgaacccca tgccaccatc gcagctgcag ctgcccacac tgcccctagt catggtggca     240
ccctccgggg cacggctggg cccttgccc cacttacagg cactcctcca ggacaggcca     300
catttcatgc accagctctc aacggtggat gcccacgccc ggaccctgt gctgcaggtg     360 cacccctcg agagcccagc catgatcagc ctcacaccac ccaccaccgc cactgggtc     420 ttctccctca aggcccggcc tggcctccca cctgggatca acgtggccag cctggaatgg     480
gtgtccaggg agcggcact gctctgcacc ttcccaaatc ccagtgcacc caggaaggac     540
agcacccttt cggctgtgcc ccagagctcc tacccactgc tggcaaatgg tgtctgcaag     600
tggcccggat gtgagaaggt cttcgaagag ccagaggact tcctcaagca ctgccaggcg     660
gaccatcttc tggatgagaa gggcagggca caatgtctcc tccagagaga gatggtacag     720
tctctggagc agcagctggt gctggagaag gagaagctga gtgccatgca ggcccacctg     780
```

-continued

```
gctgggaaaa tggcactgac caaggcttca tctgtggcat catccgacaa gggctcctgc     840
tgcatcgtag ctgctggcag ccaaggccct gtcgtcccag cctggtctgg cccccgggag     900
gcccctgaca gcctgtttgc tgtccggagg cacctgtggg gtagccatgg aaacagcaca     960
ttcccagagt tcctccacaa catggactac ttcaagttcc acaacatgcg accccctttc    1020
acctacgcca cgctcatccg ctgggccatc ctggaggctc cagagaagca gcggacactc    1080
aatgagatct accactggtt cacacgcatg tttgccttct tcagaaacca tcctgccacc    1140
tggaagaacg ccatccgcca caacctgagt ctgcacaagt gctttgtgcg ggtggagagc    1200 gagaagggg ctgtgtggac cgtggatgag ctggagttcc gcaagaaacg gagccagagg    1260
cccagcaggt gttccaaccc tacacctggc ccctga                             1296
```

<210> SEQ ID NO 21
<211> LENGTH: 1352
<212> TYPE: DNA
<213> ORGANISM: Artificial Sequence
<220> FEATURE:
<223> OTHER INFORMATION: sequence encoding the FOXP3 polypeptide

<400> SEQUENCE: 21

```
gaattcgtcg acatgcccaa ccccagaccc ggcaagcctt ctgccccttc tctggccctg      60
ggaccatctc ctggcgcctc cccatcttgg agagccgccc ctaaagccag cgatctgctg     120
ggagctagag gccctggcgg cacattccag ggcagagatc tgagaggcgg agcccacgcc     180
tctagcagca gcctgaatcc catgcccct agccagctgc agctgcctac actgcctctc     240
gtgatggtgg cccctagcgg agctagactg ggccctctgc ctcatctgca ggctctgctg     300
caggaccggc cccactttat gcaccagctg agcaccgtgg acgcccacgc cagaacacct     360
gtgctgcagg tgcacccct ggaaagccct gccatgatca gcctgacccc tccaaccaca     420
gccaccggcg tgttcagcct gaaggccaga cctggactgc ccctggcat caatgtggcc     480 agcctggaat gggtgtcccg cgaacctgcc ctgctgtgca ccttccccaa tcctagcgcc     540
cccagaaagg acagcacact gtctgccgtg ccccagagca gctatcccct gctggctaac     600
ggcgtgtgca gtggcctgg ctgcgagaag gtgttcgagg aacccgagga cttcctgaag     660
cactgccagg ccgaccatct gctggacgag aaaggcagag cccagtgcct gctgcagcgc     720
gagatggtgc agtccctgga acagcagctg gtgctggaaa agaaaagct gagcgccatg     780 caggcccacc tggccggaaa gatggccctg acaaaagcca gcagcgtggc cagctccgac     840
aagggcagct gttgtatcgt ggccgctggc agccagggac ctgtggtgcc tgcttggagc     900
ggacctagag aggcccccga tagcctgttt gccgtgcgga cacctgtg gggcagccac     960 ggcaactcta ccttccccga gttcctgcac aacatggact acttcaagtt ccacaacatg    1020
aggcccccct tcacctacgc caccctgatc agatgggcca ttctggaagc ccccgagaag    1080
cagcggaccc tgaacgagat ctaccactgg tttacccgga tgttcgcctt cttccggaac    1140 cacccgcca cctggaagaa cgccatccgg cacaatctga gcctgcacaa gtgcttcgtg    1200
cgggtggaaa gcgagaaggg cgccgtgtgg acagtggacg agctggaatt cggaagaag    1260 cggtcccaga ggcccagccg tgtgtagcaat cctacacctg ccctgagggg cagaggaagt    1320
ctgctaacat gcggtgacgt cgaggagaat cc                                 1352
```

<210> SEQ ID NO 22
<211> LENGTH: 21
<212> TYPE: PRT

```
<213> ORGANISM: Artificial Sequence
<220> FEATURE:
<223> OTHER INFORMATION: leader sequence

<400> SEQUENCE: 22

Met Glu Lys Met Leu Glu Cys Ala Phe Ile Val Leu Trp Leu Gln Leu
1               5                   10                  15

Gly Trp Leu Ser Gly
            20

<210> SEQ ID NO 23
<211> LENGTH: 17
<212> TYPE: PRT
<213> ORGANISM: Artificial Sequence
<220> FEATURE:
<223> OTHER INFORMATION: leader sequence

<400> SEQUENCE: 23

Met Leu Cys Ser Leu Leu Ala Leu Leu Leu Gly Thr Phe Phe Gly Val
1               5                   10                  15

Arg

<210> SEQ ID NO 24
<211> LENGTH: 452
<212> TYPE: PRT
<213> ORGANISM: Artificial Sequence
<220> FEATURE:
<223> OTHER INFORMATION: FOXP3-2A polypeptide (FOXP3 polypeptide-2A
      self-cleaving peptide)

<400> SEQUENCE: 24

Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220
```

-continued

```
Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
                260                 265                 270

Ala Ser Ser Asp Lys Gly Ser Cys Cys Ile Val Ala Ala Gly Ser Gln
                275                 280                 285

Gly Pro Val Val Pro Ala Trp Ser Gly Pro Arg Glu Ala Pro Asp Ser
        290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
                340                 345                 350

Ala Pro Glu Lys Gln Arg Thr Leu Asn Glu Ile Tyr His Trp Phe Thr
                355                 360                 365

Arg Met Phe Ala Phe Phe Arg Asn His Pro Ala Thr Trp Lys Asn Ala
        370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg Ser Gln Arg Pro Ser Arg Cys Ser Asn Pro Thr Pro Gly Pro Gly
                420                 425                 430

Ala Thr Asn Phe Ser Leu Leu Lys Gln Ala Gly Asp Val Glu Glu Asn
        435                 440                 445

Pro Gly Pro Ser
    450
```

```
<210> SEQ ID NO 25
<211> LENGTH: 462
<212> TYPE: PRT
<213> ORGANISM: Artificial Sequence
<220> FEATURE:
<223> OTHER INFORMATION: FOXP3-2A polypeptide (FOXP3 polypeptide-2A
      self-cleaving peptide)

<400> SEQUENCE: 25
```

```
Met Pro Asn Pro Arg Pro Gly Lys Pro Ser Ala Pro Ser Leu Ala Leu
1                   5                   10                  15

Gly Pro Ser Pro Gly Ala Ser Pro Ser Trp Arg Ala Ala Pro Lys Ala
                20                  25                  30

Ser Asp Leu Leu Gly Ala Arg Gly Pro Gly Gly Thr Phe Gln Gly Arg
                35                  40                  45

Asp Leu Arg Gly Gly Ala His Ala Ser Ser Ser Leu Asn Pro Met
        50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
                100                 105                 110

Ala Arg Thr Pro Val Leu Gln Val His Pro Leu Glu Ser Pro Ala Met
```

```
                115                     120                     125

Ile Ser Leu Thr Pro Pro Thr Thr Ala Thr Gly Val Phe Ser Leu Lys
    130                     135                     140

Ala Arg Pro Gly Leu Pro Pro Gly Ile Asn Val Ala Ser Leu Glu Trp
145                     150                     155                     160

Val Ser Arg Glu Pro Ala Leu Leu Cys Thr Phe Pro Asn Pro Ser Ala
                165                     170                     175

Pro Arg Lys Asp Ser Thr Leu Ser Ala Val Pro Gln Ser Ser Tyr Pro
                180                     185                     190

Leu Leu Ala Asn Gly Val Cys Lys Trp Pro Gly Cys Glu Lys Val Phe
                195                     200                     205

Glu Glu Pro Glu Asp Phe Leu Lys His Cys Gln Ala Asp His Leu Leu
    210                     215                     220

Asp Glu Lys Gly Arg Ala Gln Cys Leu Leu Gln Arg Glu Met Val Gln
225                     230                     235                     240

Ser Leu Glu Gln Val Glu Glu Leu Ser Ala Met Gln Ala His Leu Ala
                245                     250                     255

Gly Lys Met Ala Leu Thr Lys Ala Ser Ser Val Ala Ser Ser Asp Lys
                260                     265                     270

Gly Ser Cys Cys Ile Val Ala Ala Gly Ser Gln Gly Pro Val Val Pro
                275                     280                     285

Ala Trp Ser Gly Pro Arg Glu Ala Pro Asp Ser Leu Phe Ala Val Arg
    290                     295                     300

Arg His Leu Trp Gly Ser His Gly Asn Ser Thr Phe Pro Glu Phe Leu
305                     310                     315                     320

His Asn Met Asp Tyr Phe Lys Phe His Asn Met Arg Pro Pro Phe Thr
                325                     330                     335

Tyr Ala Thr Leu Ile Arg Trp Ala Ile Leu Glu Ala Pro Glu Lys Gln
                340                     345                     350

Arg Thr Leu Asn Glu Ile Tyr His Trp Phe Thr Arg Met Phe Ala Phe
                355                     360                     365

Phe Arg Asn His Pro Ala Thr Trp Lys Asn Ala Ile Arg His Asn Leu
    370                     375                     380

Ser Leu His Lys Cys Phe Val Arg Val Glu Ser Glu Lys Gly Ala Val
385                     390                     395                     400

Trp Thr Val Asp Glu Leu Glu Phe Arg Lys Lys Arg Ser Gln Arg Pro
                405                     410                     415

Ser Arg Cys Ser Asn Pro Thr Pro Gly Pro Glu Gly Arg Gly Ser Leu
                420                     425                     430

Leu Thr Cys Gly Asp Val Glu Glu Asn Gly Ala Thr Asn Phe Ser Leu
                435                     440                     445

Leu Lys Gln Ala Gly Asp Val Glu Glu Asn Pro Gly Pro Ser
    450                     455                     460
```

```
<210> SEQ ID NO 26
<211> LENGTH: 140
<212> TYPE: PRT
<213> ORGANISM: Artificial Sequence
<220> FEATURE:
<223> OTHER INFORMATION: illustrative TCR alpha chain constant region

<400> SEQUENCE: 26

Ile Gln Asn Pro Asp Pro Ala Val Tyr Gln Leu Arg Asp Ser Lys Ser
1                   5                   10                  15

Ser Asp Lys Ser Val Cys Leu Phe Thr Asp Phe Asp Ser Gln Thr Asn
```

-continued

```
              20              25              30
Val Ser Gln Ser Lys Asp Ser Asp Val Tyr Ile Thr Asp Lys Thr Val
        35              40              45
Leu Asp Met Arg Ser Met Asp Phe Lys Ser Asn Ser Ala Val Ala Trp
    50              55              60
Ser Asn Lys Ser Asp Phe Ala Cys Ala Asn Ala Phe Asn Asn Ser Ile
65              70              75              80
Ile Pro Glu Asp Thr Phe Phe Pro Ser Pro Glu Ser Ser Cys Asp Val
            85              90              95
Lys Leu Val Glu Lys Ser Phe Glu Thr Asp Thr Asn Leu Asn Phe Gln
            100             105             110
Asn Leu Ser Val Ile Gly Phe Arg Ile Leu Leu Leu Lys Val Ala Gly
        115             120             125
Phe Asn Leu Leu Met Thr Leu Arg Leu Trp Ser Ser
    130             135             140
```

<210> SEQ ID NO 27
<211> LENGTH: 179
<212> TYPE: PRT
<213> ORGANISM: Artificial Sequence
<220> FEATURE:
<223> OTHER INFORMATION: illustrative TCR beta chain constant region

<400> SEQUENCE: 27

```
Glu Asp Leu Lys Asn Val Phe Pro Pro Glu Val Ala Val Phe Glu Pro
1               5               10              15
Ser Glu Ala Glu Ile Ser His Thr Gln Lys Ala Thr Leu Val Cys Leu
            20              25              30
Ala Thr Gly Phe Tyr Pro Asp His Val Glu Leu Ser Trp Trp Val Asn
        35              40              45
Gly Lys Glu Val His Ser Gly Val Ser Thr Asp Pro Gln Pro Leu Lys
    50              55              60
Glu Gln Pro Ala Leu Asn Asp Ser Arg Tyr Cys Leu Ser Ser Arg Leu
65              70              75              80
Arg Val Ser Ala Thr Phe Trp Gln Asn Pro Arg Asn His Phe Arg Cys
            85              90              95
Gln Val Gln Phe Tyr Gly Leu Ser Glu Asn Asp Glu Trp Thr Gln Asp
            100             105             110
Arg Ala Lys Pro Val Thr Gln Ile Val Ser Ala Glu Ala Trp Gly Arg
        115             120             125
Ala Asp Cys Gly Phe Thr Ser Glu Ser Tyr Gln Gln Gly Val Leu Ser
    130             135             140
Ala Thr Ile Leu Tyr Glu Ile Leu Leu Gly Lys Ala Thr Leu Tyr Ala
145             150             155             160
Val Leu Val Ser Ala Leu Val Leu Met Ala Met Val Lys Arg Lys Asp
            165             170             175
Ser Arg Gly
```

<210> SEQ ID NO 28
<211> LENGTH: 753
<212> TYPE: DNA
<213> ORGANISM: Artificial Sequence
<220> FEATURE:
<223> OTHER INFORMATION: illustrative TCR alpha chain

<400> SEQUENCE: 28
gacgccaaga ccacacagcc caacagcatg gaaagcaacg aagaggaacc cgtgcatctg      60

-continued

```
ccctgcaacc acagcacaat cagcggcacc gactacatcc actggtacag acagctgccc      120
agccagggac ctgagtatgt gatccacggc ctgaccagca cgtgaacaa cagaatggcc      180 agcctggcta tcgccgagga cagaaagagc agcaccctga tcctgcacag agccacactg      240
agagatgccg ccgtgtacta ctgcaccgtg tatggcggag ccaccaacaa gctgatcttc      300
ggcactggaa cactgctggc cgtgcagccc aatattcaga acccagatcc tgccgtgtac      360
cagctgagag acagcaagtc cagcgacaag agcgtgtgcc tgttcaccga cttcgacagc      420
cagaccaacg tgtcccagag caaggactcc gatgtgtata tcaccgacaa gaccgtgctg      480
gacatgcgga gcatggactt caagagcaac agcgccgtgg cctggtccaa caagagcgat      540
ttcgcctgcg ccaacgcctt caacaacagc attatccctg aggacacatt cttcccaagt      600
cctgagagca gctgcgacgt gaaactggtg gaaaagagct cgagacaga caccaacctg      660 aacttccaga acctgagcgt gatcggcttc agaatcctgc tgctgaaggt ggccggcttc      720
aacctgctga tgaccctgag actttggagc agc                                  753
```

```
<210> SEQ ID NO 29
<211> LENGTH: 753
<212> TYPE: DNA
<213> ORGANISM: Artificial Sequence
<220> FEATURE:
<223> OTHER INFORMATION: illustrative TCR alpha chain

<400> SEQUENCE: 29
```

```
gacgccaaga ccacacagcc caacagcatg gaaagcaacg aagaggaacc cgtgcatctg       60
ccctgcaacc acagcacaat cagcggcacc gactacatcc actggtatag acagctgccc      120
tctcagggcc ccgagtatgt gattcacggc ctgaccagca cgtgaacaa ccggatggcc      180 tctctggcca ttgccgagga cagaaagtcc agcacactga tcctgcaccg ggccacactg      240
agagatgccg ccgtgtatta ctgcaccgtg tacggcggag ccaccaacaa gctgatcttt      300
ggcacaggca cactgctggc cgtgcagccc aatattcaga accctgatcc agccgtgtac      360
cagctgagag acagcaagag cagcgacaag tctgtgtgtc tgttcaccga cttcgacagc      420
cagaccaacg tgtcccagag caaggactcc gatgtgtata tcaccgacaa gaccgtgctg      480
gacatgcgga gcatggactt caagagcaac agcgccgtgg cctggtccaa caagagcgat      540
tttgcctgcg ccaacgcctt caacaacagc attatccccg aggacacatt cttcccaagt      600
cctgagagca gctgcgacgt gaaactggtg gaaaagagct cgagacaga caccaacctg      660 aacttccaga acctgagcgt gatcggcttc agaatcctgc tgctgaaggt ggccggcttc      720
aacctgctga tgaccctgag actgtggtct agc                                  753
```

```
<210> SEQ ID NO 30
<211> LENGTH: 885
<212> TYPE: DNA
<213> ORGANISM: Artificial Sequence
<220> FEATURE:
<223> OTHER INFORMATION: illustrative TCR beta chain

<400> SEQUENCE: 30
```

```
ggagctgtgg tgtctcagca cccctcttgg gtcatctgca agagcggcac cagcgtgaag       60
atcgagtgca gaagcctgga cttccaggcc accaccatgt tttggtacag gcagttcccc      120
aagcagagcc tgatgctgat ggccaccctct aacgagggca gcaaggccac atatgagcag      180
ggcgtcgaga aggacaagtt cctgatcaac cacgccagcc tgacactgag cacactgacc      240
```

```
gtgacaagcg cccatcctga ggactccagc ttctacatct gtagcgccag aggcggcagc      300
tacaacagcc ctctgcactt tggcaacggc accagactga cagtgaccga ggacctgaag      360
aacgtgttcc cacctgaggt ggccgtgttc gagccttctg aggccgagat cagccacaca      420
cagaaagcca cactcgtgtg tctggccacc ggcttctatc ccgatcacgt ggaactgtct      480
tggtgggtca acggcaaaga ggtgcacagc ggcgtcagca cagatcccca gcctctgaaa      540
gaacagcccg ctctgaacga cagccggtac tgtctgagca gcagactgag agtgtccgcc      600
accttctggc agaaccccag aaaccacttc agatgccagg tgcagttcta cggcctgagc      660
gagaacgatg agtggaccca ggatagagcc aagcctgtga cacagatcgt gtctgccgaa      720
gcctggggca gagccgattg tggctttacc agcgagagct accagcaagg cgtgctgtct      780
gccaccatcc tgtacgagat cctgctgggc aaagccactc tgtacgccgt gctggtgtct      840
gccctggtcc tgatggctat ggtcaagcgg aaggacagca gaggc                     885
```

<210> SEQ ID NO 31
<211> LENGTH: 885
<212> TYPE: DNA
<213> ORGANISM: Artificial Sequence
<220> FEATURE:
<223> OTHER INFORMATION: illustrative TCR beta chain

<400> SEQUENCE: 31

```
ggagctgtgg tgtctcagca cccttcttgg gtcatctgca agagcggcac cagcgtgaag       60
atcgagtgca gaagcctgga cttccaggcc accaccatgt tctggtacag acagttcccc      120
aagcagagcc tgatgctgat ggccacctct aacgagggca gcaaggccac atatgagcag      180
ggcgtcgaga aggacaagtt cctgatcaac cacgccagcc tgacactgag caccctgaca      240
gtgacaagcg cccatcctga ggacagcagc ttctacatct gtagcgccag aggcggcagc      300
tacaacagcc ctctgcactt tggcaacggc accagactga ccgtgaccga ggacctgaag      360
aacgtgttcc cacctgaggt ggccgtgttc gagccttctg aggccgagat cagccacaca      420
cagaaagcca cactcgtgtg tctggccacc ggcttctatc ccgatcacgt cgaactgtct      480
tggtgggtca acggcaaaga ggtgcacagc ggcgtcagca cagatcccca gcctctgaaa      540
gaacagcccg ctctgaacga cagccggtac tgtctgagca gcagactgag agtgtccgcc      600
accttctggc agaaccccag aaaccacttc aggtgccagg tgcagttcta cggcctgagc      660
gagaacgatg agtggaccca ggatagagcc aagcctgtga cacagatcgt gtctgccgaa      720
gcctggggca gagccgattg tggctttacc agcgagagct accagcaagg cgtgctgtct      780
gccaccatcc tgtacgagat cctgctgggc aaagccactc tgtacgccgt gctggtgtct      840
gccctggtcc tgatggctat ggtcaagcgg aaggactcca gaggc                     885
```

<210> SEQ ID NO 32
<211> LENGTH: 333
<212> TYPE: DNA
<213> ORGANISM: Artificial Sequence
<220> FEATURE:
<223> OTHER INFORMATION: sequence encoding TCR alpha chain variable
      region

<400> SEQUENCE: 32

```
gacgccaaga ccacacagcc caacagcatg aaaagcaacg aagaggaacc cgtgcatctg       60
ccctgcaacc acagcacaat cagcggcacc gactacatcc actggtatag acagctgccc      120
tctcagggcc ccgagtatgt gattcacggc ctgaccagca acgtgaacaa ccggatggcc      180
```

-continued

```
tctctggcca ttgccgagga cagaaagtcc agcacactga tcctgcaccg ggccacactg      240
agagatgccg ccgtgtatta ctgcaccgtg tacggcggag ccaccaacaa gctgatcttt      300
ggcacaggca cactgctggc cgtgcagccc aat                                   333
```

```
<210> SEQ ID NO 33
<211> LENGTH: 348
<212> TYPE: DNA
<213> ORGANISM: Artificial Sequence
<220> FEATURE:
<223> OTHER INFORMATION: sequence encoding TCR beta chain variable
      region
```

```
<400> SEQUENCE: 33
```

```
ggagctgtgg tgtctcagca cccttcttgg gtcatctgca agagcggcac cagcgtgaag       60
atcgagtgca gaagcctgga cttccaggcc accaccatgt tctggtacag acagttcccc      120
aagcagagcc tgatgctgat ggccacctct aacgagggca gcaaggccac atatgagcag      180
ggcgtcgaga aggacaagtt cctgatcaac cacgccagcc tgacactgag caccctgaca      240
gtgacaagcg cccatcctga ggacagcagc ttctacatct gtagcgccag aggcggcagc      300
tacaacagcc ctctgcactt tggcaacggc accagactga ccgtgacc                   348
```

ENGINEERED REGULATORY T CELL

FIELD OF THE INVENTION

The present invention relates to an engineered regulatory T cell (Treg). In particular, the present invention relates to a Treg comprising a T cell receptor (TCR) which is capable of specifically binding to myelin basic protein (MBP). The present invention further relates to methods for providing an engineered Treg and to methods and uses of said engineered Treg.

BACKGROUND TO THE INVENTION

Many autoimmune and inflammatory central nervous system (CNS) diseases involve autoreactive T-cells. For example, Multiple Sclerosis (MS), which is an autoimmune inflammatory demyelinating condition of the central nervous system and is the most common neurological disorder among young adults.

Current treatments for autoimmune and inflammatory CNS diseases generally suppress the immune system. For example, one treatment includes transplantation of bone marrow along with administration of cytostatics and immunosupressive drugs. Autologous haematopoietic stem cell transplantation can have lasting beneficial effects for some patients, but the procedure requires aggressive myelo-ablative conditioning which is associated with substantial toxicity and risk.

Although several disease-modifying treatments (DMTs) have been approved to reduce the frequency of clinical relapses, most patients continue to clinically deteriorate under current therapy schedules. Neither DMTs nor stem cell transplantation can mediate CNS-specific suppression of the immunopathology of autoimmune and inflammatory CNS diseases.

Currently, effective treatments for autoimmune and inflammatory CNS diseases do not exist. Treatment is focused on merely reducing its symptoms, usually by general suppression of the immune system. There is a need for a therapy which specifically targets local immune responses associated with onset and progression of CNS disease.

SUMMARY OF ASPECTS OF THE INVENTION

The present invention is based, at least in part, on the inventors' determination that T cell receptor gene transfer technology can be used to generate antigen-specific Tregs. It has been shown that human antigen-specific Tregs can suppress activated T cells.

In particular, the present inventors have produced MBP-specific Tregs for example, by retroviral transfer of MBP-TCR genes into purified Tregs and/or by retroviral transfer of MBP-TCR and forkhead box P3 (FOXP3) genes into conventional CD4$^+$ T cells. Without wishing to be bound by theory, these engineered Tregs with TCRs specific for MBP may be used in the suppression of diseases e.g. autoimmune diseases, where local activation of MBP-specific Tregs in the central nervous system (CNS) may suppress CNS pathology as seen in MS and other CNS inflammatory conditions.

Without wishing to be bound by theory, it was unexpected that the present inventors have been able to develop a Treg which suppresses proliferation of pathogenic T cells. It was previously suggested in the field that TCRs in Tregs have higher affinity for self antigen than TCRs in conventional T cells (Pacholczyk and Kern Immunology, 2008. 125(4)

450-458 incorporated herein by reference). It has also been reported that Tregs transduced with an islet-antigen specific TCR were less efficient than Tregs expressing a viral antigen specific TCR. It was suggested that this may be due Treg-specific TCR requirements—for example a certain affinity requirement. Thus, the Treg repertoire is highly diverse and was thought to have a distinct set of T cell receptors compared to the repertoire of conventional T cells. The present inventors have unexpectedly demonstrated that a MBP-specific TCR isolated from conventional T cells can be successfully expressed in a Treg cell and can produce a functional Treg.

Further, a large number of TCRs cannot be successfully expressed as an exogenous TCR. It cannot be predicted which TCRs can be effectively expressed as an exogenous TCR, in particular in a Treg.

Accordingly, the present invention provides an engineered regulatory T cell (Treg) comprising a T cell receptor, wherein the TCR comprises an α chain and a β chain, wherein the α chain and the β chain each comprises three complementarity determining regions (CDRs) and the sequence of each CDR3 is as follows:

```
CDR3α-
                                    (SEQ ID NO: 1)
TVYGGATNKLI

CDR3β-
                                    (SEQ ID NO: 2)
SARGGSYNSPLH
``` or a variant of those sequences having up to three amino acid changes.

The TCR may be capable of specifically binding to a peptide which comprises at least 90% identity to MBP 111-129 (SEQ ID NO: 12) or a fragment thereof when the peptide is presented by a major histocompatibility complex (MHC) molecule.

The MBP111-129 peptide is known to bind weakly to DRB1*0401 (HLA-DR4). This is in contrast to MBP81-99, for example, which binds with a high affinity to HLA-DR15.

The α chain of the TCR may comprise three CDRs having the following amino acid sequences:

```
CDR1α-
                                    (SEQ ID NO: 3)
TISGTDY

CDR2α-
                                    (SEQ ID NO: 4)
GLTSN

CDR3α-
                                    (SEQ ID NO: 1)
TVYGGATNKLI
``` or variants of those sequences having up to three amino acid changes;
and the β chain of the TCR may comprise three CDRs having the following amino acid sequences:

```
CDR1β-
                                    (SEQ ID NO: 5)
DFQATT

CDR2β-
                                    (SEQ ID NO: 6)
SNEGSK
```

-continued

CDR3β-

(SEQ ID NO: 2)

SARGGSYNSPLH or variants of those sequences having up to three amino acid changes.

The variable region of the α chain of the TCR may comprise an amino acid sequence having at least 80% sequence identity to SEQ ID NO: 7, wherein the sequence identity does not include the CDR sequences; and the variable region of the β chain of the TCR may comprise an amino acid sequence having at least 80% sequence identity to SEQ ID NO: 8, wherein the sequence identity does not include the CDR sequences.

The variable region of the α chain of the TCR may comprise an amino acid sequence having at least 80% sequence identity to SEQ ID NO: 7; and the variable region of the β chain of the TCR may comprise an amino acid sequence having at least 80% sequence identity to SEQ ID NO: 8.

The constant region domains of the α chain and β chain of the TCR may each comprise an additional cysteine residue, enabling the formation of an extra disulphide bond between the α chain and the β chain. Suitably, the additional disulphide bond reduces mispairing with endogenous TCR chains.

Suitably, the TCR may comprise a constant domain as follows:

(a) the β chain of the TCR may comprise a human constant region amino acid sequence which comprises a cysteine residue at the position corresponding to position 22 as shown in SEQ ID NO: 27; or (b) the α chain of the TCR may comprise a human constant region amino acid sequence having at least 80% sequence identity to SEQ ID NO: 26 and/or the β chain of the TCR may comprise a human constant region amino acid sequence having at least 80% sequence identity to SEQ ID NO: 27.

The α chain of the TCR may comprise an amino acid sequence having at least 80% sequence identity to SEQ ID NO: 9; and the β chain of the TCR may comprise an amino acid sequence having at least 80% sequence identity to SEQ ID NO: 10.

In one aspect, the Treg is derived from a T cell isolated from a subject.

In another aspect, the present invention provides a pharmaceutical composition comprising an engineered Treg according to the invention.

In one aspect, the present invention relates to an engineered Treg or pharmaceutical composition according to the invention for use in treating a disease.

In another aspect, the present invention relates to the use of an engineered Treg or pharmaceutical composition according to the invention in the manufacture of a medicament.

In one aspect, there is provided a method for treating or preventing a disease in a subject in need of same which comprises the step of administering an engineered Treg or pharmaceutical composition according to the invention to the subject.

In another aspect, there is provided an engineered Treg or pharmaceutical composition for use, or a use or a method according to the invention, wherein the disease is multiple sclerosis.

In one aspect, there is provided an engineered Treg or pharmaceutical composition for use, or a use or a method according to the invention, wherein the subject is an HLADRB1*0401 positive subject.

Suitably, the present invention provides a vector encoding a TCR according to the invention wherein:

(a) the nucleic acid sequence encoding the α chain of the TCR comprises a sequence having at least 90% sequence identity to SEQ ID NO: 28 or 29;

(b) the nucleic acid sequence encoding the β chain of the TCR comprises a sequence having at least 90% sequence identity to SEQ ID NO: 30 or 31;

(c) the nucleic acid sequence provides the TCR chains in the orientation 5' α chain-β chain 3' and comprises (i) a sequence encoding the α chain of the TCR and having at least 90% sequence identity to SEQ ID NO: 28 and (ii) a sequence encoding the β chain of the TCR and having at least 90% sequence identity to SEQ ID NO: 30; or (d) the nucleic acid sequence provides the TCR chains in the orientation 5' β chain-α chain 3' and comprises (i) a sequence encoding the β chain of the TCR and having at least 90% sequence identity to SEQ ID NO: 31 and (ii) a sequence encoding the α chain of the TCR and having at least 90% sequence identity to SEQ ID NO: 29.

In another aspect, there is provided a vector which comprises a nucleic acid sequence which encodes a TCR as defined herein and a nucleic acid sequence which encodes FOXP3.

In one aspect, a kit of polynucleotides or a kit of vectors is provided which comprises a first polynucleotide or vector which comprises a nucleic acid sequence which encodes a TCR as defined herein and a second polynucleotide or vector which comprises a nucleic acid sequence which encodes FOXP3. Suitably, the first and second polynucleotides or vectors are separate.

In one aspect, there is provided a method for producing an engineered Treg according to the invention which comprises the step of introducing into a cell in vitro or ex vivo a polynucleotide encoding a TCR as defined herein.

Suitably the T cell is a natural Treg which expresses FOXP3.

In one aspect, the method further comprises the step of introducing into the cell in vitro or ex vivo a polynucleotide encoding a FOXP3 protein.

Suitably the cell is a T cell.

Suitably the T cell is a 'conventional' T cell.

Suitably, the cell is a human cell, such as a human T cell. Suitably, the cell is a human Treg cell.

In one aspect of a method of the invention, the step of introducing the polynucleotide encoding a TCR and the polynucleotide encoding FOXP3 are performed sequentially, separately or simultaneously.

In another aspect of a method of the invention, the polynucleotide encoding a TCR and the polynucleotide encoding FOXP3 are introduced to the cell using the vector of the invention.

Figure 15:
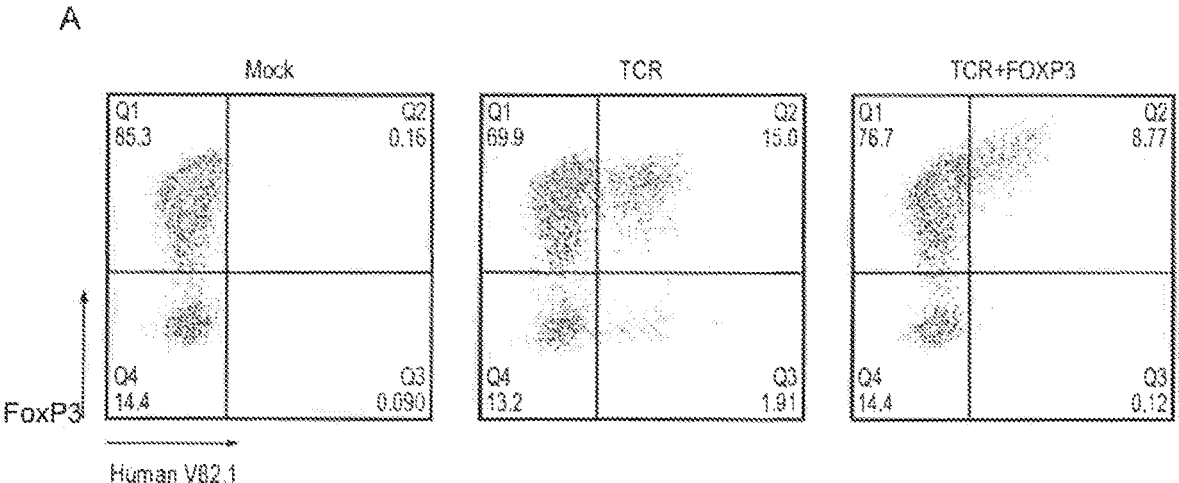
Figure 15:
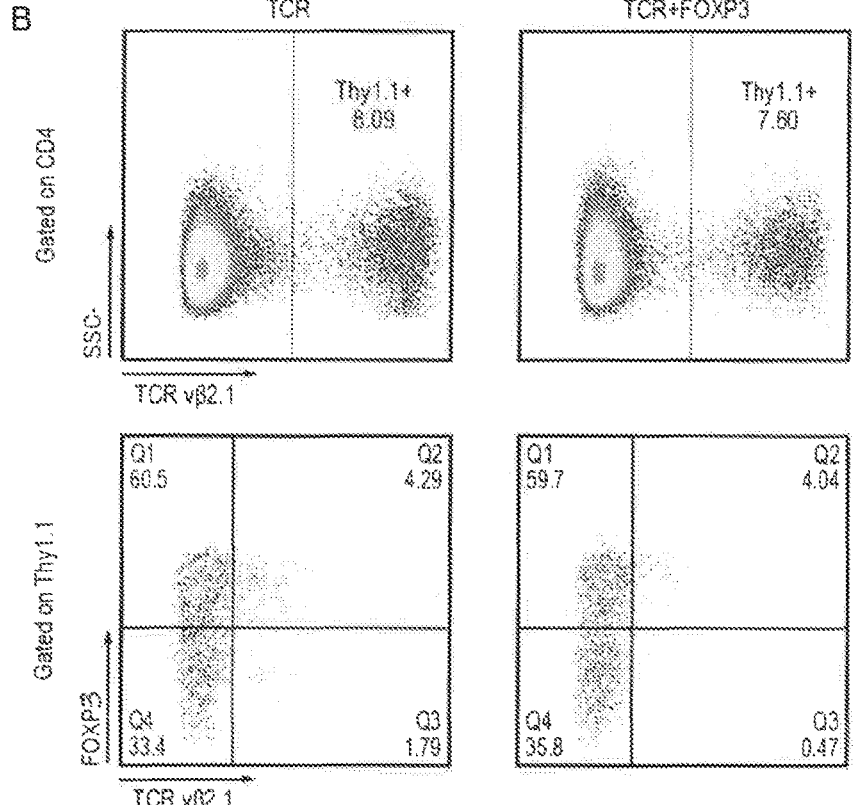
Figure 15:
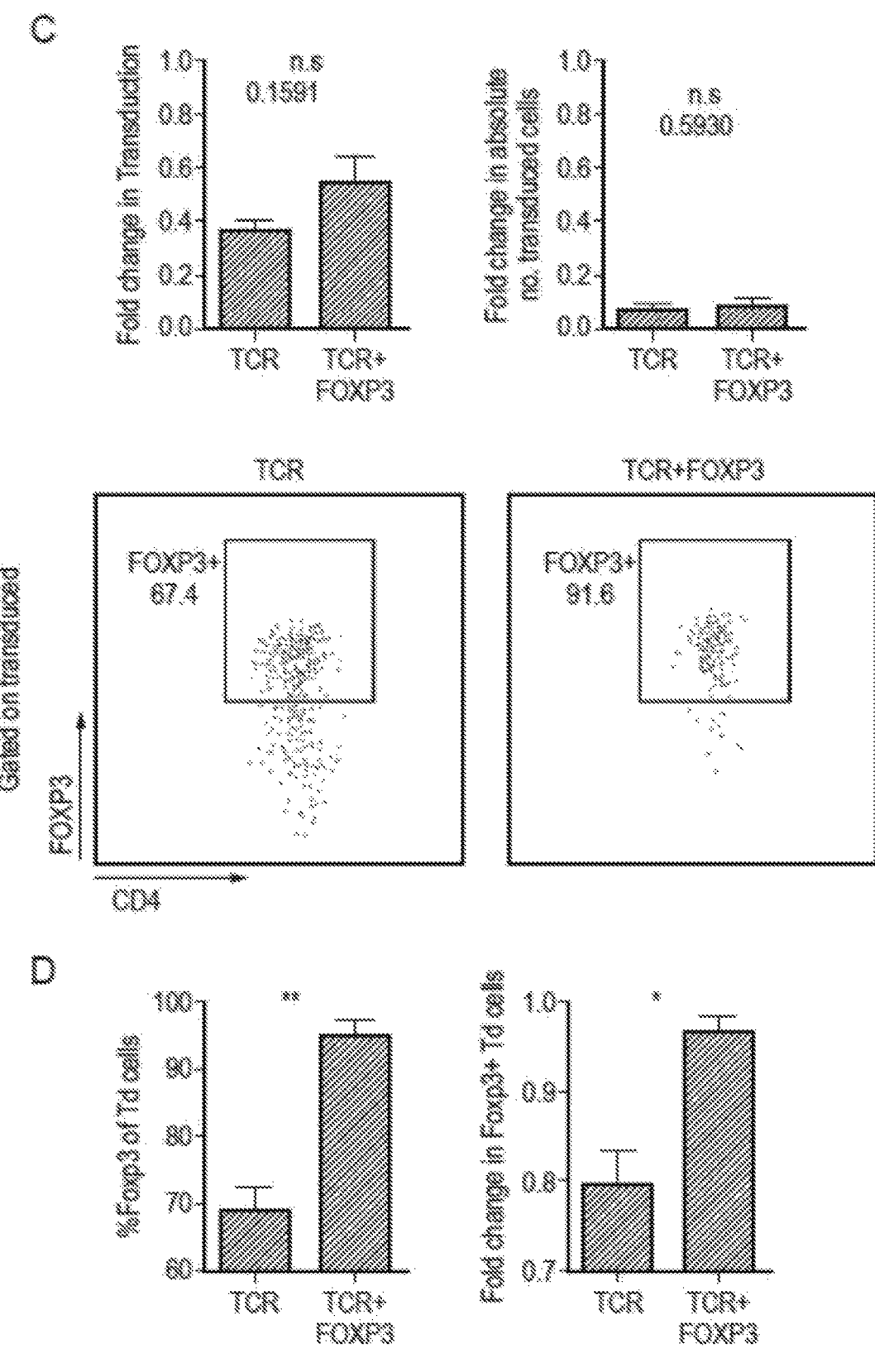

FIG. 15—TCR transduced regulatory T cells can engraft into irradiated hosts but require exogenous FOXP3 expression to prevent accumulation of TCR+FOXP3– cells. Thy1.1+CD4+CD25+ Treg were isolated from lymph nodes and splenocytes of HLA-DRB*0401 transgenic mice by bead sort. Treg were transduced TCR, TCR+murine FOXP3 or cultured with virus-free supernatant (mock). 1 day after transduction TCR or TCR+FOXP3 transduced cells were injected into HLA-DRB*0401 transgenic hosts conditioned with 4 Gy irradiation. 7 weeks later flow cytometry was used to determine the engraftment of transduced Treg A. Transduction efficiency was determined through expression of human variable 2.1 and murine Foxp3 on d1 post-transduction B. Splenocytes from mice that received Treg transduced with TCR or TCR+FOXP3 were stained with Thy1.1 to identify transferred cells (top panel) and FOXP3 and TCR (bottom panel) C. Cumulative data showing fold change in transduction efficiency (left panel) and fold change in absolute number of transduced cells (right panel) relative to day of injection for Treg transduced with TCR or TCR+FOXP3 (n=3). Error bars show standard error of the mean. Statistical analysis by unpaired t test D. Representative expression of FOXP3 within transduced cells 7 weeks after transfer. Graphs show cumulative of percentage FOXP3+ cells within the transduced population at week 7 (left) and the fold change in FOXP3+ cells relative to the day of injection (n=3). Error bars show standard error of the mean. *p=>0.05, **p=>0.01 determined by unpaired t test.

Figure 16:
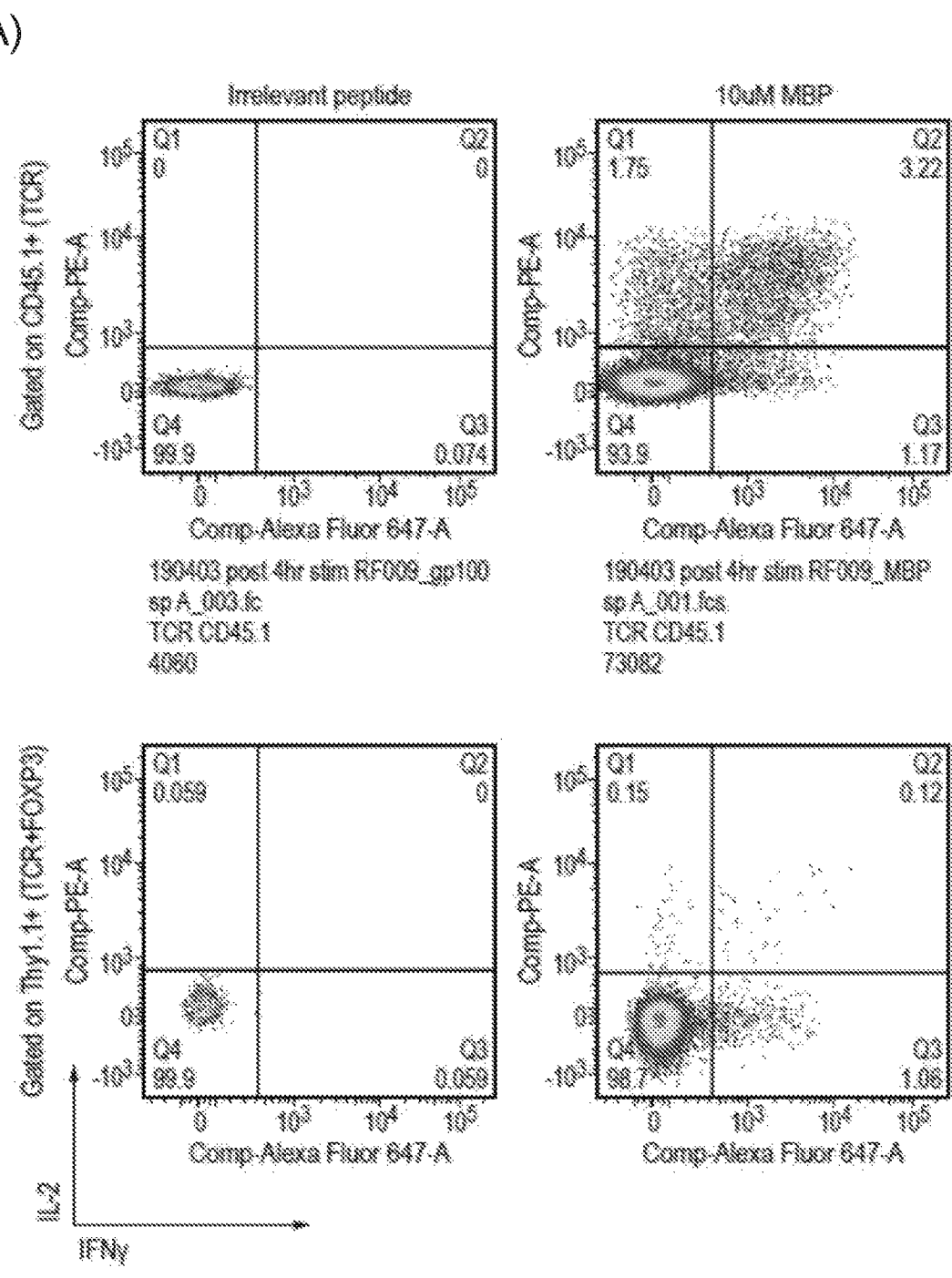
Figure 16:
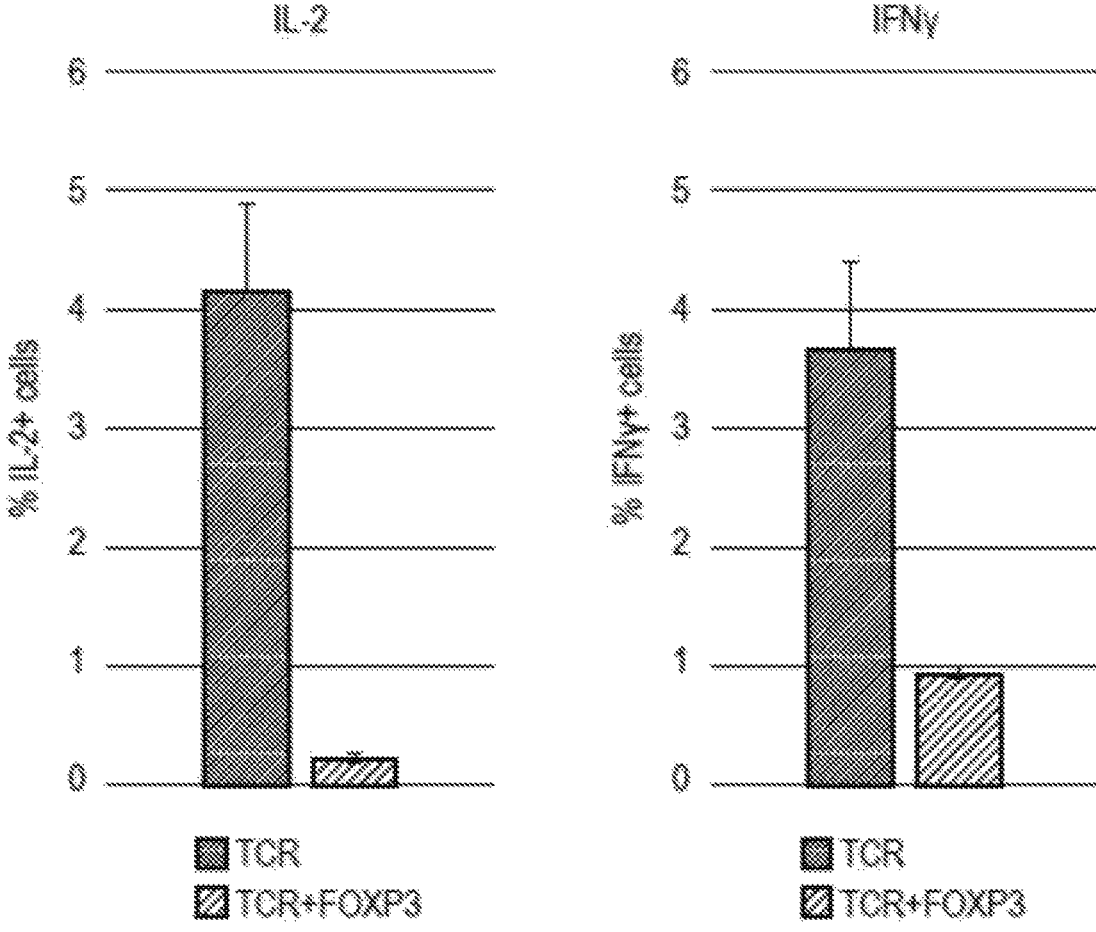

FIG. 16—Treg expressing exogenous FOXP3 retain Treg functionality after 7 weeks in vivo whilst Tregs not expressing exogenous FOXP3 acquire the ability to produce effector cytokines A Splenocytes were cultured for 4 hours with CD86+HLA-DR4+CHO cells pulsed with irrelevant peptide or 10 uM MBP. Production of IL-2 and IFNg was determined by flow cytometry. FACS plots show CD45.1 cells (top panel) containing Treg expressing TCR alone and Thy1.1 cells containing Treg expressing TCR+FOXP3. B Graphs show cumulative IL-2 and IFNg production by TCR-expressing (dark grey) and TCR+FOXP3-expressing (light grey) Treg. Error bars show standard deviation of the mean (n=3)

DETAILED DESCRIPTION

Myelin Basic Protein (MBP) Peptides

Myelin basic protein is important in the process of myelination of nerves and is found in the myelin sheath of cells in the nervous system such as oligodendrocytes and Schwann cells. MBP transcripts are also found in the bone marrow and the immune system. One function of the myelin sheath is to increase the velocity of axonal impulse conduction. MBP helps to maintain the correct structure of myelin and interacts with lipids in the myelin membrane. MBP is known to localise to the CNS and to various haematopoietic cells.

MBP has been implicated in the pathogenesis of demyelinating diseases, such as multiple sclerosis (MS). Studies have demonstrated a role for antibodies against MBP in the pathogenesis of MS.

In one aspect, an illustrative amino acid sequence of MBP comprises the sequence with UniProtKB accession P02686-1, shown as SEQ ID NO: 11:

```
                                        (SEQ ID NO: 11)
MGNHAGKRELNAEKASTNSETNRGESEKKRNLGELSRTTSEDNEVFGEA

DANQNNGTSSQDTAVTDSKRTADPKNAWQDAHPADPGSRPHLIRLFSRD

APGREDNTFKDRPSESDELQTIQEDSAATSESLDVMASQKRPSQRHGSK

YLATASTMDHARHGFLPRHRDTGILDSIGRFFGGDRGAPKRGSGKDSHH

PARTAHYGSLPQKSHGRTQDENPVVHFFKNIVTPRTPPPSQGKGRGLSL

SRFSWGAEGQRPGFGYGGRASDYKSAHKGFKGVDAQGTLSKIFKLGGRD

SRSGSPMARR.
```

An illustrative amino acid sequence of MBP may comprise SEQ ID NO: 11 or a variant or fragment thereof.

Suitably, an illustrative amino acid sequence of MBP may be an isoform of UniProtKB accession P02686-1, such as UniProtKB accession P02686-5. Isoform P02686-5 differs from the canonical sequence shown above in SEQ ID NO:11 as follows, amino acid residues 1-133 are missing.

UniProtKB accession P02686-5 is shown as SEQ ID NO: 13:

```
                                        (SEQ ID NO: 13)
MASQKRPSQRHGSKYLATASTMDHARHGFLPRHRDTGILDSIGRFFGGD

RGAPKRGSGKDSHHPARTAHYGSLPQKSHGRTQDENPVVHFFKNIVTPR

TPPPSQGKGRGLSLSRFSWGAEGQRPGFGYGGRASDYKSAHKGFKGVDA

QGTLSKIFKLGGRDSRSGSPMARR.
```

Unless otherwise stated, MBP XXX-XXX as used herein refers to the numbering used in Muraro et al., JCI 1997; 100, 2, 339-349, incorporated herein by reference or by reference to SEQ ID NO: 13 (not including the initiator methionine).

One may determine whether a peptide is capable of being presented by a MHC molecule and recognised by a T cell using methods available in the art. For example, an assay may comprise co-culturing antigen presenting cells (APCs) expressing the MHC:peptide complex to be tested with T cells comprising the TCR defined herein. T cell proliferation may then be measured as an indication of successful presentation of the peptide (for example by carboxyfluorescein succinimidyl ester (CFSE) assay). Alternatively, effector cytokine production may also be measured.

As used herein "specifically binding" means that the TCR binds to the peptide but does not bind to other peptides, or binds at a lower affinity to other peptides.

The binding affinity between two molecules, e.g. a TCR and a peptide, or fragment thereof, may be quantified for example, by determination of the dissociation constant (KD). The KD can be determined by measurement of the kinetics of complex formation and dissociation between the TCR and the peptide, e.g. by the surface plas, on resonance (SPR) method (Biacore™). The rate constants corresponding to the association and the dissociation of a complex are referred to as the association rate constants ka (or kon) and dissociation rate constant kd. (or koff), respectively. KD is related to ka and kd through the equation KD=kd/ka.

Binding affinities associated with different molecular interactions, e.g. comparison of the binding affinity of different TCRs and peptides, may be compared by comparison of the KD values for the individual TCR/peptide complexes.

The peptide may be capable of being presented by any Human Leukocyte Antigen—antigen D Related (HLA-DR).

In one aspect, the peptide is capable of being presented by a HLA-DR4.

In one aspect, the peptide is capable of being presented by a HLA-DRB1*0401 molecule.

In one aspect, the peptide has at least 90% identity to MBP 111-129: LSRFSWGAEGQRPGFGYGG (SEQ ID NO: 12). The MBP peptide may be mutated compared to MBP 111-129 (SEQ ID NO: 12). For example, the MBP peptide may be mutated by amino acid insertion, deletion or substitution, so long as the modified MBP peptide retains the MHC binding specificity of the unmodified peptide, and is capable of being presented to a T cell. The peptide may, for example have 3, 2, 1 or 0 mutations relative to MBP 111-129 (SEQ ID NO: 12). Suitably the peptide may, for example have 3, 2, 1 or 0 conservative mutations relative to MBP 111-129 (SEQ ID NO: 12). Suitably the peptide may, for example have 3, 2, 1 or 0 insertions relative to MBP 111-129 (SEQ ID NO: 12). Suitably the MBP peptide fragment may, for example have 3, 2, 1 or 0 deletions relative to MBP 111-129 (SEQ ID NO: 12). Suitably, the MBP 111-129 (SEQ ID NO: 12) peptide fragment retains the MHC binding specificity of the MBP 111-129 (SEQ ID NO: 12) peptide, and is capable of being presented to a T cell.

T Cell Receptor (TCR)

The variable domain of both the TCR α-chain and β-chain have three hypervariable or complementarity determining regions (CDRs). CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule. Framework regions (FRs) are positioned between the CDRs. These regions provide the structure of the TCR variable region.

The TCR of the present invention comprises sufficient of the variable domains thereof to be able to interact with its peptide/MHC complex. Such interaction can be measured using a Biacore™ instrument, for example. Suitably the TCR may interact with HLA-DR4 or HLADRB1*0401.

The repertoire of TCR variable regions is generated by combinatorial joining of variable (V), joining (J) and diversity (D) genes; and by N region diversification (nucleotides inserted by the enzyme deoxynucleotidyl-transferase).

α chains are formed from recombination events between the V and J segments. β chains are formed from recombination events involving the V, D and J segments.

The human TCRα locus, which also includes the TCRδ locus, is located on chromosome 14 (14q11.2). The TCRδ locus is located on chromosome 7 (7q34). The variable region of the TCRα chain is formed by recombination between one of 46 different Vα (variable) segments and one of 58 Jα (joining) segments (Koop et al.; 1994; Genomics; 19: 478-493 incorporated herein by reference). The variable region of a TCRβ chain is formed from recombination between 54 Vβ, 14 Jβ and 2 Dβ (diversity) segments (Rowen et al.; 1996; Science; 272:1755-1762 incorporated herein by reference).

The V and J (and D as appropriate) gene segments for each TCR chain locus have been identified and the germline sequence of each gene is known and annotated (for example see Scaviner & Lefranc; 2000; Exp Clin Immunogenet; 17:83-96 and Folch & Lefranc; 2000; Exp Clin Immunogenet; 17:42-54, incorporated herein by reference).

FR1, CDR1, FR2, CDR2, FR3 and CDR3 of the α chain of natural TCRs are encoded by the Vα gene. FR1, CDR1, FR2, CDR2 and FR3 of the β chain of natural TCRs are encoded by the Vβ gene.

As the germline sequence of each variable gene is known in the art (see Scaviner & Lefranc; as above and Folch & Lefranc; supra) the Vα and/or Vβ of a particular TCR can be sequenced and the germline V segment which is utilised in the TCR can be identified (see, for example, Hodges et al.; 2003; J Clin Pathol; 56:1-11, Zhou et al.; 2006; Laboratory Investigation; 86; 314-321, incorporated herein by reference).

The present invention provides an engineered Treg comprising an engineered T cell receptor.

The invention provides an engineered Treg comprising a TCR which is capable of specifically binding to a peptide which comprises at least 90% identity to MBP 111-129 (SEQ ID NO: 12) or a fragment thereof when the peptide is presented by a major histocompatibility complex (MHC) molecule.

In one aspect, the TCR comprises an α chain and a β chain,
wherein the α chain and the β chain each comprises three complementarity determining regions (CDRs) and the sequence of each CDR3 is as follows:

```
CDR3α-
                              (SEQ ID NO: 1)
TVYGGATNKLI

CDR3β-
                              (SEQ ID NO: 2)
SARGGSYNSPLH
``` or a variant of those sequences having up to three amino acid changes.

In one aspect, the α chain of the TCR comprises three CDRs having the following amino acid sequences:

```
CDR1α-
                              (SEQ ID NO: 3)
TISGTDY

CDR2α-
                              (SEQ ID NO: 4)
GLTSN

CDR3α-
                              (SEQ ID NO: 1)
TVYGGATNKLI
``` or variants of those sequences having up to three amino acid changes;
and wherein the β chain of the TCR comprises three CDRs having the following amino acid sequences:

```
CDR1β-
                              (SEQ ID NO: 5)
DFQATT

CDR2β-
                              (SEQ ID NO: 6)
SNEGSK

CDR3β-
                              (SEQ ID NO: 2)
SARGGSYNSPLH
``` or variants of those sequences having up to three amino acid changes.

Suitably the amino acid change in a CDR is a conservative substitution, insertion or deletion. Preferably the amino acid change is a conservative substitution.

In one aspect, the variable region of the α chain of the TCR comprises an amino acid sequence having at least 80% sequence identity to SEQ ID NO:7, and the variable region of the β chain of the TCR comprises an amino acid sequence having at least 80% sequence identity to SEQ ID NO: 8, wherein the sequence identity does not include the CDR sequences. Suitably the CDR sequences are as disclosed herein.

Suitably, the variable region of the α chain of the TCR comprises an amino acid sequence having at least 80%, 85%, 90%, 95% or 97% sequence identity to SEQ ID NO: 7, and the variable region of the β chain of the TCR comprises an amino acid sequence having at least 80%, 85%, 90%, 95%, or 97% sequence identity to SEQ ID NO: 8.

Suitably, the variable region of the α chain of the TCR comprises an amino acid sequence may have at least 85% sequence identity to SEQ ID NO: 7, and the variable region of the β chain of the TCR comprises an amino acid sequence having at least 85% sequence identity to SEQ ID NO: 8, wherein the sequence identity does not include the CDR sequences. Suitably, the variable region of the α chain of the TCR comprises an amino acid sequence may have at least 90% sequence identity to SEQ ID NO: 7, and the variable region of the β chain of the TCR comprises an amino acid sequence having at least 90% sequence identity to SEQ ID NO: 8, wherein the sequence identity does not include the CDR sequences. Suitably, the variable region of the α chain of the TCR comprises an amino acid sequence may have at least 95% sequence identity to SEQ ID NO: 7 and the variable region of the β chain of the TCR comprises an amino acid sequence having at least 95% sequence identity to SEQ ID NO: 8, wherein the sequence identity does not include the CDR sequences. Suitably, the variable region of the α chain of the TCR comprises an amino acid sequence may have at least 97% sequence identity to SEQ ID NO: 7 and the variable region of the β chain of the TCR comprises an amino acid sequence having at least 97% sequence identity to SEQ ID NO: 8, wherein the sequence identity does not include the CDR sequences. Suitably, the variable region of the α chain of the TCR comprises an amino acid sequence set fort in SEQ ID NO: 7 and the variable region of the β chain of the TCR comprises an amino acid sequence set forth in SEQ ID NO: 8, wherein the sequence identity does not include the CDR sequences.

In other words, the TCR may comprise the α chain and β chain CDRs as defined herein, and at least 80%, 85%, 90%, 95% or 97% sequence identity across the remaining sequence of SEQ ID NO: 7 and/or SEQ ID NO: 8.

In another aspect, the variable region of the α chain of the TCR comprises an amino acid sequence having at least 80% sequence identity to SEQ ID NO: 7; and the variable region of the β chain of the TCR comprises an amino acid sequence having at least 80% sequence identity to SEQ ID NO: 8.

Suitably, the variable region of the α chain of the TCR comprises an amino acid sequence having at least 85% sequence identity to SEQ ID NO: 7; and the variable region of the β chain of the TCR comprises an amino acid sequence having at least 85% sequence identity to SEQ ID NO: 8. Suitably, the variable region of the α chain of the TCR comprises an amino acid sequence having at least 90% sequence identity to SEQ ID NO: 7; and the variable region of the β chain of the TCR comprises an amino acid sequence having at least 90% sequence identity to SEQ ID NO: 8.

Suitably, the variable region of the α chain of the TCR comprises an amino acid sequence having at least 95% sequence identity to SEQ ID NO: 197 and the variable region of the β chain of the TCR comprises an amino acid sequence having at least 95% sequence identity to SEQ ID NO: 8. Suitably, the variable region of the α chain of the TCR comprises an amino acid sequence having at least 97% sequence identity to SEQ ID NO: 7; and the variable region of the β chain of the TCR comprises an amino acid sequence having at least 97% sequence identity to SEQ ID NO: 8.

```
Illustrative TCR α chain variable region
                                     (SEQ ID NO: 7)
DAKTTQPNSMESNEEEPVHLPCNHSTISGTDYIHWYRQLPSQGPEYVIH
GLTSNVNNRMASLAIAEDRKSSTLILHRATLRDAAVYYCTVYGGATNKL
IFGTGTLLAVQPN Illustrative TCR β chain variable region
                                     (SEQ ID NO: 8)
GAVVSQHPSWVICKSGTSVKIECRSLDFQATTMFWYRQFPKQSLMLMAT
SNEGSKATYEQGVEKDKFLINHASLTLSTLTVTSAHPEDSSFYICSARG
GSYNSPLHFGNGTRLTVT
```

Suitably, the α chain of the TCR comprises a human constant region amino acid sequence having at least 80% sequence identity to SEQ ID NO: 26 and/or the β chain of the TCR comprises a human constant region amino acid sequence having at least 80% sequence identity to SEQ ID NO: 27.

Suitably, the TCR α chain constant region may comprise an amino acid sequence having at least 80% sequence identity to SEQ ID NO: 26. Suitably, the TCR α chain constant region may comprise an amino acid sequence having at least 80%, at least 85%, at least 90%, at least 95% or at least 99% sequence identity to SEQ ID NO: 26.

Suitably, the TCR α chain constant region may comprise an amino acid sequence having at least 80% sequence identity to SEQ ID NO: 27. Suitably, the TCR α chain constant region may comprise an amino acid sequence having at least 80%, at least 85%, at least 90%, at least 95% or at least 99% sequence identity to SEQ ID NO: 27.

Suitably, the β chain of the TCR comprises a human constant region amino acid sequence which comprises a cysteine residue at position 22 as shown in SEQ ID NO: 27.

```
Illustrative TCR α chain constant region
                                     (SEQ ID NO: 26)
IQNPDPAVYQLRDSKSSDKSVCLFTDFDSQTNVSQSKDSDVYITDKTVL

DMRSMDFKSNSAVAWSNKSDFACANAFNNSIIPEDTFFPSPESSCDVKL

VEKSFETDTNLNFQNLSVIGFRILLLKVAGFNLLMTLRLWSS

Illustrative TCR β chain constant region
                                     (SEQ ID NO: 27)
EDLKNVFPPEVAVFEPSEAEISHTQKATLVCLATGFYPDHVELSWNGKE

VHSGVSTDPQPLKEQPALNDSRYCLSSRLRVSATFWQNPRNHFRCQVQF

YGLSENDEWTQDRAKPVTQIVSAEAWGRADCGFTSESYQQGVLSATILY

EILLGKATLYAVLVSALVLMAMVKRKDSRG
```

In one aspect, the α chain of the TCR comprises an amino acid sequence having at least 80% sequence identity to SEQ ID NO: 9; and the β chain of the TCR comprises an amino acid sequence having at least 80% sequence identity to SEQ ID NO: 10.

Illustrative TCR α chain (SEQ ID NO: 9)

DAKTTQPNSMESNEEEPVHLPCNHSTISGTDYIHWYRQLPSQGPEYVIH

GLTSNVNNRMASLAIAEDRKSSTLILHRATLRDAAVYYCTVYGGATNKL

IFGTGTLLAVQPNIQNPDPAVYQLRDSKSSDKSVCLFTDFDSQTNVSQS

KDSDVYITDKTVLDMRSMDFKSNSAVAWSNKSDFACANAFNNSIIPEDT

FFPSPESSCDVKLVEKSFETDTNLNFQNLSVIGFRILLLKVAGFNLLMT

LRLWSS

Illustrative TCR β chain (SEQ ID NO: 10)

GAVVSQHPSWWICKSGTSVKIECRSLDFQATTMFWYRQFPKQSLMLMAT

SNEGSKATYEQGVEKDKFLINHASLTLSTLTVTSAHPEDSSFYICSARG

GSYNSPLHFGNGTRLTVTEDLKNVFPPEVAVFEPSEAEISHTQKATLVC

LATGFYPDHVELSWWVNGKEVHSGVSTDPQPLKEQPALNDSRYCLSSRL

RVSATFWQNPRNHFRCQVQFYGLSENDEWTQDRAKPVTQIVSAEAWGRA

DCGFTSESYQQGVLSATILYEILLGKATLYAVLVSALVLMAMVKRKDSR

G

Suitably, the β chain of the TCR comprises a human constant region amino acid sequence which comprises a cysteine residue at position 22 of constant region (underlined) as shown in SEQ ID NO: 10.

Suitably, the α chain of the TCR comprises an amino acid sequence having at least 85% sequence identity to SEQ ID NO: 9; and the β chain of the TCR comprises an amino acid sequence having at least 85% sequence identity to SEQ ID NO: 10. Suitably, the α chain of the TCR comprises an amino acid sequence having at least 90% sequence identity to SEQ ID NO: 9; and the β chain of the TCR comprises an amino acid sequence having at least 90% sequence identity to SEQ ID NO: 10. Suitably, the α chain of the TCR comprises an amino acid sequence having at least 95% sequence identity to SEQ ID NO: 9; and the β chain of the TCR comprises an amino acid sequence having at least 95% sequence identity to SEQ ID NO: 10. Suitably, the α chain of the TCR comprises an amino acid sequence having at least 97% sequence identity to SEQ ID NO: 9; and the β chain of the TCR comprises an amino acid sequence having at least 97% sequence identity to SEQ ID NO: 10.

In another aspect, the constant region domains of the α chain and β chain of the TCR each comprise an additional cysteine residue, enabling the formation of an extra disulphide bond between the α chain and the β chain.

Suitably, residue 48 in the constant alpha chain is converted from a threonine to a cysteine and residue 57 of the constant beta chain is converted from a serine to a cysteine for the formation of the additional disulphide bond.

Suitably, the TCR is codon optimised.

Suitably, the TCR is codon optimised for expression in a mouse.

In one aspect the constant domains employed in the TCR are murine sequences.

Suitably the constant regions have been murinised. For example, both the constant-alpha and the constant-beta domains have been murinised.

In another aspect, the TCR is codon optimised for expression in a human. Suitably, the constant domains employed in the TCR are human sequences.

In one aspect the TCR may comprise, for example, human variable regions and murine constant regions.

The present TCR may comprise one or more amino acid residues as defined herein which is not encoded by the germline Vα or Vβ gene. In other words, the TCR may comprise part of an α chain and/or β chain which comprises an altered amino acid residue at one or more of the positions described herein, compared to the corresponding α chain and/or β chain as encoded by the unaltered germline Vα or Vβ gene.

The amino acid residues identified herein as framework (FR) or complementarity-determining regions (CDRs) are identified according to the International ImMunoGeneTics information system' (IMGT). This system is well known in the art (Lefrance et al.; 2003; Dev Comp Immunol; 27: 55-77) and is based on the high conservation of the structure of the variable region. The numbering takes into account and combines the definition of the FR and CDRs, structural data from X-ray diffraction studies and the characterization of the hypervariable loops.

The delimitations of the FR and CDR regions are defined within the IMGT numbering system. The FR1 region comprises positions 1-26 (25-26 amino acids, depending on the V-GENE group or subgroup) with 1st-CYS at position 23. The FR2 region comprises positions 39-55 (16-17 amino acids) with a conserved TRP at position 41. The FR3 region comprises positions 66-104 (36-39 amino acids, depending on the VGENE group or subgroup) with a conserved hydrophobic amino acid at position 89 and the 2nd-CYS at position 104. Residue 1 of the IGMT numbering system is the first residue in FR1. Residue 104 of the IGMT numbering system is the last residue in FR3.

Methods suitable for generating a TCR according to the present invention are known in the art.

For example mutagenesis may be performed to alter specific nucleotides in a nucleic acid sequence encoding the TCR. Such mutagenesis will alter the amino acid sequence of the TCR so that it comprises one or more of the amino acid residues as described herein.

An example of a mutagenesis method is the Quikchange method (Papworth et al.; 1996; Strategies; 9(3); 3-4). This method involves the use of a pair of complementary mutagenic primers to amplify a template nucleic acid sequence in a thermocycling reaction using a high-fidelity non-strand-displacing DNA polymerase, such as pfu polymerase.

The terms "one or more" or "at least one" as used herein may include one, two, three, four, five, six, seven, eight, nine, ten, eleven, twelve, thirteen, fourteen, fifteen, sixteen, seventeen, eighteen, nineteen, twenty or more amino acid residues as described herein.

The term "two or more" as used herein may include two, three, four, five, six, seven, eight, nine, ten, eleven, twelve, thirteen, fourteen, fifteen, sixteen, seventeen, eighteen, nineteen, twenty or more amino acid residues as described herein.

Conservative Substitution

Suitably, the amino acid residues present at a given position in the present invention may be defined as a residue which is biochemically similar to the amino acids recited for the given SEQ ID NOs.

Amino acids with similar biochemical properties may be defined as amino acids which can be substituted via a conservative substitution.

Conservative amino acid substitutions may be made on the basis of similarity in polarity, charge, solubility, hydrophobicity, hydrophilicity, and/or the amphipathic nature of the residues as long as high expression of the TCR is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to Table 3 below. Amino acids in the same block in the second column and preferably in the same line in the third column may be substituted for each other:

TABLE 3

| ALIPHATIC | Non-polar | G A P I L V |
| | Polar—uncharged | C S T M N Q |
| | Polar—charged | D E K R |
| AROMATIC | | H F W Y |

The present invention also encompasses homologous substitution (substitution and replacement are both used herein to mean the interchange of an existing amino acid residue, with an alternative residue) i.e. like-for-like substitution such as basic for basic, acidic for acidic, polar for polar etc.

Unless otherwise explicitly stated herein by way of reference to a specific, individual amino acid, amino acids may be substituted using conservative substitutions as recited below.

An aliphatic, non-polar amino acid may be a glycine, alanine, proline, isoleucine, leucine or valine residue.

An aliphatic, polar uncharged amino may be a cysteine, serine, threonine, methionine, asparagine or glutamine residue.

An aliphatic, polar charged amino acid may be an aspartic acid, glutamic acid, lysine or arginine residue.

An aromatic amino acid may be a histidine, phenylalanine, tryptophan or tyrosine residue.

Suitably, a conservative substitution may be made between amino acids in the same line in Table 3.

Sequences

The present invention further provides a nucleotide sequence encoding a TCR α chain and/or β chain described herein. In one aspect, a nucleotide sequence encoding a TCR described herein may be introduced into a cell.

Suitably, the nucleotide sequence encoding the TCR α chain variable regions may comprise SEQ ID NO: 14 or 32 or a sequence having at least 80% sequence identity to SEQ ID NO: 14 or 32. Suitably, the nucleotide sequence may have at least 85%, 90%, 95%, or 99% identity to SEQ ID NO: 14 or 32.

SEQ ID NO: 14
GACGCCAAGACCACACAGCCCAACAGCATGGAAAGCAACGAAGAGGAAC

CCGTGCATCTGCCCTGCAACCACAGCACAATCAGCGGCACCGACTACAT

CCACTGGTACGACAGCTGCCCAGCCAGGGACCTGAGTATGTGATCCAC

GGCCTGACCAGCAACGTGAACAACAGAATGGCCAGCCTGGCTATCGCCG

16

-continued
AGGACAGAAAGAGCAGCACCCTGATCCTGCACAGAGCCACACTGAGAGA

TGCCGCCGTGTACTACTGCACCGTGTATGGCGGAGCCACCAACAAGCTG

ATCTTCGGCACTGGAACACTGCTGGCCGTGCAGCCCAAT

SEQ ID NO: 32
GACGCCAAGACCACACAGCCCAACAGCATGGAAAGCAACGAAGAGGAAC

CCGTGCATCTGCCCTGCAACCACAGCACAATCAGCGGCACCGACTACAT

CCACTGGTATAGACAGCTGCCCTCTCAGGGCCCCGAGTATGTGATTCAC

GGCCTGACCAGCAACGTGAACAACCGGATGGCCTCTCTGGCCATTGCCG

AGGACAGAAAGTCCAGCACACTGATCCTGCACCGGGCCACACTGAGAGA

TGCCGCCGTGTATTACTGCACCGTGTACGGCGGAGCCACCAACAAGCTG

ATCTTTGGCACAGGCACACTGCTGGCCGTGCAGCCCAAT

Suitably, the nucleotide sequence encoding the TCR β chain variable regions may comprise SEQ ID NO: 15 or 33 or a sequence having at least 80% sequence identity to SEQ ID NO: 15 or 33. Suitably, the nucleotide sequence may have at least 85%, 90%, 95%, or 99% identity to SEQ ID NO: 15 or 33.

SEQ ID NO: 15
GGAGCTGTGGTGTCTCAGCACCCCTCTTGGGTCATCTGCAAGAGCGGCAC

CAGCGTGAAGATCGAGTGCAGAAGCCTGGACTTCCAGGCCACCACCATGT

TTTGGTACAGGCAGTTCCCCAAGCAGAGCCTGATGCTGATGGCCACCTCT

AACGAGGGCAGCAAGGCCACATATGAGCAGGGCGTCGAGAAGGACAAGTT

CCTGATCAACCACGCCAGCCTGACACTGAGCACACTGACCGTGACAAGCG

CCCATCCTGAGGACTCCAGCTTCTACATCTGTAGCGCCAGAGGCGGCAGC

TACAACAGCCCTCTGCACTTTGGCAACGGCACCAGACTGACAGTGACC

SEQ ID NO: 33
GGAGCTGTGGTGTCTCAGCACCCTTCTTGGGTCATCTGCAAGAGCGGCAC

CAGCGTGAAGATCGAGTGCAGAAGCCTGGACTTCCAGGCCACCACCATGT

TCTGGTACAGACAGTTCCCCAAGCAGAGCCTGATGCTGATGGCCACCTCT

AACGAGGGCAGCAAGGCCACATATGAGCAGGGCGTCGAGAAGGACAAGTT

CCTGATCAACCACGCCAGCCTGACACTGAGCACCCTGACAGTGACAAGCG

CCCATCCTGAGGACAGCAGCTTCTACATCTGTAGCGCCAGAGGCGGCAGC

TACAACAGCCCTCTGCACTTTGGCAACGGCACCAGACTGACCGTGACC

Suitably, the nucleotide sequence encoding the TCR α chain may comprise SEQ ID NO: 16 or a sequence having at least 80% sequence identity to SEQ ID NO: 16. Suitably, the nucleotide sequence may have at least 85%, 90%, 95%, or 99% identity to SEQ ID NO: 16.

SEQ ID NO: 16
GATGCTAAGACCACACAGCCAAATTCAATGGAGAGTAACGAAGAAGAGC

CTGTTCACTTGCCTTGTAACCACTCCACAATCAGTGGAACTGATTACAT

ACATTGGTATCGACAGCTTCCCTCCCAGGGTCCAGAGTACGTGATTCAT

GGTCTTACAAGCAATGTGAACAACAGAATGGCCTCTCTGGCAATCGCTG

AAGACAGAAAGTCCAGTACCTTGATCCTGCACCGTGCTACCTTGAGAGA

TGCTGCTGTGTACTACTGCACCGTGTATGGCGGAGCCACCAACAAGCTG

-continued

ATCTTCGGCACTGGAACACTGCTGGCCGTGCAGCCCAAT<u>ATCCAGAACC</u>

<u>CTGACCCTGCCGTGTACCAGCTGAGAGACTCTAAATCCAGTGACAAGTC</u>

<u>TGTCTGCCTATTCACCGATTTTGATTCTCAAACAAATGTGTCACAAAGT</u>

<u>AAGGATTCTGATGTGTATATCACAGACAAAACTGTGCTAGACATGAGGT</u>

<u>CTATGGACTTCAAGAGCAACAGTGCTGTGGCCTGGAGCAACAAATCTGA</u>

<u>CTTTGCATGTGCAAACGCCTTCAACAACAGCATTATTCCAGAAGACACC</u>

<u>TTCTTCCCCAGCCCAGAAAGTTCCTGTGATGTCAAGCTGGTCGAGAAAA</u>

<u>GCTTTGAAACAGATACGAACCTAAACTTTCAAAACCTGTCAGTGATTGG</u>

<u>GTTCCGAATCCTCCTCCTGAAAGTGGCCGGGTTTAATCTGCTCATGACG</u>

<u>CTGCGGCTGTGGTCCAGC</u>

Suitably, the nucleotide sequence encoding the TCR β chain may comprise SEQ ID NO: 17 or a sequence having at least 80% sequence identity to SEQ ID NO: 17. Suitably, the nucleotide sequence may have at least 85%, 90%, 95%, or 99% identity to SEQ ID NO: 17.

SEQ ID NO: 17
GGTGCTGTCGTCTCTCAACATCCGAGCTGGGTTATCTGTAAGAGTGGAA

CCTCTGTGAAGATCGAGTGCCGTTCCCTGGACTTTCAGGCCACAACTAT

GTTTTGGTATCGTCAGTTCCCGAAACAGAGTCTCATGCTGATGGCAACT

TCCAATGAGGGCTCCAAGGCCACATACGAGCAAGGCGTCGAGAAGGACA

AGTTTCTCATCAACCATGCAAGCCTGACCTTGTCCACTCTGACAGTGAC

CAGTGCCCATCCTGAAGACAGCAGCTTCTACATCTGCAGTGCTAGAGGC

GGCAGCTACAACAGCCCTCTGCACTTTGGCAACGGCACCAGACTGACAG

TGACC<u>GAGGACCTGAAAAACGTGTTCCCACCCGAGGTCGCTGTGTTTGA</u>

<u>GCCATCAGAAGCAGAGATCTCCCACACCCAAAAGGCCACACTGGTGTGC</u>

<u>CTGGCCACAGGCTTCTACCCCGACCACGTGGAGCTGAGCTGGTGGGTGA</u>

-continued

<u>ATGGGAAGGAGGTGCACAGTGGGGTCAGCACAGACCCGCAGCCCCTCAA</u>

<u>GGAGCAGCCCGCCCTCAATGACTCCAGATACTGCCTGAGCAGCCGCCTG</u>

<u>AGGGTCTCGGCCACCTTCTGGCAGAACCCCCGCAACCACTTCCGCTGTC</u>

<u>AAGTCCAGTTCTACGGGCTCTCGGAGAATGACGAGTGGACCCAGGATAG</u>

<u>GGCCAAACCTGTCACCCAGATCGTCAGCGCCGAGGCCTGGGGTAGAGCA</u>

<u>GACTGTGGCTTCACCTCCGAGTCTTACCAGCAAGGGGTCCTGTCTGCCA</u>

<u>CCATCCTCTATGAGATCTTGCTAGGGAAGGCCACCTTGTATGCCGTGCT</u>

<u>GGTCAGTGCCCTCGTGCTGATGGCCATGGTCAAGAGAAAGGATTCCAGA</u>

<u>GGC</u>

Suitably, the nucleic acid sequence encoding the α chain of the TCR comprises a sequence having at least 90% sequence identity to SEQ ID NO: 28 or 30. Suitably, the nucleic acid sequence encoding the α chain of the TCR comprises a sequence having at least 95% or at least 99% sequence identity to SEQ ID NO: 28 or 30

Suitably, the nucleic acid sequence encoding the β chain of the TCR comprises a sequence having at least 90% sequence identity to SEQ ID NO: 29 or 31. Suitably, the nucleic acid sequence encoding the α chain of the TCR comprises a sequence having at least 95% or at least 99% sequence identity to SEQ ID NO: 29 or 31.

Suitably, the nucleic acid sequence provides the TCR chains in the orientation 5' α chain-β chain 3' and comprises (i) a sequence encoding the α chain of the TCR and having at least 90%, at least 95% or at least 99% sequence identity to SEQ ID NO: 28 and (ii) a sequence encoding the β chain of the TCR and having at least 90%, at least 95% or at least 99% sequence identity to SEQ ID NO: 30.

Suitably, the nucleic acid sequence provides the TCR chains in the orientation 5' β chain-α chain 3' and comprises (i) a sequence encoding the β chain of the TCR and having at least 90%, at least 95% or at least 99% sequence identity to SEQ ID NO: 31 and (ii) a sequence encoding the α chain of the TCR and having at least 90%, at least 95% or at least 99% sequence identity to SEQ ID NO: 29.

-Illustrative TCR α chain
SEQ ID NO: 28
GACGCCAAGACCACACAGCCCAACAGCATGGAAAGCAACGAAGAGGAACCCGTGCATCTG

CCCTGCAACCACAGCACAATCAGCGGCACCGACTACATCCACTGGTACAGACAGCTGCCC

AGCCAGGGACCTGAGTATGTGATCCACGGCCTGACCAGCAACGTGAACAACAGAATGGCC

AGCCTGGCTATCGCCGAGGACAGAAAGAGCAGCACCCTGATCCTGCACAGAGCCACACTG

AGAGATGCCGCCGTGTACTACTGCACCGTGTATGGCGGAGCCACCAACAAGCTGATCTTC

GGCACTGGAACACTGCTGGCCGTGCAGCCCAAT<u>ATTCAGAACCCAGATCCTGCCGTGTAC</u>

<u>CAGCTGAGAGACAGCAAGTCCAGCGACAAGAGCGTGTGCCTGTTCACCGACTTCGACAGC</u>

<u>CAGACCAACGTGTCCCAGAGCAAGGACTCCGATGTGTATATCACCGACAAGACCGTGCTG</u>

<u>GACATGCGGAGCATGGACTTCAAGAGCAACAGCGCCGTGGCCTGGTCCAACAAGAGCGA</u>

<u>TTTCGCCTGCGCCAACGCCTTCAACAACAGCATTATCCCTGAGGACACATTCTTCCCAAGT</u>

<u>CCTGAGAGCAGCTGCGACGTGAAACTGGTGGAAAAGAGCTTCGAGACAGACACCAACCTG</u>

<u>AACTTCCAGAACCTGAGCGTGATCGGCTTCAGAATCCTGCTGCTGAAGGTGGCCGGCTTC</u>

<u>AACCTGCTGATGACCCTGAGACTTTGGAGCAGC</u>

-continued

-Illustrative TCR α chain
                                                          SEQ ID NO: 29
GACGCCAAGACCACACAGCCCAACAGCATGGAAAGCAACGAAGAGGAACCCGTGCATCTG

CCCTGCAACCACAGCACAATCAGCGGCACCGACTACATCCACTGGTATAGACAGCTGCCC

TCTCAGGGCCCCGAGTATGTGATTCACGGCCTGACCAGCAACGTGAACAACCGGATGGCC

TCTCTGGCCATTGCCGAGGACAGAAAGTCCAGCACACTGATCCTGCACCGGGCCACACTG

AGAGATGCCGCCGTGTATTACTGCACCGTGTACGGCGGAGCCACCAACAAGCTGATCTTT

GGCACAGGCACACTGCTGGCCGTGCAGCCCAAT<u>ATTCAGAACCCTGATCCAGCCGTGTAC</u>

<u>CAGCTGAGAGACAGCAAGAGCAGCGACAAGTCTGTGTGTCTGTTCACCGACTTCGACAGC</u>

<u>CAGACCAACGTGTCCCAGAGCAAGGACTCCGATGTGTATATCACCGACAAGACCGTGCTG</u>

<u>GACATGCGGAGCATGGACTTCAAGAGCAACAGCGCCGTGGCCTGGTCCAACAAGAGCGA</u>

<u>TTTTGCCTGCGCCAACGCCTTCAACAACAGCATTATCCCCGAGGACACATTCTTCCCAAGT</u>

<u>CCTGAGAGCAGCTGCGACGTGAAACTGGTGGAAAAGAGCTTCGAGACAGACACCAACCTG</u>

<u>AACTTCCAGAACCTGAGCGTGATCGGCTTCAGAATCCTGCTGCTGAAGGTGGCCGGCTTC</u>

<u>AACCTGCTGATGACCCTGAGACTGTGGTCTAGC</u>

-Illustrative TCR β chain
                                                          SEQ ID NO: 30
GGAGCTGTGGTGTCTCAGCACCCCTCTTGGGTCATCTGCAAGAGCGGCACCAGCGTGAAG

ATCGAGTGCAGAAGCCTGGACTTCCAGGCCACCACCATGTTTTGGTACAGGCAGTTCCCC

AAGCAGAGCCTGATGCTGATGGCCACCTCTAACGAGGGCAGCAAGGCCACATATGAGCAG

GGCGTCGAGAAGGACAAGTTCCTGATCAACCACGCCAGCCTGACACTGAGCACACTGACC

GTGACAAGCGCCCATCCTGAGGACTCCAGCTTCTACATCTGTAGCGCCAGAGGCGGCAGC

TACAACAGCCCTCTGCACTTTGGCAACGGCACCAGACTGACAGTGACC<u>GAGGACCTGAAG</u>

<u>AACGTGTTCCCACCTGAGGTGGCCGTGTTCGAGCCTTCTGAGGCCGAGATCAGCCACACA</u>

<u>CAGAAAGCCACACTCGTGTGTCTGGCCACCGGCTTCTATCCCGATCACGTGGAACTGTCTT</u>

<u>GGTGGGTCAACGGCAAAGAGGTGCACAGCGGCGTCAGCACAGATCCCCAGCCTCTGAAA</u>

<u>GAACAGCCCGCTCTGAACGACAGCCGGTACTGTCTGAGCAGCAGACTGAGAGTGTCCGC</u>

<u>CACCTTCTGGCAGAACCCCAGAAACCACTTCAGATGCCAGGTGCAGTTCTACGGCCTGAG</u>

<u>CGAGAACGATGAGTGGACCCAGGATAGAGCCAAGCCTGTGACACAGATCGTGTCTGCCGA</u>

<u>AGCCTGGGGCAGAGCCGATTGTGGCTTTACCAGCGAGAGCTACCAGCAAGGCGTGCTGT</u>

<u>CTGCCACCATCCTGTACGAGATCCTGCTGGGCAAAGCCACTCTGTACGCCGTGCTGGTGT</u>

<u>CTGCCCTGGTCCTGATGGCTATGGTCAAGCGGAAGGACAGCAGAGGC</u>

-Illustrative TCR β chain
                                                          SEQ ID NO: 31
GGAGCTGTGGTGTCTCAGCACCCCTTCTTGGGTCATCTGCAAGAGCGGCACCAGCGTGAAG

ATCGAGTGCAGAAGCCTGGACTTCCAGGCCACCACCATGTTCTGGTACAGACAGTTCCCC

AAGCAGAGCCTGATGCTGATGGCCACCTCTAACGAGGGCAGCAAGGCCACATATGAGCAG

GGCGTCGAGAAGGACAAGTTCCTGATCAACCACGCCAGCCTGACACTGAGCACCCTGACA

GTGACAAGCGCCCATCCTGAGGACAGCAGCTTCTACATCTGTAGCGCCAGAGGCGGCAG

CTACAACAGCCCTCTGCACTTTGGCAACGGCACCAGACTGACCGTGACC<u>GAGGACCTGAA</u>

<u>GAACGTGTTCCCACCTGAGGTGGCCGTGTTCGAGCCTTCTGAGGCCGAGATCAGCCACAC</u>

<u>ACAGAAAGCCACACTCGTGTGTCTGGCCACCGGCTTCTATCCCGATCACGTCGAACTGTCT</u>

<u>TGGTGGGTCAACGGCAAAGAGGTGCACAGCGGCGTCAGCACAGATCCCCAGCCTCTGAA</u>

<u>AGAACAGCCCGCTCTGAACGACAGCCGGTACTGTCTGAGCAGCAGACTGAGAGTGTCCGC</u>

-continued

CACCTTCTGGCAGAACCCCAGAAACCACTTCAGGTGCCAGGTGCAGTTCTACGGCCTGAG

CGAGAACGATGAGTGGACCCAGGATAGAGCCAAGCCTGTGACACAGATCGTGTCTGCCGA

AGCCTGGGGCAGAGCCGATTGTGGCTTTACCAGCGAGAGCTACCAGCAAGGCGTGCTGT

CTGCCACCATCCTGTACGAGATCCTGCTGGGCAAAGCCACTCTGTACGCCGTGCTGGTGT

CTGCCCTGGTCCTGATGGCTATGGTCAAGCGGAAGGACTCCAGAGGC

As used herein, the term "introduced" refers to methods for inserting foreign DNA into a cell. As used herein the term introduced includes both transduction and transfection methods. Transfection is the process of introducing nucleic acids into a cell by non-viral methods. Transduction is the process of introducing foreign DNA into a cell via a viral vector.

As used herein, the terms "polynucleotide" and "nucleic acid" are intended to be synonymous with each other. The nucleic acid sequence may be any suitable type of nucleotide sequence, such as a synthetic RNA/DNA sequence, a cDNA sequence or a partial genomic DNA sequence.

The term "polypeptide" as used herein is used in the normal sense to mean a series of residues, typically L-amino acids, connected one to the other typically by peptide bonds between the α-amino and carboxyl groups of adjacent amino acids. The term is synonymous with "protein".

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The polynucleotide may be in isolated or recombinant form. It may be incorporated into a vector and the vector may be incorporated into a host cell. Such vectors and suitable hosts form yet further aspects of the present invention.

The polynucleotide may be double or single stranded, and may be RNA or DNA.

The polynucleotide may be codon optimised. Different cells differ in their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression. Suitably the polynucleotide may be codon optimised for expression in a murine model of disease. Suitably, the polynucleotide may be codon optimised for expression in a human subject.

Many viruses, including HIV and other lentiviruses, use a large number of rare codons and by changing these to correspond to commonly used mammalian codons, increased expression of the packaging components in mammalian producer cells can be achieved. Codon usage tables are known in the art for mammalian cells, as well as for a variety of other organisms.

Codon optimisation may also involve the removal of mRNA instability motifs and cryptic splice sites.

The polynucleotide may comprise a nucleic acid sequence which enables both a nucleic acid sequence encoding an α chain and a nucleic acid sequence a β chain to be expressed from the same mRNA transcript.

For example, the polynucleotide may comprise an internal ribosome entry site (IRES) between the nucleic acid sequences which encode the α chain and the β chain. An IRES is a nucleotide sequence that allows for translation initiation in the middle of a mRNA sequence.

The polynucleotide may comprise a nucleic acid sequence encoding an α chain and a nucleic acid sequence a β chain linked by an internal self-cleaving sequence.

The internal self-cleaving sequence may be any sequence which enables the polypeptide comprising the α chain and the polypeptide comprising the β chain to become separated.

The cleavage site may be self-cleaving, such that when the polypeptide is produced, it is immediately cleaved into individual peptides without the need for any external cleavage activity.

The term "cleavage" is used herein for convenience, but the cleavage site may cause the peptides to separate into individual entities by a mechanism other than classical cleavage. For example, for the Foot-and-Mouth disease virus (FMDV) 2A self-cleaving peptide, various models have been proposed for to account for the "cleavage" activity: proteolysis by a host-cell proteinase, autoproteolysis or a translational effect (Donnelly et al (2001) J. Gen. Virol. 82:1027-1041 incorporated herein by reference). The exact mechanism of such "cleavage" is not important for the purposes of the present invention, as long as the cleavage site, when positioned between nucleic acid sequences which encode proteins, causes the proteins to be expressed as separate entities.

The self-cleaving peptide may be a 2A self-cleaving peptide from an aphtho- or a cardiovirus.

A variant can be considered in terms of similarity (i.e. amino acid residues having similar chemical properties/functions), preferably a variant is expressed in terms of sequence identity.

Sequence comparisons can be conducted by eye, or more usually, with the aid of readily available sequence comparison programs. These publicly and commercially available computer programs can calculate sequence identity between two or more sequences.

Sequence identity may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is –12 for a gap and –4 for each extension.

Calculation of maximum % sequence identity therefore firstly requires the production of an optimal alignment, taking into consideration gap penalties. A suitable computer program for carrying out such an alignment is the GCG Wisconsin Bestfit package (University of Wisconsin, U.S.A; Devereux et al., 1984, Nucleic Acids Research 12:387 incorporated herein by reference). Examples of other software than can perform sequence comparisons include, but are not limited to, the BLAST package (see Ausubel et al., 1999 ibid—Chapter 18), FASTA (Atschul et al., 1990, J. Mol. Biol., 403-410 incorporated herein by reference) and the GENEWORKS suite of comparison tools. Both BLAST and FASTA are available for offline and online searching (see Ausubel et al., 1999 ibid, pages 7-58 to 7-60 incorporated herein by reference). However it is preferred to use the GCG Bestfit program.

In one embodiment, the sequence identity is determined across the entirety of the sequence. In one embodiment, the sequence identity is determined across the entirety of the candidate sequence being compared to a sequence recited herein.

Although the final sequence identity can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % sequence identity. The software typically does this as part of the sequence comparison and generates a numerical result.

The term "variant" according to the present invention includes any substitution of, variation of, modification of, replacement of, deletion of or addition of one (or more) amino acids from or to the sequence providing the resultant amino acid sequence retains substantially the same activity as the unmodified sequence. For example, conservative amino acid substitutions may be made. As used herein, a variant polypeptide is taken to include a polypeptide comprising an amino acid sequence which is at least 70, 80, 85, 90, 95, 98 or 99% identical to a sequence shown herein.

In one aspect, the variant maintains the function of the parent sequence.

FOXP3

In one aspect, a cell according to the invention comprises a nucleotide sequence which encodes a FOXP3 protein that has also been introduced to the cell.

In one aspect, the cell, engineered Treg or pharmaceutical composition of the present invention may comprise an engineered nucleic acid sequence which encodes a FOXP3 protein, in other words the engineered nucleic acid sequence is not part of the endogenous genome of the cell.

FOXP3 is a member of the FOX protein family of transcription factors and functions as a master regulator of the regulatory pathway in the development and function of regulatory T cells.

Suitably, the FOXP3 polypeptide is from a human e.g. the UniProtKB accession: Q9BZS1:

```
                                          (SEQ ID NO: 18)
MPNPRPGKPSAPSLALGPSPGASPSWRAAPKASDLLGARGPGGTFQGRD

LRGGAHASSSSLNPMPPSQLQLPTLPLVMVAPSGARLGPLPHLQALLQD

RPHFMHQLSTVDAHARTPVLQVHPLESPAMISLTPPTTATGVFSLKARP

GLPPGINVASLEWVSREPALLCTFPNPSAPRKDSTLSAVPQSSYPLLAN

GVCKWPGCEKVFEEPEDFLKHCQADHLLDEKGRAQCLLQREMVQSLEQQ

LVLEKEKLSAMQAHLAGKMALTKASSVASSDKGSCCIVAAGSQGPVPAW

SGPREAPDSLFAVRRHLWGSHGNSTFPEFLHNMDYFKFHNMRPPFTYAT

LIRWAILEAPEKQRTLNEIYHWFTRMFAFFRNHPATWKNAIRHNLSLHK

CFVRVESEKGAVWTVDELEFRKKRSQRPSRCSNPTPGP
```

Suitably, the FOXP3 polypeptide comprises an amino acid sequence set forth in SEQ ID NO: 18, or a fragment thereof. Suitably the FOXP3 polypeptide comprises an amino acid sequence which is at least 80% identical to SEQ ID NO: 18 or a fragment thereof. Suitably, the polypeptide comprises an amino acid sequence which is 85, 90, 95, 98 or 99% identical to SEQ ID NO: 18 or a fragment thereof. Suitably the fragment retains FOXP3 activity. Suitably the fragment is able to bind to FOXP3 targets and act as a transcription factor.

Suitably, the FOXP3 polypeptide may be a natural variant of SEQ ID NO: 18. Suitably, the FOXP3 polypeptide is an isoform of SEQ ID NO: 18. For example, the FOXP3 polypeptide may comprise a deletion of amino acid positions 72-106 relative to SEQ ID NO: 18. Alternatively, the FOXP3 polypeptide may comprise a deletion of amino acid positions 246-272 relative to SEQ ID NO: 18.

Suitably, the FOXP3 polypeptide comprises the amino acid sequence set forth in SEQ ID NO: 19:

```
                                        (SEQ ID NO: 19)
MPNPRPGKPSAPSLALGPSPGASPSWRAAPKASDLLGARGPGGTFQGRD

LRGGAHASSSSLNPMPPSQLQLPTLPLVMVAPSGARLGPLPHLQALLQD

RPHFMHQLSTVDAHARTPVLQVHPLESPAMISLTPPTTATGVFSLKARP

GLPPGINVASLEWVSREPALLCTFPNPSAPRKDSTLSAVPQSSYPLLAN

GVCKWPGCEKVFEEPEDFLKHCQADHLLDEKGRAQCLLQREMVQSLEQV
```

-continued
```
EELSAMQAHLAGKMALTKASSVASSDKGSCCIVAAGSQGPVVPAWSGPR

EAPDSLFAVRRHLWGSHGNSTFPEFLHNMDYFKFHNMRPPFTYATLIRW

AILEAPEKQRTLNEIYHWFTRMFAFFRNHPATWKNAIRHNLSLHKCFVR

VESEKGAVWTVDELEFRKKRSQRPSRCSNPTPGPEGRGSLLTCGDVEE

N.
```

Suitably, the FOXP3 polypeptide comprises an amino acid sequence set forth in SEQ ID NO: 19, or a fragment thereof. Suitably the FOXP3 polypeptide comprises an amino acid sequence which is at least 80% identical to SEQ ID NO: 19 or a fragment thereof. Suitably, the polypeptide comprises an amino acid sequence which is 85, 90, 95, 98 or 99% identical to SEQ ID NO: 19 or a fragment thereof. Suitably the fragment retains FOXP3 activity. Suitably the fragment is able to bind to FOXP3 targets and act as a transcription factor.

Suitably, the FOXP3 polypeptide may be a natural variant of SEQ ID NO: 19. Suitably, the FOXP3 polypeptide is an isoform of SEQ ID NO: 19. For example, the FOXP3 polypeptide may comprise a deletion of amino acid positions 72-106 relative to SEQ ID NO: 9. Alternatively, the FOXP3 polypeptide may comprise a deletion of amino acid positions 246-272 relative to SEQ ID NO: 19.

Suitably, the FOXP3 polypeptide is encoded by the polynucleotide sequence set forth in SEQ ID NO: 20:

```
                                        (SEQ ID NO: 20)
ATGCCCAACCCCAGGCCTGGCAAGCCCTCGGCCCCTTCCTTGGCCCTTGGCCCATCCCCA

GGAGCCTCGCCCAGCTGGAGGGCTGCACCCAAAGCCTCAGACCTGCTGGGGGCCCGGG

GCCCAGGGGGAACCTTCCAGGGCCGAGATCTTCGAGGCGGGGCCCATGCCTCCTCTTCT

TCCTTGAACCCCATGCCACCATCGCAGCTGCAGCTGCCCACACTGCCCCTAGTCATGGTG

GCACCCTCCGGGGCACGGCTGGGCCCCTTGCCCCACTTACAGGCACTCCTCCAGGACAG

GCCACATTTCATGCACCAGCTCTCAACGGTGGATGCCCACGCCCGGACCCCTGTGCTGCA

GGTGCACCCCCTGGAGAGCCCAGCCATGATCAGCCTCACACCCACCCACCACCGCCACTG

GGGTCTTCTCCCTCAAGGCCCGGCCTGGCCTCCCACCTGGGATCAACGTGGCCAGCCTG

GAATGGGTGTCCAGGGAGCCGGCACTGCTCTGCACCTTCCCAAATCCCAGTGCACCCAGG

AAGGACAGCACCCTTTCGGCTGTGCCCCAGAGCTCCTACCCACTGCTGGCAAATGGTGTC

TGCAAGTGGCCCGGATGTGAGAAGGTCTTCGAAGAGCCAGAGGACTTCCTCAAGCACTGC

CAGGCGGACCATCTTCTGGATGAGAAGGGCAGGGCACAATGTCTCCTCCAGAGAGAGATG

GTACAGTCTCTGGAGCAGCAGCTGGTGCTGGAGAAGGAGAAGCTGAGTGCCATGCAGGC

CCACCTGGCTGGGAAAATGGCACTGACCAAGGCTTCATCTGTGGCATCATCCGACAAGGG

CTCCTGCTGCATCGTAGCTGCTGGCAGCCAAGGCCCTGTCGTCCCAGCCTGGTCTGGCCC

CCGGGAGGCCCCTGACAGCCTGTTTGCTGTCCGGAGGCACCTGTGGGGTAGCCATGGAA

ACAGCACATTCCCAGAGTTCCTCCACAACATGGACTACTTCAAGTTCCACAACATGCGACC

CCCTTTCACCTACGCCACGCTCATCCGCTGGGCCATCCTGGAGGCTCCAGAGAAGCAGCG

GACACTCAATGAGATCTACCACTGGTTCACACGCATGTTTGCCTTCTTCAGAAACCATCCT

GCCACCTGGAAGAACGCCATCCGCCACAACCTGAGTCTGCACAAGTGCTTTGTGCGGGTG

GAGAGCGAGAAGGGGGCTGTGTGGACCGTGGATGAGCTGGAGTTCCGCAAGAAACGGAG

CCAGAGGCCCAGCAGGTGTTCCAACCCTACACCTGGCCCCTGA
```

In some embodiments of the invention, the polynucleotide encoding the FOXP3 polypeptide or variant comprises a polynucleotide sequence which is at least 80% identical to SEQ ID NO: 20 or a functional fragment thereof. Suitably, the polynucleotide encoding the FOXP3 polypeptide or variant comprises a polynucleotide sequence which is at least 85, 90, 95, 98 or 99% identical to SEQ ID NO: 20 or a functional fragment thereof. In some embodiments of the invention, the polynucleotide encoding the FOXP3 polypeptide or variant comprises SEQ ID NO: 20 or a functional fragment thereof.

Suitably, the FOXP3 polypeptide is encoded by the nucleic acid sequence set forth in SEQ ID NO: 21:

(SEQ ID NO: 21)

```
GAATTCGTCGACATGCCCAACCCCAGACCCGGCAAGCCTTCTGCCCCTTCTCTGGCCCTG

GGACCATCTCCTGGCGCCTCCCCATCTTGGAGAGCCGCCCCTAAAGCCAGCGATCTGCTG

GGAGCTAGAGGCCCTGGCGGCACATTCCAGGGCAGAGATCTGAGAGGCGGAGCCCACGC

CTCTAGCAGCAGCCTGAATCCCATGCCCCCTAGCCAGCTGCAGCTGCCTACACTGCCTCT

CGTGATGGTGGCCCCTAGCGGAGCTAGACTGGGCCCTCTGCCTCATCTGCAGGCTCTGCT

GCAGGACCGGCCCCACTTTATGCACCAGCTGAGCACCGTGGACGCCCACGCCAGAACAC

CTGTGCTGCAGGTGCACCCCCTGGAAAGCCCTGCCATGATCAGCCTGACCCCTCCAACCA

CAGCCACCGGCGTGTTCAGCCTGAAGGCCAGACCTGGACTGCCCCCTGGCATCAATGTG

GCCAGCCTGGAATGGGTGTCCCGCGAACCTGCCCTGCTGTGCACCTTCCCCAATCCTAGC

GCCCCCAGAAAGGACAGCACACTGTCTGCCGTGCCCCAGAGCAGCTATCCCCTGCTGGCT

AACGGCGTGTGCAAGTGGCCTGGCTGCGAGAAGGTGTTCGAGGAACCCGAGGACTTCCT

GAAGCACTGCCAGGCCGACCATCTGCTGGACGAGAAAGGCAGAGCCCAGTGCCTGCTGC

AGCGCGAGATGGTGCAGTCCCTGGAACAGCAGCTGGTGCTGGAAAAAGAAAAGCTGAGC

GCCATGCAGGCCCACCTGGCCGGAAAGATGGCCCTGACAAAAGCCAGCAGCGTGGCCAG

CTCCGACAAGGGCAGCTGTTGTATCGTGGCCGCTGGCAGCCAGGGACCTGTGGTGCCTG

CTTGGAGCGGACCTAGAGAGGCCCCCGATAGCCTGTTTGCCGTGCGGAGACACCTGTGG

GGCAGCCACGGCAACTCTACCTTCCCCGAGTTCCTGCACAACATGGACTACTTCAAGTTCC

ACAACATGAGGCCCCCCTTCACCTACGCCACCCTGATCAGATGGGCCATTCTGGAAGCCC

CCGAGAAGCAGCGGACCCTGAACGAGATCTACCACTGGTTTACCCGGATGTTCGCCTTCT

TCCGGAACCACCCCGCCACCTGGAAGAACGCCATCCGGCACAATCTGAGCCTGCACAAGT

GCTTCGTGCGGGTGGAAAGCGAGAAGGGCGCCGTGTGGACAGTGGACGAGCTGGAATTT

CGGAAGAAGCGGTCCCAGAGGCCCAGCCGGTGTAGCAATCCTACACCTGGCCCTGAGGG

CAGAGGAAGTCTGCTAACATGCGGTGACGTCGAGGAGAATCC.
```

Suitably, the FOXP3 polypeptide is encoded by the nucleic acid sequence set forth in SEQ ID NO: 21, or a fragment thereof. Suitably the FOXP3 polypeptide is encoded by a nucleic acid sequence which is at least 80% identical to SEQ ID NO: 21 or a fragment thereof. Suitably, the FOXP3 polypeptide is encoded by the nucleic acid sequence which is 85, 90, 95, 98 or 99% identical to SEQ ID NO: 21 or a fragment thereof. Suitably the fragment retains FOXP3 activity. Suitably the polypeptide encoded by the fragment is able to bind to FOXP3 targets and act as a transcription factor.

The nucleic acid encoding the TCR and/or FOXP3 may comprise a leader sequence upstream of the initiation codon. This sequence may regulate translation of a transcript. By way of example, suitable leader sequences for use in the present invention are: MEKMLECAFIVLWLQLGWLSG (SEQ ID NO: 22) and MLCSLLALLLGTFFGVR (SEQ ID NO: 23).

In a further aspect the present invention provides a kit of nucleic acid sequences comprising: a first nucleic acid sequence which encodes a TCR as defined herein and a second nucleic acid which encodes FOXP3.

VECTOR

The present invention also provides a vector comprising a nucleotide sequence encoding a TCR as described herein.

Suitably, the vector may additionally comprise a nucleotide sequence encoding a forkhead box P3 (FOXP3) polypeptide. In one aspect, there is provided a kit of vectors which comprises one or more nucleic acid sequence(s) of the invention such as a nucleic acid encoding a TCR as defined herein and a nucleic acid encoding FOXP3.

The term "vector" includes an expression vector, i.e., a construct enabling expression of TCR i.e. an α chain and/or β chain according to the present invention. Suitably the expression vector additionally enables expression of a FOXP3 polypeptide. In some embodiments, the vector is a cloning vector.

Where the vector comprises a polynucleotide encoding a TCR in addition to a polynucleotide encoding FOXP3; the vector may have the orientation of: 5' FOXP3-TCR 3'. Accordingly the polynucleotide encoding a FOXP3 may be 5' to the polynucleotide encoding TCR.

Suitably, the polynucleotide encoding FOXP3 may be separated from the polynucleotide encoding a TCR by a nucleic acid sequence which enables both the nucleic acid sequence encoding FOXP3 and the nucleic acid sequence encoding the TCR to be expressed from the same mRNA transcript.

For example, the polynucleotide may comprise an internal ribosome entry site (IRES) between the nucleic acid sequences which encode (i) FOXP3 and (ii) the TCR. An IRES is a nucleotide sequence that allows for translation initiation in the middle of a mRNA sequence.

The polynucleotide may comprise a nucleic acid sequence encoding (i) FOXP3 and (ii) the TCR linked by an internal self-cleaving sequence. The polynucleotides encoding the TCR α and β chains may also be separated by an internal self-cleaving sequence.

Suitably, the vector may have the structure: 5' Strong promoter (e.g. LTR)-FoxP3-2A-TCR-3'LTR. Here, FOXP3 expression is directly driven by the strong LTR promoter for optimal expression. TCR is preceded by a 2A sequence and expression of the TCR is thus dependent on both LTR promoter activity and 2A cleavage activity. Importantly, a configuration in which FOXP3 precedes TCR in the 5' to 3' direction ensures that TCR expression can only occur when FOXP3 has been expressed and that expression of TCR without FOXP3 does not occur. This is a particular advantage in the present context of an engineered Treg, as it reduces the risk of an engineered Treg acquiring an effector phenotype and/or reduces the risk associated with introducing the TCR into a T effector cell present in a starting population.

The cleaving sequence may be any sequence which enables the polypeptide comprising (i) FOXP3 and (ii) the TCR to become separated.

The cleavage site may be self-cleaving, such that when the polypeptide is produced, it is immediately cleaved into individual peptides without the need for any external cleavage activity.

The term "cleavage" is used herein for convenience, but the cleavage site may cause the peptides to separate into individual entities by a mechanism other than classical cleavage. For example, for the Foot-and-Mouth disease virus (FMDV) 2A self-cleaving peptide, various models have been proposed for to account for the "cleavage" activity: proteolysis by a host-cell proteinase, autoproteolysis or a translational effect (Donnelly et al (2001) J. Gen. Virol. 82:1027-1041 incorporated herein by reference). The exact mechanism of such "cleavage" is not important for the purposes of the present invention, as long as the cleavage site, when positioned between nucleic acid sequences which encode proteins, causes the proteins to be expressed as separate entities.

The self-cleaving peptide may be a 2A self-cleaving peptide from an aphtho- or a cardiovirus.

A variant can be considered in terms of similarity (i.e. amino acid residues having similar chemical properties/ functions), preferably a variant is expressed in terms of sequence identity.

Sequence comparisons can be conducted by eye, or more usually, with the aid of readily available sequence comparison programs. These publicly and commercially available computer programs can calculate sequence identity between two or more sequences.

Suitably, the FOXP3 polypeptide expressed from the present vector may be positioned at the N-terminal of a self-cleaving peptide, for example a 2A self-cleaving peptide. Such a FOXP3-2A polypeptide may comprise a sequence shown as SEQ ID NO: 24 or 25; or a variant of SEQ ID NO: 24 or 25 which is at least 80% identical thereto. Suitably, the variant may be at least 85, 90, 95, 98 or 99% identical to SEQ ID NO: 24 or 25.

```
                                  SEQ ID NO: 24
MPNPRPGKPSAPSLALGPSPGASPSWRAAPKASDLLGARGPGGTFQGRD

LRGGAHASSSSLNPMPPSQLQLPTLPLVMVAPSGARLGPLPHLQALLQD
```

```
-continued
RPHFMHQLSTVDAHARTPVLQVHPLESPAMISLTPPTTATGVFSLKARP

GLPPGINVASLEWVSREPALLCTFPNPSAPRKDSTLSAVPQSSYPLLAN

GVCKWPGCEKVFEEPEDFLKHCQADHLLDEKGRAQCLLQREMVQSLEQQ

LVLEKEKLSAMQAHLAGKMALTKASSVASSDKGSCCIVAAGSQGPVVPA

WSGPREAPDSLFAVRRHLWGSHGNSTFPEFLHNMDYFKFHNMRPPFTYA

TLIRWAILEAPEKQRTLNEIYHWFTRMFAFFRNHPATWKNAIRHNLSLH

KCFVRVESEKGAVWTVDELEFRKKRSQRPSRCSNPTPGPGATNFSLLKQ

AGDVEENPGPS

SEQ ID NO: 25
MPNPRPGKPSAPSLALGPSPGASPSWRAAPKASDLLGARGPGGTFQGRD

LRGGAHASSSSLNPMPPSQLQLPTLPLVMVAPSGARLGPLPHLQALLQD

RPHFMHQLSTVDAHARTPVLQVHPLESPAMISLTPPTTATGVFSLKARP

GLPPGINVASLEWVSREPALLCTFPNPSAPRKDSTLSAVPQSSYPLLAN

GVCKWPGCEKVFEEPEDFLKHCQADHLLDEKGRAQCLLQREMVQSLEQV

EELSAMQAHLAGKMALTKASSVASSDKGSCCIVAAGSQGPWPAWSGPRE

APDSLFAVRRHLWGSHGNSTFPEFLHNMDYFKFHNMRPPFTYATLIRWA

ILEAPEKQRTLNEIYHWFTRMFAFFRNHPATWKNAIRHNLSLHKCFVRV

ESEKGAVWTVDELEFRKKRSQRPSRCSNPTPGPEGRGSLLTCGDVEENG

ATNFSLLKQAGDVEENPGPS
```

Suitable vectors may include, but are not limited to, plasmids, viral vectors, transposons, nucleic acid complexed with polypeptide or immobilised onto a solid phase particle.

Viral delivery systems include but are not limited to adenovirus vector, an adeno-associated viral (AAV) vector, a herpes viral vector, retroviral vector, lentiviral vector, baculoviral vector.

Retroviruses are RNA viruses with a life cycle different to that of lytic viruses. In this regard, a retrovirus is an infectious entity that replicates through a DNA intermediate. When a retrovirus infects a cell, its genome is converted to a DNA form by a reverse transcriptase enzyme. The DNA copy serves as a template for the production of new RNA genomes and virally encoded proteins necessary for the assembly of infectious viral particles.

There are many retroviruses, for example murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) and all other retroviridiae including lentiviruses.

A detailed list of retroviruses may be found in Coffin et al ("Retroviruses" 1997 Cold Spring Harbour Laboratory Press Eds: J M Coffin, S M Hughes, H E Varmus pp 758-763) incorporated herein by reference.

Lentiviruses also belong to the retrovirus family, but they can infect both dividing and non-dividing cells (Lewis et al (1992) EMBO J. 3053-3058) incorporated herein by reference.

The vector may be capable of transferring a polynucleotide the invention to a cell, for example a host cell as defined herein. The vector should ideally be capable of sustained high-level expression in host cells, so that the α chain and/or β chain are suitably expressed in the host cell.

The vector may be a retroviral vector. The vector may be based on or derivable from the MP71 vector backbone. The vector may lack a full-length or truncated version of the Woodchuck Hepatitis Response Element (WPRE).

For efficient infection of human cells, viral particles may be packaged with amphotropic envelopes or gibbon ape leukemia virus envelopes.

Cell

The present invention further provides a cell e.g. a host cell comprising a polynucleotide or vector according to the invention.

The host cell may be any cell which can be used to express and produce a TCR.

Suitably, the cell is a T cell, such as a conventional T cell.

Suitably, the cell is a Treg cell.

In one aspect, the cell, such as a T cell or Treg, may be isolated from blood obtained from the subject. Suitably, the cell, such as a T cell or Treg, is isolated from peripheral blood mononuclear cells (PBMCs) obtained from the subject.

Suitably, the cell is a natural T reg which expresses FOXP3.

In one aspect, the cell is a stem cell.

In another aspect, the cell is a progenitor cell.

As used herein, the term "stem cell" means an undifferentiated cell which is capable of indefinitely giving rise to more stem cells of the same type, and from which other, specialised cells may arise by differentiation. Stem cells are multipotent. Stem cells may be for example, embryonic stem cells or adult stem cells.

As used herein, the term "progenitor cell" means a cell which is able to differentiate to form one or more types of cells but has limited self-renewal in vitro.

Suitably, the cell is capable of being differentiated into a T cell, such as a Treg.

Suitably, the cell has the ability to differentiate into a T cell, which expresses FOXP3 such as a Treg.

Suitably, the cell is a human cell. Suitable the cell is a human Treg.

Suitably, the cell may be an embryonic stem cell (ESC). Suitably, the cell is a haematopoietic stem cell or haematopoietic progenitor cell. Suitably, the cell is an induced pluripotent stem cell (iPSC). Suitably, the cell may be obtained from umbilical cord blood. Suitably, the cell may be obtained from adult peripheral blood.

In some aspects, hematopoietic stem and progenitor cell (HSPCs) may be obtained from umbilical cord blood. Cord blood can be harvested according to techniques known in the art (e.g., U.S. Pat. Nos. 7,147,626 and 7,131,958 which are incorporated herein by reference).

In one aspect, HSPCs may be obtained from pluripotent stem cell sources, e.g., induced pluripotent stem cells (iPSCs) and embryonic stem cells (ESCs).

As used herein, the term "hematopoietic stem and progenitor cell" or "HSPC" refers to a cell which expresses the antigenic marker CD34 (CD34+) and populations of such cells. In particular embodiments, the term "HSPC" refers to a cell identified by the presence of the antigenic marker CD34 (CD34+) and the absence of lineage (lin) markers. The population of cells comprising CD34+ and/or Lin(−) cells includes haematopoietic stem cells and hematopoietic progenitor cells.

HSPCs can be obtained or isolated from bone marrow of adults, which includes femurs, hip, ribs, sternum, and other bones. Bone marrow aspirates containing HSPCs can be obtained or isolated directly from the hip using a needle and syringe. Other sources of HSPCs include umbilical cord blood, placental blood, mobilized peripheral blood, Wharton's jelly, placenta, fetal blood, fetal liver, or fetal spleen. In particular embodiments, harvesting a sufficient quantity of HSPCs for use in therapeutic applications may require mobilizing the stem and progenitor cells in the subject.

As used herein, the term "induced pluripotent stem cell" or "iPSC" refers to a non-pluripotent cell that has been reprogrammed to a pluripotent state. Once the cells of a subject have been reprogrammed to a pluripotent state, the cells can then be programmed to a desired cell type, such as a hematopoietic stem or progenitor cell (HSC and HPC respectively).

As used herein, the term "reprogramming" refers to a method of increasing the potency of a cell to a less differentiated state.

As used herein, the term "programming" refers to a method of decreasing the potency of a cell or differentiating the cell to a more differentiated state.

Suitably the cell is matched or is autologous to the subject. The cell may be generated ex vivo either from a patient's own peripheral blood (1st party), or in the setting of a haematopoietic stem cell transplant from donor peripheral blood (2nd party), or peripheral blood from an unconnected donor (3rd party).

Suitably the cell is autologous to the subject. Suitably, the subject is a human.

In some aspects, the cell may be derived from ex-vivo differentiation of inducible progenitor cells or embryonic progenitor cells to the immune cell. In these instances, cells are generated by introducing DNA or RNA coding for the TCR of the present invention by one of many means including transduction with a viral vector, transfection with DNA or RNA.

Suitably, the cells are generated by introducing in addition to the TCR of the invention, DNA or RNA coding for FOXP3 by one of many means including transduction with a viral vector, or transfection with DNA or RNA.

As used herein, the term "conventional T cell" or Tconv means a T lymphocyte cell which expresses an αβ T cell receptor (TCR) as well as a co-receptor which may be cluster of differentiation 4) CD4 or cluster of differentiation 8 (CD8). Conventional T cells are present in the peripheral blood, lymph nodes, and tissues. FOXP3 is expressed by thymus derived Tregs and can be expressed by recently activated conventional T cells.

As used herein, the term "regulatory T cell" or Treg, means a T cell which expresses the markers CD4, CD25 and FOXP3 (CD4$^+$CD25$^+$FOXP3$^+$). Tregs may also be identified using the cell surface markers CD4 and CD25 in the absence of or in combination with low-level expression of the surface protein CD127 (CD4$^+$CD25$^+$CD127$^-$). Tregs may also express on the cell surface, high levels of CTLA-4 (cytotoxic T-lymphocyte associated molecule-4) or GITR (glucocorticoid-induced TNF receptor). Unlike conventional T cells, regulatory T cells do not produce IL-2 and are therefore anergic at baseline. Treg cells include thymus-derived, natural Treg (nTreg) cells and peripherally generated, induced Treg (iTreg) cells.

In one aspect, a Treg is CD4$^+$CD25$^+$FOXP3$^+$. T cell.

In one aspect, a Treg is a CD4$^+$CD25$^+$CD127$^-$ T cell.

In one aspect, a Treg is a CD4$^+$CD25$^+$FOXP3$^+$CD127$^-$ T cell.

As used herein, the term "natural T reg" means a thymus-derived Treg. Natural T regs are CD4$^+$CD25$^+$FOXP3$^+$ Helios$^+$ Neuropilin 1$^+$. Compared with iTregs, nTregs have higher expression of PD-1 (programmed cell death-1, pdcd1), neuropilin 1 (Nrp1), Helios (Ikzf2), and CD73. nTregs may be distinguished from iTregs on the basis of the expression of Helios protein or Neuropilin 1 (Nrp1) individually.

As used herein, the term "induced regulatory T cell" (iTreg) means a CD4$^+$ CD25$^+$ FOXP3$^+$ Helios$^-$ Neuropilin 1$^-$ T cell which develops from mature CD4+ conventional T cells outside of the thymus. For example, iTregs can be induced in vitro from CD4+ CD25−FOXP3− cells in the presence of IL-2 and TGF-β.

The method of the present invention may comprise introducing a first nucleotide sequence encoding the present TCR and a second nucleotide sequence encoding FOXP3 into a natural Treg (which already expresses endogenous FOXP3) as described herein. Suitably, the method of the present invention comprises introducing a vector which comprises a polynucleotide encoding the present TCR in addition to a polynucleotide encoding FOXP3; wherein the vector has the orientation of: 5' FOXP3-TCR 3'—as described herein—into a natural Treg as defined herein. Accordingly the polynucleotide encoding a FOXP3 may be 5' to the polynucleotide encoding TCR. Without wishing to be bound by theory, the present inventors have shown that exogenous FOXP3 expression in regulatory T cell (Tregs) (which already express endogenous FOXP3) enhances their regulatory function. In particular, the present inventors have determined that increasing FOXP3 expression in Tregs which already express endogenous FOXP3 (e.g. by introducing exogenous FOXP3) enhances the regulatory function of the Tregs to a greater degree than the regulatory function provided by expressing exogenous FOXP3 in conventional T cells which do not express endogenous FOXP3. Further, increasing FOXP3 expression in Tregs which already express endogenous FOXP3 enables improved retention of a Treg functional profile in vivo following administration to a subject. For example, it has been determined that natural Tregs which do not express exogenous FOXP3 may lose their Treg profile following administration to a subject—for example natural Tregs which do not express exogenous FOXP may have reduced levels of FOXP3 expression and be capable of producing pro-inflammatory, effector cytokines after a period following administration to a subject. Tregs provided by the present invention may retain FOXP3 expression and have reduced capability to produce pro-inflammatory, effector cytokines after a period following administration to a subject.

Compositions

The present invention also provides a composition comprising an engineered Treg, a vector or a cell according to the invention. Suitably the present invention provides a composition comprising an engineered Treg according to the invention. Suitably the present invention provides a composition comprising a vector according to the invention. Suitably the present invention provides a composition comprising a cell according to the invention.

In some embodiments, the composition is a pharmaceutical composition. Such pharmaceutical composition may comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as (or in addition to) the carrier, excipient or diluent, any suitable binder(s), lubricant(s), suspending agent(s), coating agent(s), solubilising agent(s) and other carrier agents.

The pharmaceutical compositions typically should be sterile and stable under the conditions of manufacture and storage. Formulations for parenteral administration include, but are not limited to, suspensions, solutions, emulsions in oily or aqueous vehicles, pastes, and implantable sustained-release or biodegradable formulations as discussed herein. Sterile injectable formulations may be prepared using a non-toxic parenterally acceptable diluent or solvent. A pharmaceutical composition for use in accordance with the present invention may include pharmaceutically acceptable dispersing agents, wetting agents, suspending agents, isotonic agents, coatings, antibacterial and antifungal agents, carriers, excipients, salts, or stabilizers which are non-toxic to the subjects at the dosages and concentrations employed. Preferably, such a composition can further comprise a pharmaceutically acceptable carrier or excipient for use in the treatment of disease that that is compatible with a given method and/or site of administration, for instance for parenteral (e.g. sub-cutaneous, intradermal, or intravenous injection) or intrathecal administration.

Wherein the pharmaceutical composition comprises a cell according to the invention, the composition may be produced using current good manufacturing practices (cGMP).

Suitably the pharmaceutical composition comprising a cell may comprise an organic solvent, such as but not limited to, methyl acetate, dimethyl sulfoxide (DMSO), N,N-dimethylformamide (DMF), dimethoxyethane (DME), and dimethylacetamide, including mixtures or combinations thereof.

Suitably the pharmaceutical composition comprising a cell is endotoxin free.

Method of Treatment

The present invention provides a method for treating and/or preventing a disease which comprises the step of administering an engineered Treg of the present invention to a subject.

The present invention provides a method for treating and/or preventing a disease which comprises the step of administering a pharmaceutical composition of the present invention to a subject.

The present invention also provides an engineered Treg of the present invention for use in treating and/or preventing a disease.

The present invention also provides a pharmaceutical composition of the present invention for use in treating and/or preventing a disease.

The invention also relates to the use of an engineered Treg, a vector or cell according to the present invention in the manufacture of a medicament for treating and/or preventing a disease.

Preferably, the present methods of treatment relate to the administration of a pharmaceutical composition of the present invention to a subject.

The term "treat/treatment/treating" refers to administering an engineered Treg, cell, vector, or pharmaceutical composition as described herein to a subject having an existing disease or condition in order to lessen, reduce or improve at least one symptom associated with the disease and/or to slow down, reduce or block the progression of the disease.

Reference to "prevention"/"preventing" (or prophylaxis) as used herein refers to delaying or preventing the onset of the symptoms of the disease. Prevention may be absolute (such that no disease occurs) or may be effective only in some individuals or for a limited amount of time.

In a preferred embodiment of the present invention, the subject of any of the methods described herein is a mammal, preferably a cat, dog, horse, donkey, sheep, pig, goat, cow, mouse, rat, rabbit or guinea pig. Preferably the subject is a human.

The administration of a pharmaceutical composition of the invention can be accomplished using any of a variety of routes that make the active ingredient bioavailable. For example, a Treg, cell, vector, or pharmaceutical composition can be administered intravenously, intrathecally, by oral and parenteral routes, intranasally, intraperitoneally, subcutaneously, transcutaneously or intramuscularly.

In one aspect, the engineered Treg according to the invention or the pharmaceutical composition according to the invention is administered intravenously.

In another aspect, the engineered Treg according to the invention or the pharmaceutical composition according to the invention is administered intrathecally.

Typically, a physician will determine the actual dosage that is most suitable for an individual subject and it will vary with the age, weight and response of the particular patient. The dosage is such that it is sufficient to reduce and/or prevent disease symptoms.

Those skilled in the art will appreciate, for example, that route of delivery (e.g., oral vs intravenous vs subcutaneous, etc) may impact dose amount and/or required dose amount may impact route of delivery. For example, where particularly high concentrations of an agent within a particular site or location are of interest, focused delivery may be desired and/or useful. Other factors to be considered when optimizing routes and/or dosing schedule for a given therapeutic regimen may include, for example, the disease being treated (e.g., type or stage, etc.), the clinical condition of a subject (e.g., age, overall health, etc.), the presence or absence of combination therapy, and other factors known to medical practitioners.

The dosage is such that it is sufficient to stabilise or improve symptoms of the disease.

The present invention also provides a method for treating and/or preventing a disease, which comprises the step of administering a pharmaceutical composition comprising a cell e.g. a T cell according to the invention to a subject.

Suitably, the present invention also provides a method for treating and/or preventing a disease, which comprises the step of administering an engineered Treg according to the invention to a subject.

The method may comprise the following steps:

(i) isolation of a cell-containing sample from a subject;
(ii) introducing a nucleic acid sequence encoding a TCR and optionally, a nucleic acid encoding a FOXP3 protein to the cells; and
(iii) administering the cells from (ii) to the subject.

Suitably the cells from (ii) may be expanded in vitro before administration to the subject.

The method may comprise the following steps:

(i) introducing a nucleic acid sequence encoding a TCR and optionally, a nucleic acid encoding a FOXP3 protein to a cell-containing sample; and
(ii) administering the cells from (i) to the subject.

Disease

The disease to be treated and/or prevented by the methods and uses of the present invention may be any disease which induces a T cell mediated immune response.

The disease may be, for example, a cancer, infectious disease or autoimmune disease.

Suitably the disease to be treated and/or prevented by the methods and uses of the present invention may be an autoimmune disease.

Without wishing to be bound by theory, the disease to be treated and/or prevented by the methods and uses of the present invention may be any disease wherein MBP is an antigen e.g. where MBP is a self-antigen.

Suitably the disease may be an autoimmune and inflammatory central nervous system disease (e.g. chronic neurodegenerative conditions).

Suitably the disease may be a chronic neurodegenerative condition such as multiple sclerosis (MS), Alzheimer's disease, Parkinson's disease, neurotropic viral infections, stroke, paraneoplastic disorders and traumatic brain injury.

In one aspect, the disease is multiple sclerosis.

Suitably, the disease is chronic progressive multiple sclerosis.

Suitably, the disease is relapsing/remitting multiple sclerosis.

In one aspect, the disease may have central nervous system (CNS) involvement of systemic autoimmune and inflammatory disease such as Behçet disease, sarcoidosis, systemic lupus erythematosus, juvenile idiopathic arthritis, scleroderma, and Sjögren syndrome.

Suitably, the disease is present in an HLA-DRB1*0401 positive subject.

Suitably, the disease is multiple sclerosis and the subject is HLA-DRB1*0401 positive.

Suitably, the disease is chronic progressive multiple sclerosis and the subject is HLA-DRB1*0401 positive.

Suitably, the disease is relapsing/remitting multiple sclerosis and the subject is HLA-DRB1*0401 positive.

Multiple Sclerosis

Multiple Sclerosis (MS) is the most common neurological disorder among young adults in Europe and in the USA. MS is characterised as a demyelinating disease and is a chronic degenerative disease of the central nervous system in which gradual destruction of myelin occurs in patches throughout the brain and/or spinal cord, interfering with neural connectivity and causing muscular weakness, loss of coordination and speech and visual disturbances.

Several types or patterns of progression of MS have been identified including, clinically isolated syndrome (CIS), relapsing-remitting MS (RRMS), primary progressive MS (PPMS) and secondary progressive MS (SPMS). For some patients, the increase or progression of disability is very gradual, and for others it can occur more quickly. In general, however, recovery from attacks become less and less complete, and symptoms tend to increase and disability grows.

Although several disease-modifying treatments (DMTs) have been approved to reduce the frequency of clinical relapses, most patients continue to clinically deteriorate under current therapy schedules. Autologous haematopoietic stem cell transplantation can have lasting beneficial effects for patients, but the procedure requires aggressive myeloablative conditioning which is associated with substantial toxicity. Neither DMTs nor stem cell transplantation can mediate antigen-specific suppression of the immunopathology of MS. Without wishing to be bound by theory, in the future, administration of one dose of engineered Treg of the present invention may provide lasting suppression of MS immunopathology in the absence of systemic side effects. This will have a significant impact on the progression of the disease in people with MS.

Suitably, the Treg, vector or pharmaceutical composition of the present invention may reduce or ameliorate one or more of the symptoms of MS, which include reduced or loss of vision, stumbling and uneven gait, slurred speech, urinary frequency and incontinence, mood changes and depression, muscle spasms and paralysis.

Method

The invention also provides a method for producing an engineered Treg which method comprises introducing into a cell in vitro or ex vivo, a polynucleotide encoding a TCR as defined herein. Suitably, the method further comprises incubating the cell under conditions permitting expression of the TCR molecule of the present invention. Optionally, the method may further comprise a step of purifying the engineered Treg cells.

Suitably, the cell is a T cell.

Suitably, the cell is a Treg cell.

Suitably, the cell is a natural Treg which expresses FOXP3.

In one aspect, the cell is a stem cell. Suitably, in the method according to the invention, a nucleic acid encoding TCR as defined herein has been introduced into the stem cell and the stem cell is then differentiated into a T cell such as a Treg which expresses FOXP3.

Suitably, the stem cell has the ability to differentiate into a T cell such as a Treg which expresses FOXP3. Suitably, the cell may be an embryonic stem cell (ESC). Suitably, the cell may be obtained from umbilical cord blood. Suitably, the cell may be obtained from adult peripheral blood. Suitably, the cell is a haematopoietic stem and progenitor cell (HSPC). Suitably, the cell is an induced pluripotent stem cell (iPSC).

In another aspect, the cell is a progenitor cell. Suitably the progenitor cell has the ability to differentiate into a T cell such as a Treg which expresses FOXP3.

In another aspect, the invention provides a method for producing an engineered Treg, which method comprises introducing into a cell in vitro or ex vivo a polynucleotide encoding a TCR as defined herein and a polynucleotide encoding a FOXP3 protein. Suitably, the cell may be a natural Treg as defined herein. Suitably the polynucleotide encoding a TCR as defined herein and the polynucleotide encoding a FOXP3 protein are provided as separate polynucleotides. Suitably the separate polypeptides are introduced separately, sequentially or simultaneously into the cell. Wherein the polypeptides are introduced separately or sequentially, suitably the polynucleotide encoding the TCR is introduced first. Wherein the polypeptides are introduced separately or sequentially, suitably the polynucleotide encoding FOXP3 is introduced first. Suitably the polynucleotide encoding a TCR as defined herein and the polynucleotide encoding a FOXP3 protein are provided on the same polynucleotide.

In some embodiments, the method according to the invention comprises:

(a) isolating a natural Treg from a cell population; and (b) increasing FOXP3 expression in the natural Treg.

The expression "isolating the Treg from a cell population" means to separate out the Treg from a heterogeneous mixture of multiple different types of cells. Suitable the cell population is from a sample from a human subject.

Suitably, the Treg is isolated as a population of Tregs.

Suitably, the population of Tregs comprises at least 70% Tregs, such as 75%, 85%, 90% or 95% Tregs.

Suitably, the method further comprises incubating the cell under conditions causing expression of FOXP3 and the TCR molecule of the present invention. Optionally, the method may further comprise a step of purifying the engineered Treg cells.

In one aspect, the invention provides a method for producing an engineered Treg, which method comprises introducing into a cell in vitro or ex vivo a polynucleotide encoding a TCR as defined herein and a polynucleotide encoding a FOXP3 protein and differentiating the cell into a T cell, such as a Treg which expresses FOXP3. Suitably, the method further comprises incubating the cell under conditions causing expression of FOXP3 and the TCR molecule of the present invention. Optionally, the method may further comprise a step of purifying the engineered Treg cells.

Suitably, in one aspect the cell is differentiated into a T cell before FOXP3 is introduced into the cell.

Purification of the engineered Treg may be achieved by any method known in the art. Suitably, the engineered Treg may be purified using fluorescence-activated cell sorting (FACS) or immunomagnetic isolation (i.e. using antibodies attached to magnetic nanoparticles or beads) using positive and/or negative selection of cell populations.

Suitably, purification of the engineered T cell may be performed using the expression of the TCR as defined herein.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

It is noted that embodiments of the invention as described herein may be combined.

The publications discussed herein are provided solely for their disclosure prior to the filing date of the present application. Nothing herein is to be construed as an admission that such publications constitute prior art to the claims appended hereto.

The invention will now be further described by way of Examples, which are meant to serve to assist one of ordinary skill in the art in carrying out the invention and are not intended in any way to limit the scope of the invention.

EXAMPLES

Example 1—Production of Retroviral Vectors Encoding TCR and TCR+FOXP3

MS2-3C8 TCR

Figure 1:
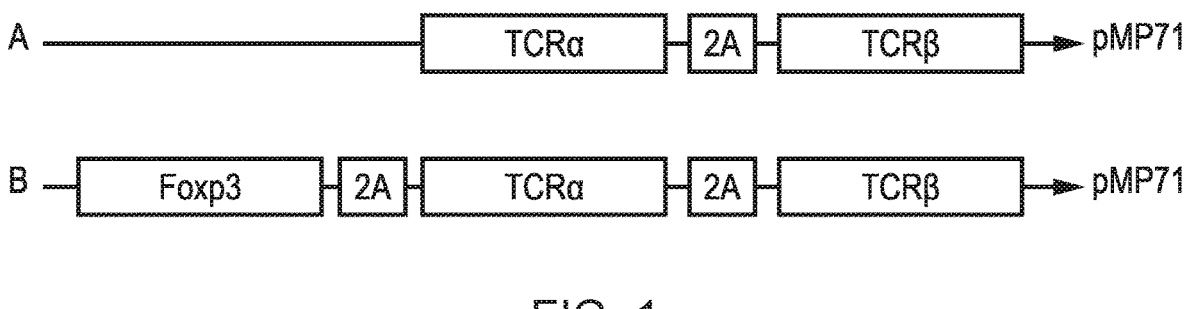
FIG. 1—shows a schematic diagram of a pMP71 retroviral vector encoding (A) MBP TCR alpha and beta chains and (B) FOXP3 plus TCR alpha and beta chains.
Figure 2:
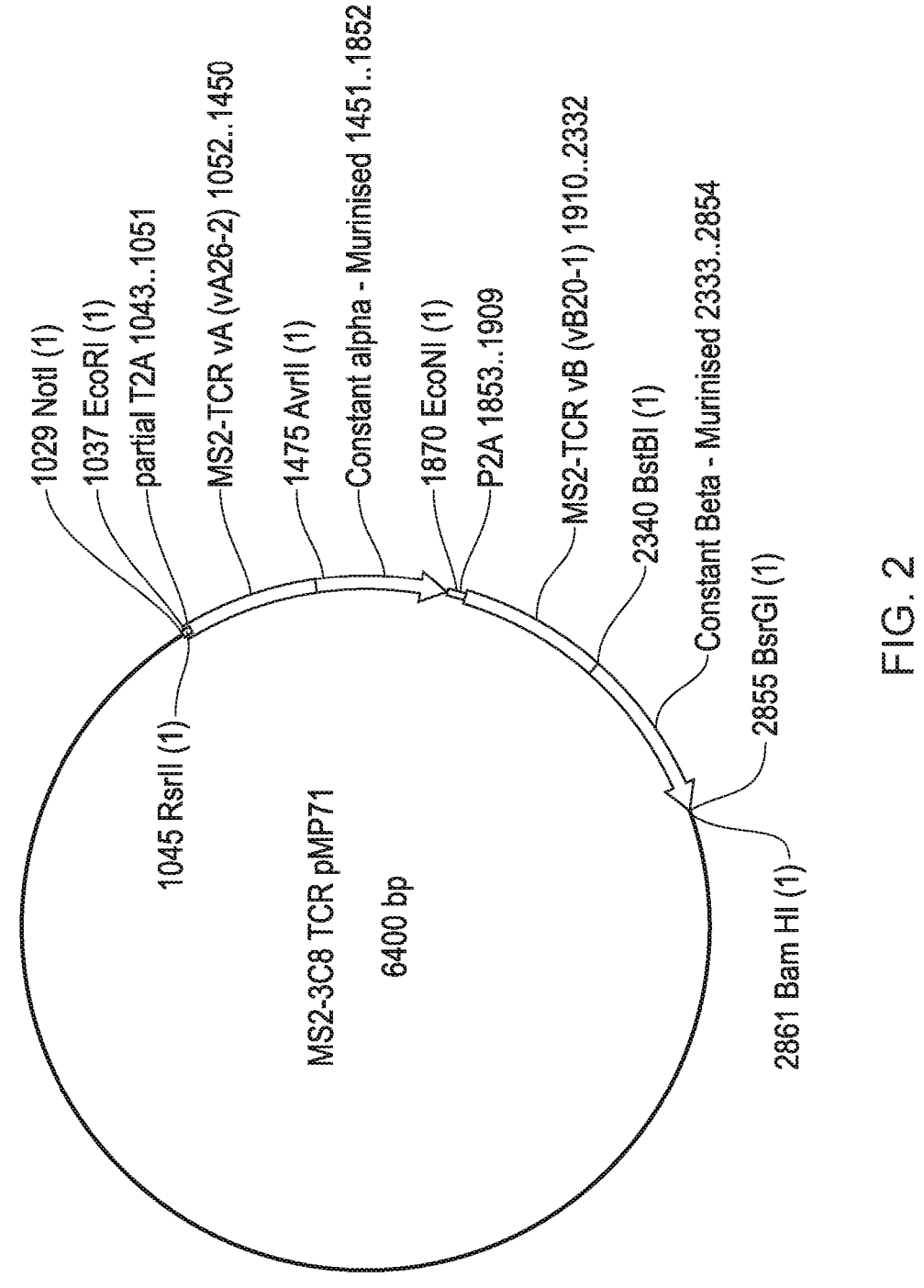
FIG. 2—MS2-3C8 TCR pMP71. MS2-3C8 TCR recognises MBP 111-129 (SEQ ID NO: 12) presented by HLA-DRB1*0401. The TCR has been codon optimised and both constant alpha and beta domains have been murinised, and an extra disulphide bond has been added between c-alpha and c-beta.

The MS2-3C8 TCR recognises MBP 111-129 (SEQ ID NO: 12) presented by HLA-DRB1*0401 as described by Muraro et al., JCI 1997; 100, 2, 339-349, incorporated herein by reference. A codon optimised MS-2 TCR expression cassette coding for the MS2-3C8 TCR was constructed (FIG. 1 and FIG. 2) by cloning the codon optimised MS2-TCR vα, murinised constant alpha domain, codon optimised MS2-TCR vβ and murinised constant beta domain into a retroviral expression cassette, pMP71. An extra disulphide bond was added between the constant-alpha and constant-beta domains as described in Blood. 2007 Mar. 15; 109(6): 2331-2338. and Cancer Res. 2007 Apr. 15; 67(8): 3898-3903, incorporated herein by reference. The constant-alpha and MS2-TCR vβ domains were separated by a P2A sequence.

MS2-3C8 FOXP3

Figure 3:
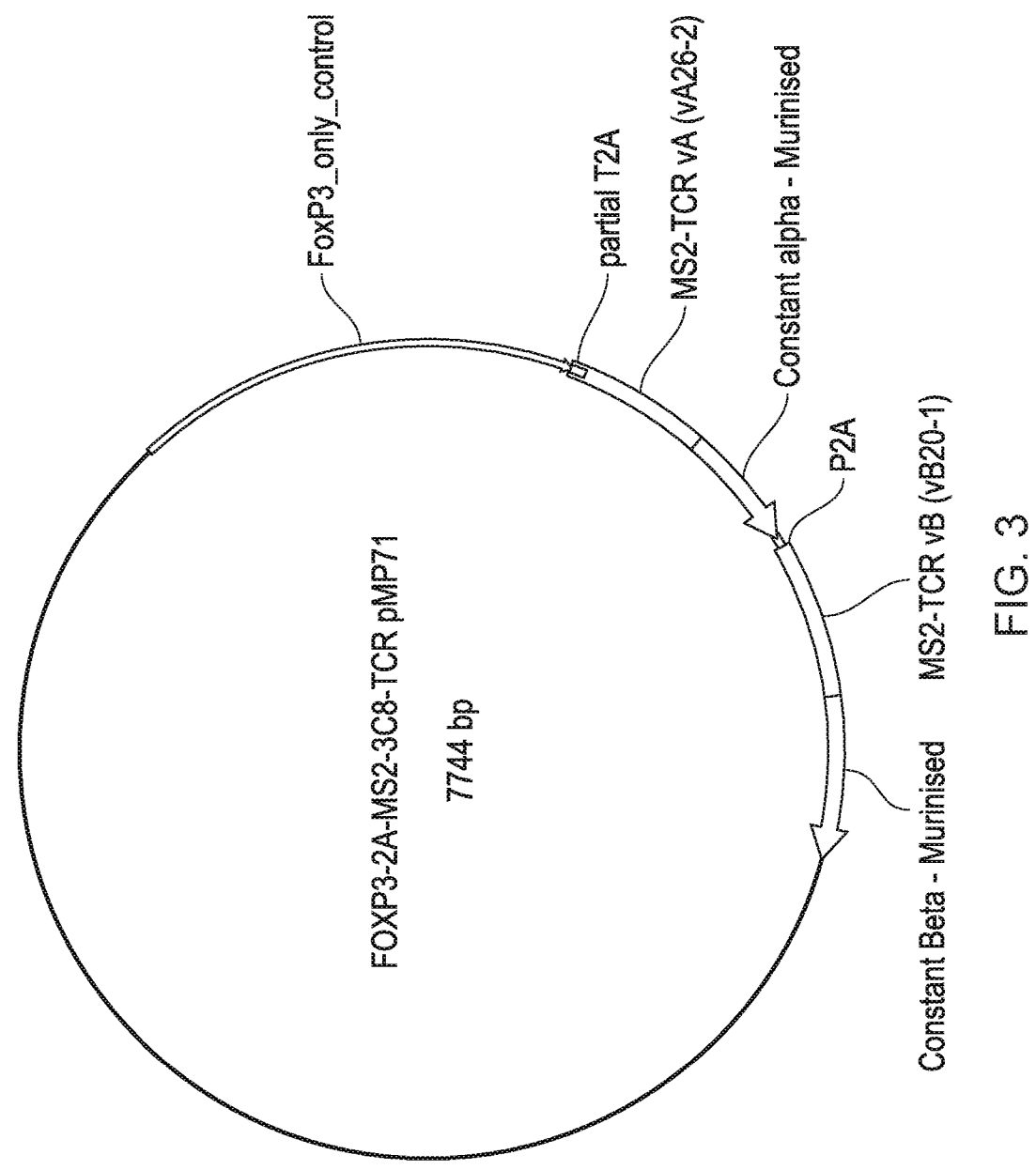
FIG. 3—FOXP3-2A-MS2-3C8 TCR pMP71 comprising a FOXP3 gene with STOP codon removed at the 3' T2A site, inserted into the RsrII and EcoR1 sites upstream of the MS-2 TCR.
Figure 4:
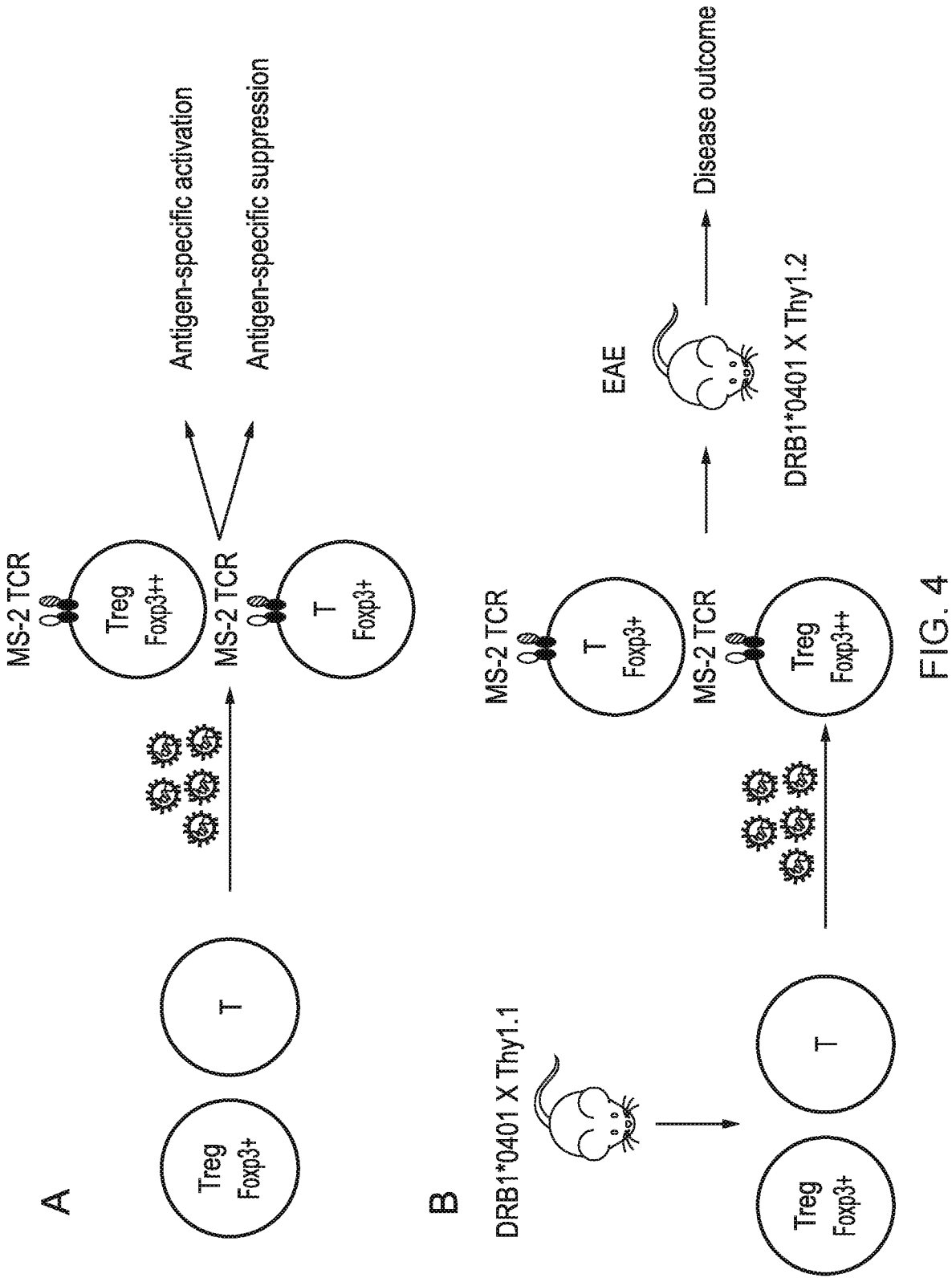
FIG. 4—Schematic showing study design. A) Demonstration of MBP specific suppressive function in an engineered Treg. B) The use of an engineered Treg to suppress MS-like immunopathology in a HLA-transgenic mouse model FIG. 5—Plots show representative flow cytometric analysis performed at day 7 to assess level of transduction through expression of murine TCR constant regions and FOXP3. Treg and Tconv cells are mock transduced, or are transduced with TCR (MS-2) or TCR+FOXP3 (MS-2 FOXP3).

An expression cassette encoding FOXP3 and MS-2 TCR was constructed by modifying the MS-2 TCR described above (FIG. 1 and FIG. 3). A FOXP3 gene with the STOP codon removed and a T2A sequence were inserted into the pMP71 vector using the RsrII and EcoR1 sites upstream of the MS-2 TCR.

Example 2—Transduction of T Cells with TCR and TCR+FOXP3

Phoenix-Ampho cells were seeded at $2 \times 10^6$ in 8 mL of Iscove's Modified Dulbecco's Media (IMDM) in standard tissue culture conditions for 24 hours. On day 1 cells were transfected using FuGENE® transfection reagent and optimum media mixed with 2.5 μg of relevant plasmid DNA and 1.5 μg of pCL-Amp, encoding the ecotropic retroviral co-receptor, for 20 minutes at room temperature. The transfection mixture was added to adherent Phoenix Amphotropic (Phoenix-AMPHO) cells and incubated for a further 24 hours. On day 2 media was changed for 5 mL of Tex-MACS® (Miltenyi) tissue culture media and cells were incubated for a further 24 hours.

CD4+ T cells were isolated using a CD4+ Positive selection kit. Cells were subsequently stained with flow cytometry antibodies CD4, CD25 and CD127 before cell sorting using the BD FACSAria® cytometer.

CD4+CD25hiCD127– Treg and CD4+CD25–CD127+ Tconv were collected in polypropylene tubes. The purity of cell sorting was determined by addition of FOXP3 PE antibody. Purity of CD4+CD25+CD127–FOXP3+ cells was routinely >70%.

On day 0 FACS sorted cells were activated for 48 hours by culturing 1:1 with anti-CD3 and anti-CD28 beads. On day 2 cells were counted and resuspended in complete Roswell Park Memorial Institute medium (RPMI-1640) (Gibco) for Tconv or TexMACS® media for Treg at $1 \times 10^6/$mL. Non-tissue culture-treated 24-well plates were pre-prepared by coating with retronectin, then subsequently blocked with 2% bovine serum albumin in phosphate buffered saline (PBS) and washed ×2 with PBS. The cell suspension was mixed 1:1. The final concentration of IL-2 was 300 u/ml for Tconv and 1000 u/ml for Treg. Cells were incubated overnight at 37 degrees before removing supernatant and supplementing with fresh complete media and IL-2. The media was changed on alternate days.

Tconv cells were grown in RPMI-1640 supplemented with 10% heat inactivated foetal bovine serum (FBS); 100 Units/mL penicillin; 100 μg/mL streptomycin; 2 mM L-glutamine. Regulatory T cells were cultured in TexMACX® media supplemented with 100 Units/mL penicillin; 100 μg/mL streptomycin.

Figure 5:
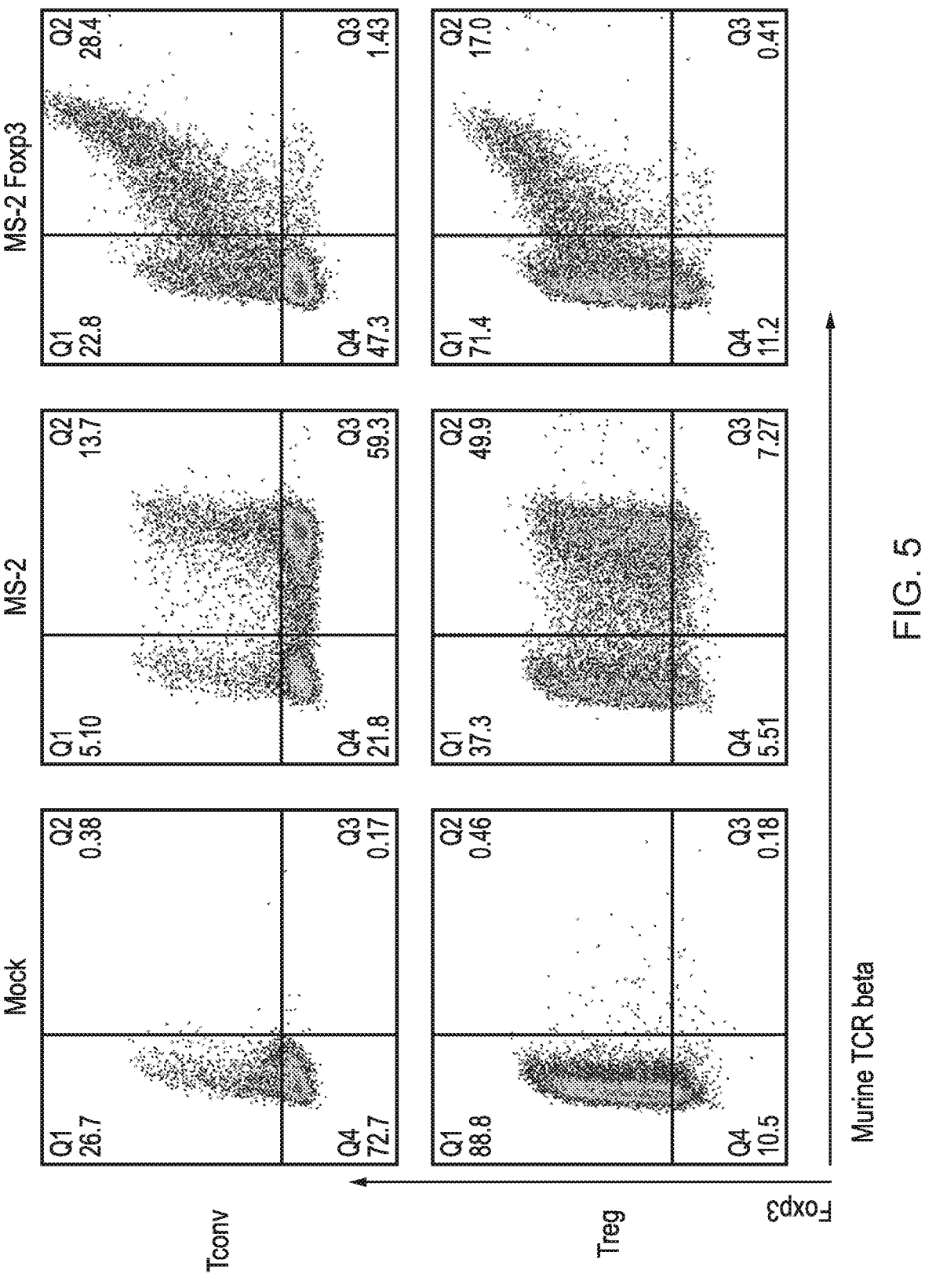

The FACS dot-plots in FIG. 5 show representative flow cytometric analysis performed at day 7 to assess the level of transduction through measurement of the expression of murine TCR constant regions and FOXP3.

Example 3—FOXP3 Expression During In Vitro Expansion

T cells were isolated as described above in Example 2. At day 0 the expression of FOXP3 and Treg cell surface markers CTLA-4 (also known as CD152) and CD25 was measured by flow cytometry.

Figure 6:
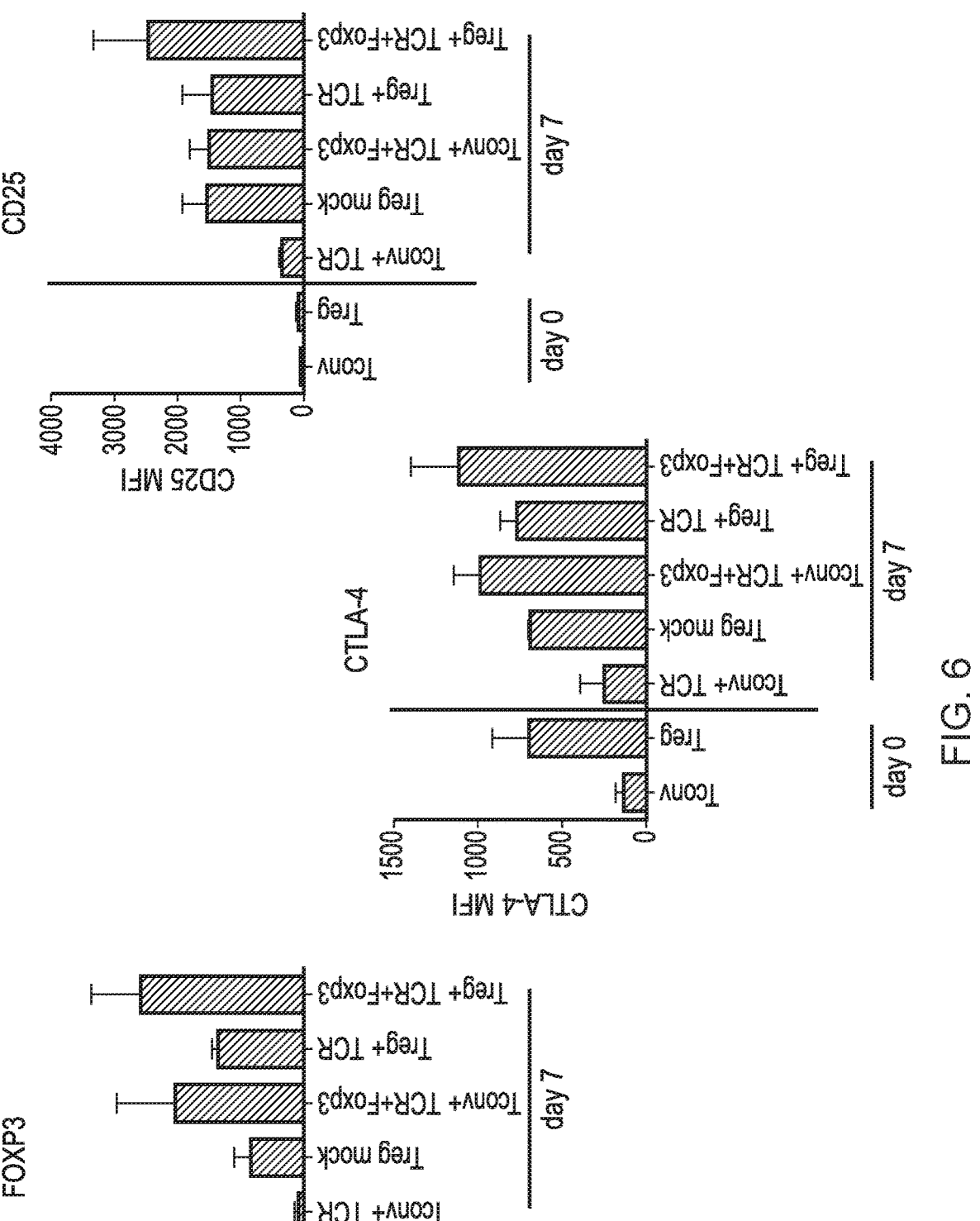
FIG. 6—Graphs showing the relative expression of Treg surface markers on non transduced cells (d0) or gated on transduced cell populations (d7) n=2–4. These results demonstrate that regulatory T cells maintain FOXP3 expression during in vitro expansion.

T cells were transduced and cultured as described above in Example 2. At day 7 the cells were analysed by flow cytometry and the dot-plots were gated on transduced cell populations. The relative expression of FOXP3, CTLA-4 and CD25 was measured. FIG. 6 shows bar charts depicting expression of FOXP3, CTLA-4 and CD25 at day 7 of in vitro expansion. FOXP3 expression is maintained during in vitro expansion.

Antigen-Specific Activation of MS-2 TCR Transduced T Cells

Example 4—Peptide Restimulation of Effector T Cells and Tregs

Chinese Hamster Ovary (CHO) cells were transduced with human HLA-DR4 and CD80 or CD86. Cells expressing CD80 or CD86 were mixed together in equal parts for subsequent experiments.

CHO cells were resuspended at $10 \times 10^6/$mL in culture media with saturating amounts (10 μM/ml) of MBP 111-129 (SEQ ID NO: 12) (LSRFSWGAEGQRPGFGYGG). Suspensions were incubated for 2 hours at standard tissue culture conditions before being irradiated, washed and resuspended.

T cells transduced with MS2 or MS2-FOXP3 construct were washed, counted and resuspended at $0.5 \times 10^6$ cells/ml in complete RPMI. Cells were plated 1:1 with CHO cells incubated with or without peptide for 4 hours. Cells were fixed and permeablised before staining with antibodies for IL-2 and IFNγ.

Figure 7:
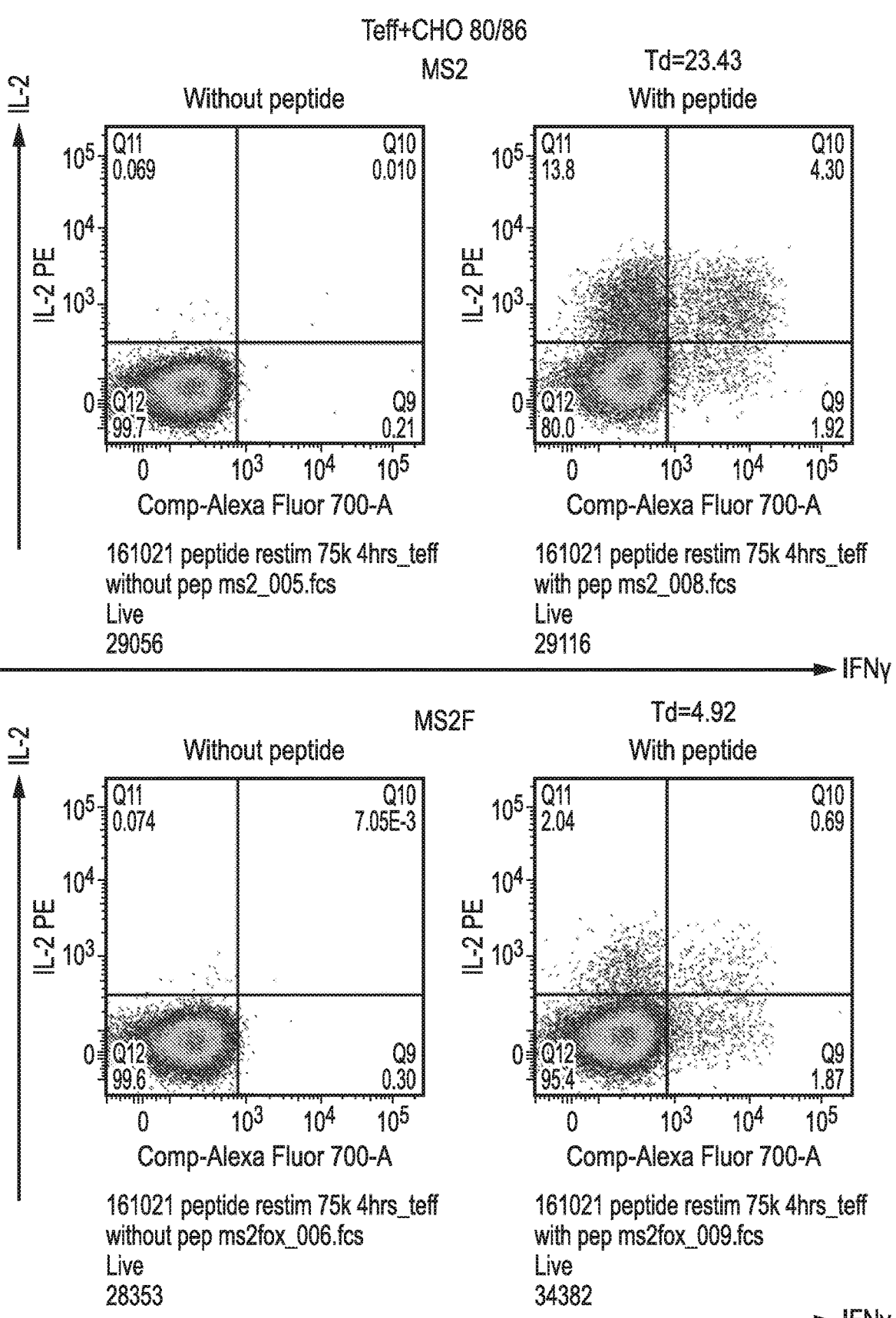
FIG. 7—Graphs showing restimulation of effector T cells with peptide. Chinese Hamster Ovary (CHO) cells were transduced with human HLA-DR4 and CD80 or CD86. Cells expressing CD80 or CD86 were mixed together in equal parts for subsequent experiments. CHO cells were resuspended at $10\times10^6$/mL in culture media with saturating amounts (10 μM/ml) of MBP 111-129 (SEQ ID NO: 12) (LSRFSWGAEGQRPGFGYGG). T cells transduced with a MS2 or MS2-FOXP3 construct were washed, counted and resuspended at $0.5\times10^6$ cells/ml in complete RPMI. Cells were plated 1:1 with CHO cells incubated with or without peptide for 4 hours. Cells were fixed and permeablised before staining with antibodies for IL-2 and IFNγ. Transduction efficiency of T cells is indicated by 'Td='.

FIG. 7 demonstrates FACS dot-plots showing peptide restimulation of effector T cells. The transduction efficiency of T cells is indicated by 'Td='.

Figure 8:
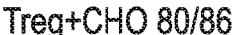
FIG. 8—Graphs showing restimulation of Treg cells with peptide. The method was described above for FIG. 7, using Tregs instead of effector T cells.
Figure 8:
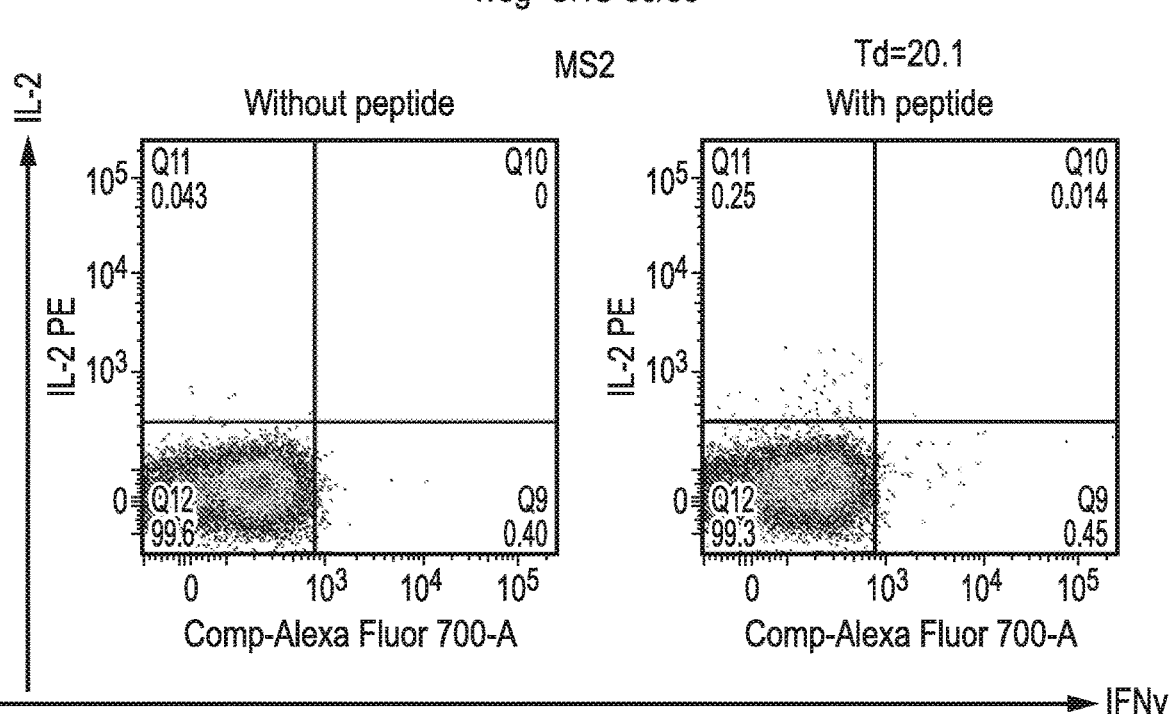
Figure 8:
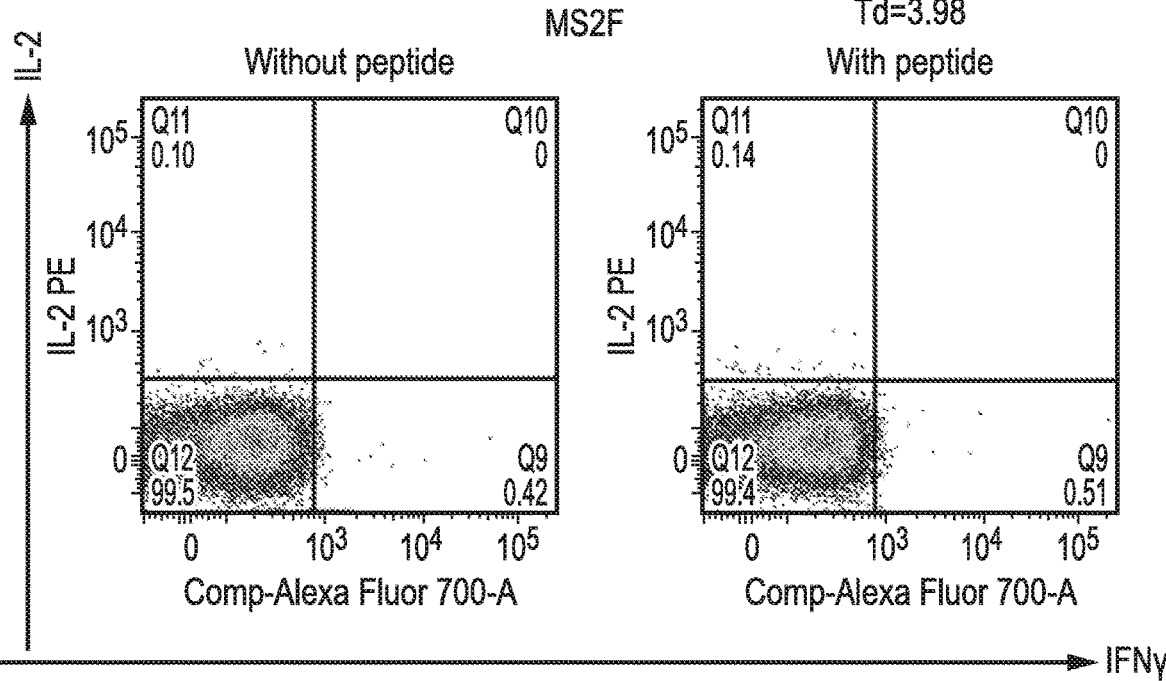

Treg cells were cultured with CHO cells as described above. FIG. 8 demonstrates FACS dot-plots showing peptide restimulation of Treg cells. The transduction efficiency of T cells is indicated by 'Td='.

Figure 9:
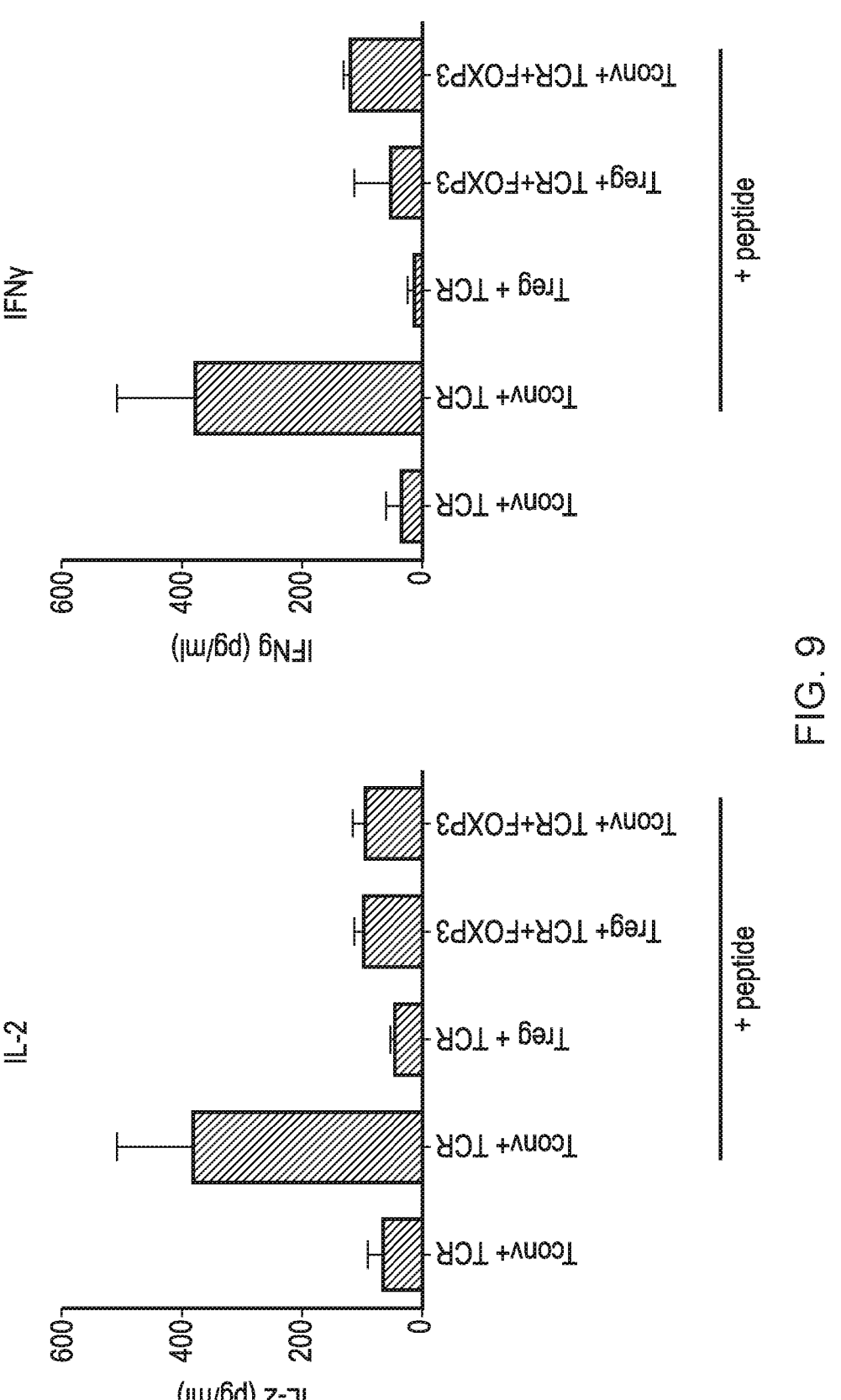
FIG. 9—Transduced T cells were cultured for 4 days with or without pepide-pulsed irradiated APC. Supernatant was collected and assayed for IL-2 and IFNg by ELISA (n=2–4) These data show that TCR-transduced Treg and TCR-FOXP3 converted Tconv are hyporesponsive to cognate peptide.

Example 5—TCR-Transduced and TCR-FOXP3 Transduced T Cells Response to Cognate Peptide TCR-transduced T conv, TCR-transduced Tregs, TCR-FOXP3 converted Tconv and TCR-FOXP3 converted Tconv (methods described above) were cultured for 4 days with or without pepide-pulsed irradiated APC. Supernatant was collected from the culture and assayed for IL-2 and IFNγ by ELISA (n=2–4). FIG. 9 shows that TCR-transduced Treg and TCR-FOXP3 converted Tconv response to cognate peptide.

Example 6—TCR-Transduced and TCR-FOXP3 Transduced

CHO cells were prepared as described above. T conv cells were transduced with TCR or with TCR+FOXP3. Transduced T cells were isolated by magnetic bead sorting. Transduced cells were stained with an anti-murine constant beta antibody conjugated to APC. Cells were thoroughly washed and stained with a second anti-APC antibody. Cells were washed and passed through a magnetic column and transduced cells were captured and eluted. Routinely >95% of purified cells were APC+.

Figure 10:
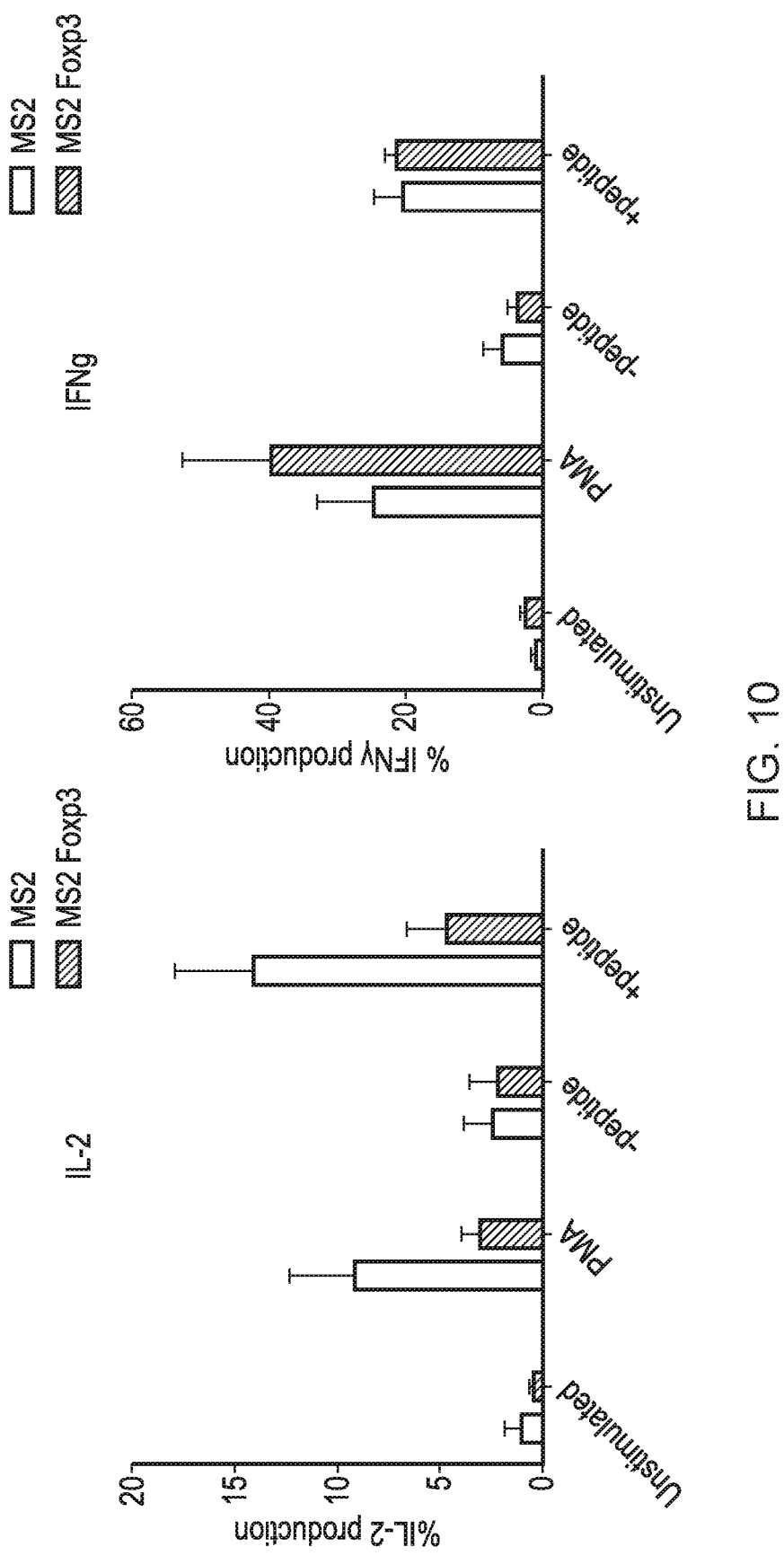
FIG. 10—shows IL-2 and IFNγ production from cells expressing the MS2 TCR and production from T cells expressing MS2 TCR and FOXP3 (n=3). Conventional T cells (T conv) transduced with TCR and TCR+FOXP3 produce less IL-2 than conventional cells transduced with TCR alone.

Unstimulated cells cultured without CHO cells acted as a negative control. PMA (phorbol 12-myristate 13-acetate) stimulated cells acted as a positive control. White bars show cytokine production from cells expressing the MS2 TCR and black bars show cytokine production from T cells expressing MS2 TCR and FOXP3 (n=3). FIG. 10 shows that conventional T cells transduced with TCR and TCR+FOXP3 produce less IL-2 than conventional cells transduced with TCR alone.

Antigen-Specific Suppression of MS-2 TCR Transduced Tregs

Example 7—Proliferation of TCR-Transduced T Cells

CD80+CD86+DR4+CHO cells were loaded with peptide and irradiated as described above before being resuspended at $0.1×10^6$ cells/ml. Transduced responder T cells were stained with CFSE cell trace dye in warmed PBS at 37 degrees for 3 minutes before addition of equal volumes of warm FBS and a further 3 minute incubation.

Cells were washed in 5× volume of complete media before being counting and resuspended at $1×10^6$ transduced cells/ml. The transduction efficiency of Tconv and Treg were determined by flow cytometry. Regulatory T cells are removed from culture, washed and resuspended at $1×10^6$ transduced cells/ml in complete RPMI. Cells were plated 1 Treg:0.1 CHO cells: and varying ratios of Tconv. Proliferation was determined by analysing dilution of carboxyfluorescein succinimidyl ester (CFSE)-stained T conv.

Figure 11:
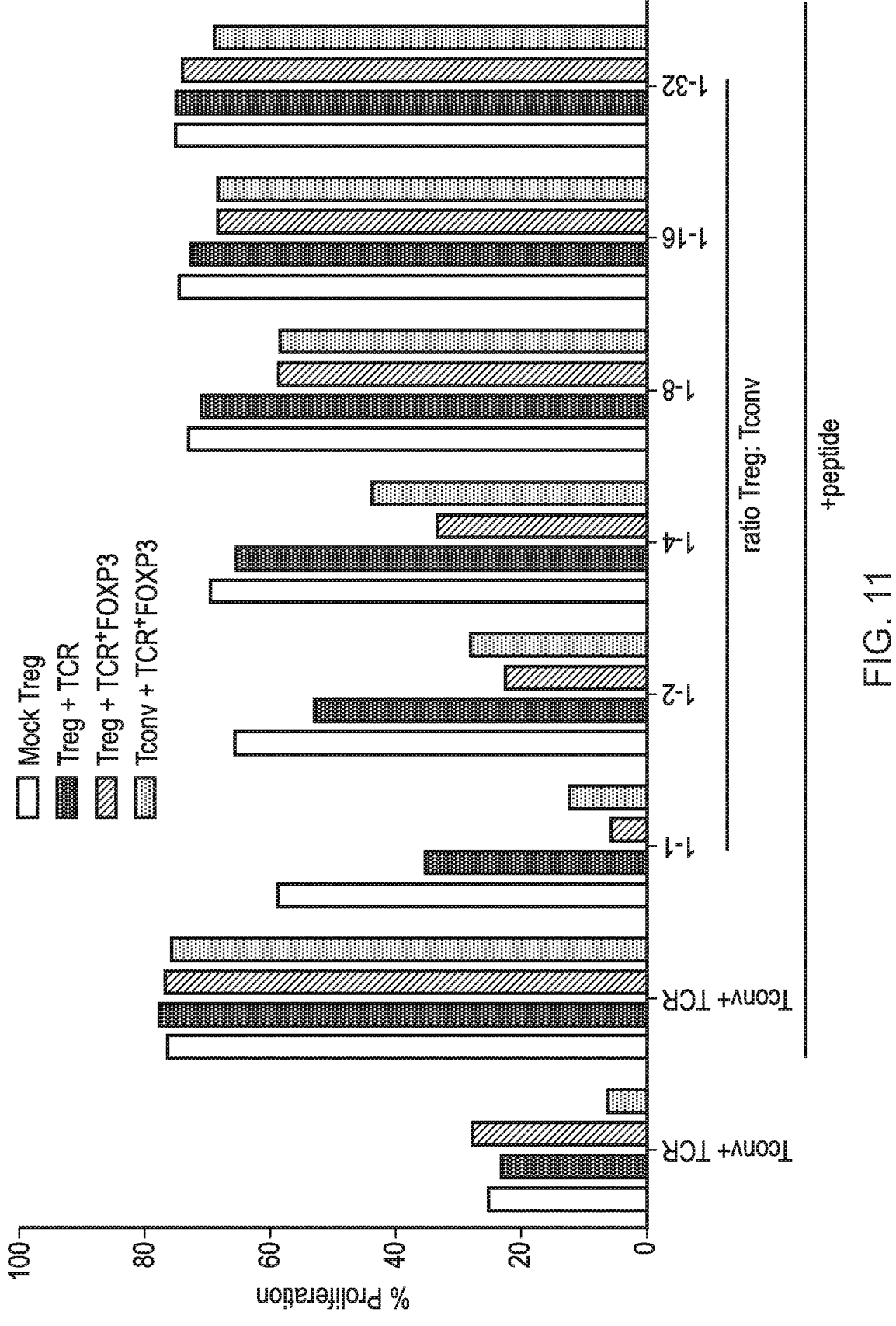
FIG. 11—TCR transduced T conv were stained with CFSE and cultured with or without peptide-pulsed irradiated APC at a ratio of 1 Tconv:0.1 APC for 4 days. Mock Treg (bar on the furthest left), MBP TCR-transduced Treg (second bar from the left), MBP TCR-FOXP3-transduced Treg (third bar from the left) and MBP TCR-FOXP3-transduced Tconv (fourth bar from the left in each group) were added in the indicated ratios. Proliferation was determined by analysing dilution of CFSE-stained Tconv (B). These data show that TCR-transduced Treg suppress T cell responses in an antigen-specific manner.
Figure 12:
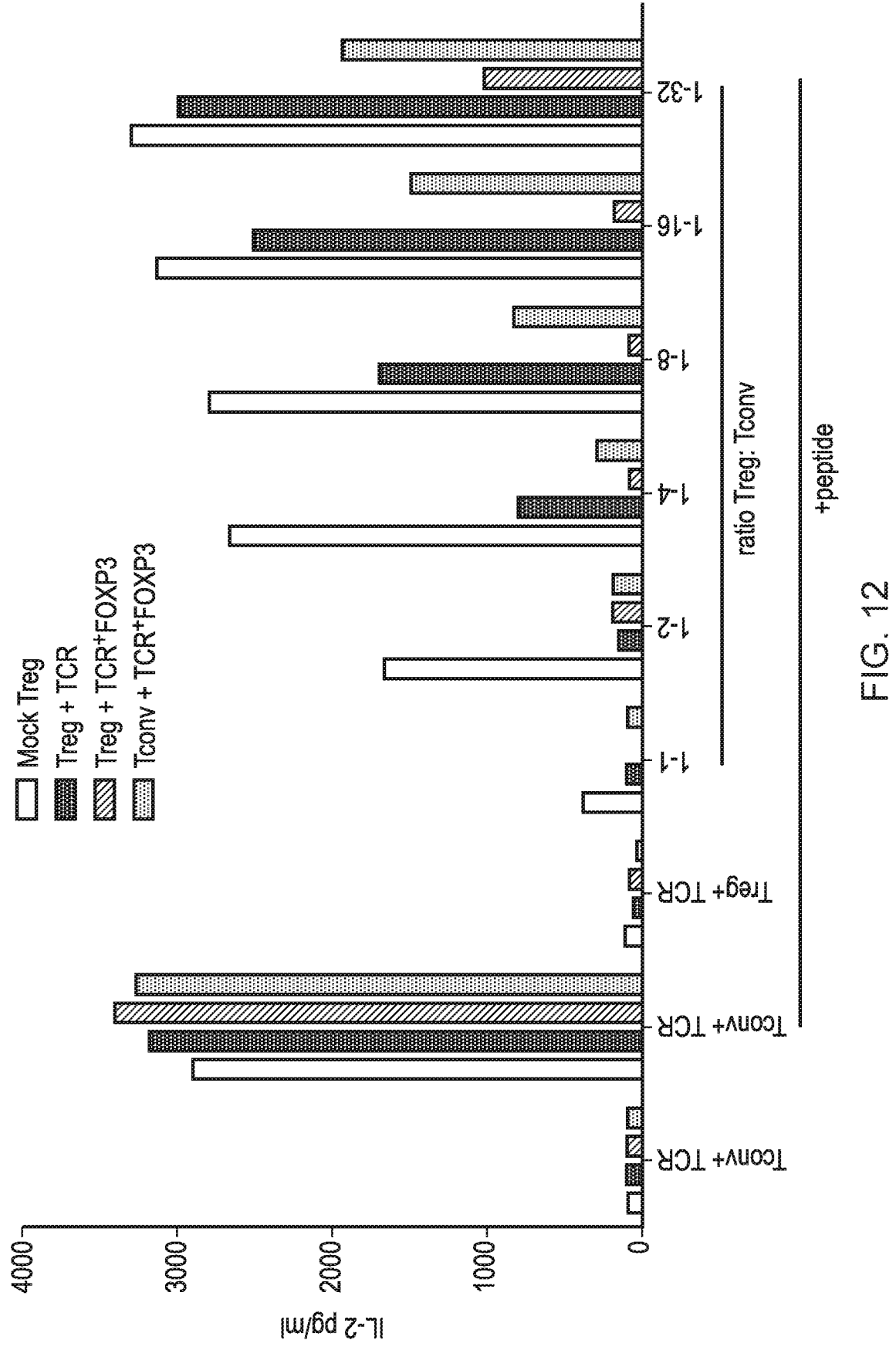
FIG. 12—TCR transduced T cony were stained with CFSE and cultured with or without peptide-pulsed irradiated APC at a ratio of 1 Tconv:0.1 APC for 4 days. Mock Treg (bar on the furthest left), MBP TCR-transduced Treg (second bar from the left), MBP TCR-FOXP3-transduced Treg (third bar from the left) and MBP TCR-FOXP3-transduced Tconv (fourth bar from the left in each group) were added in the indicated ratios. Supernatants were collected and assayed for IL-2 by ELISA. These data show that TCR-transduced Treg suppress T cell responses in an antigen-specific manner.

The data in FIG. 11 show that TCR-transduced Tregs suppress proliferation in an antigen-specific manner. Supernatants were collected from the culture media and were assayed for IL-2 by ELISA. The data presented in FIG. 12 show that TCR-transduced Treg suppress IL-2 production in an antigen-specific manner.

Example 8—Engineered Tregs in an Adoptive Transfer Model of Experimental Autoimmune Encephalomyelitis Human conventional T cells which have been transduced with MS2-3C8 TCR are administered to immunodeficient NOD scid gamma mice (NSG) transgenic for HLADRB1*0401 by adoptive transfer.

Adoptive transfer of the human T cells may induce an experimental autoimmune encephalomyelitis (EAE) type disease in the mice. The mice are then treated with human Treg cells which have been transduced with MS2-3C8 TCR or control Tregs.

HLA-DRB1+0401-restricted MBP 111-129 (SEQ ID NO: 12)-specific humanised TCR transgenic mice have infiltrates of MS2-3C8 transgenic T cells and inflammatory legions located in the brainstem and the cranial nerve roots in addition to the spinal cord and spinal nerve roots (Quandt et al., J. Exp. Med. V. 200(2); 2004 incorporated herein by reference).

The suppression of proliferation of pathogenic T cells by TCR induced Tregs is measured in the mouse model e.g. by CFSE, IL-2 and/or IFNγ levels.

Example 9—Engineered Tregs in Classical Model of Experimental Autoimmune Encephalomyelitis Mice are immunised with Mog (myelin oligodendrocyte protein) to induce EAE, a widely accepted animal model of MS.

The mice are then treated with human Treg cells which have been transduced with MS2-3C8 TCR or control Tregs. The suppression of proliferation of pathogenic T cells by TCR induced Tregs is measured in the mouse model e.g. by CFSE, IL-2 and/or IFNγ levels.

Example 10—TCR Transduced Regulatory T Cells can Engraft into Irradiated Hosts

CD4+CD25+ Treg were isolated from lymph nodes and splenocytes of HLA-DRB*0401 transgenic mice by bead sort. Treg were transduced with TCR. 1 day after transduction TCR or TCR+FOXP3 transduced cells were injected into HLA-DRB*0401 transgenic hosts conditioned with 4 Gy irradiation (day 0). 7 weeks later flow cytometry was used to determine the engraftment of transduced Treg via staining for TCR (+7 weeks).

Figure 13:
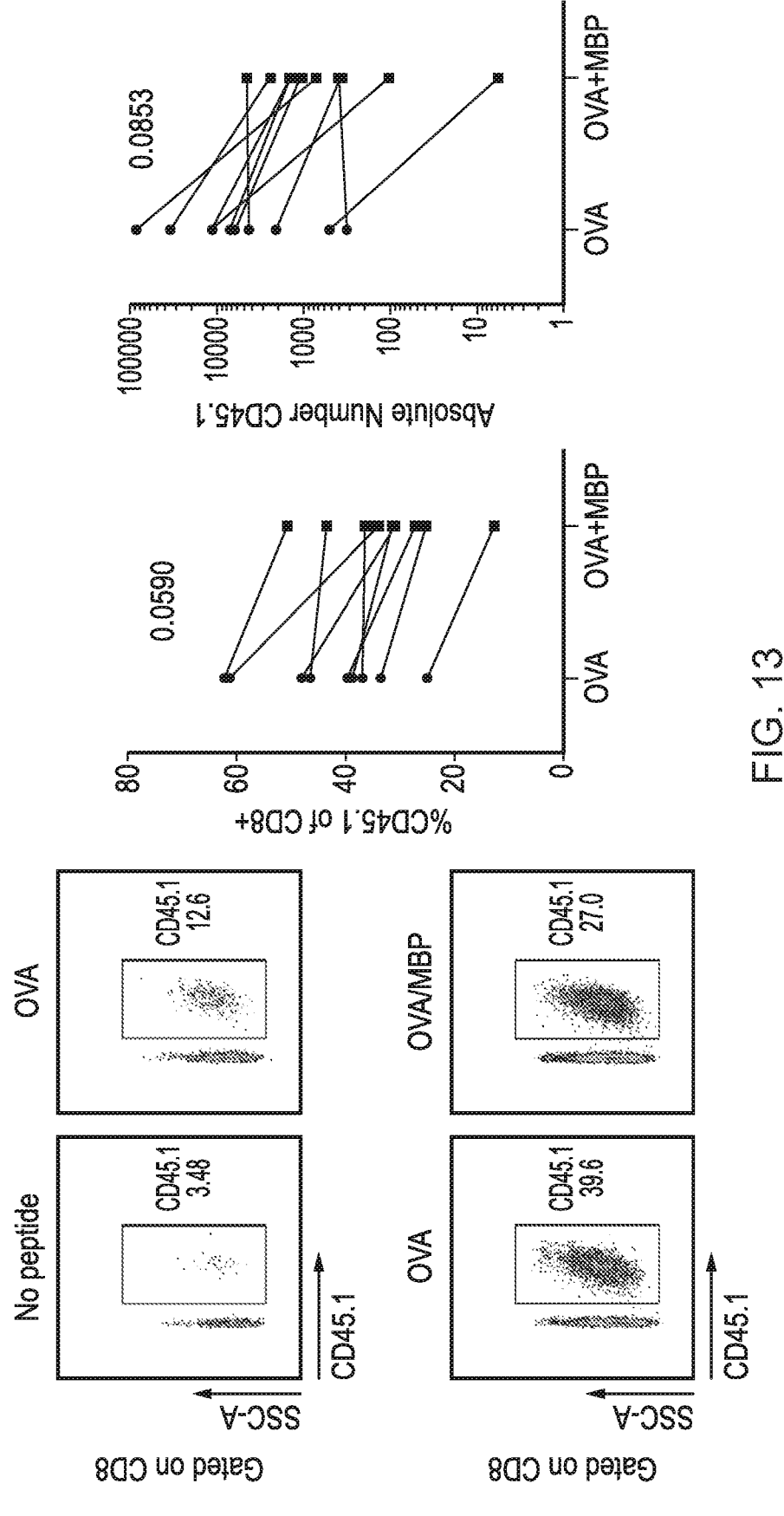
FIG. 13—CD4+CD25+ Treg were isolated from lymph nodes and splenocytes of HLA-DRB*0401 transgenic mice by bead sort. Treg were transduced with TCR+murine FOXP3. Transduced cells and equivalent numbers of CD45.1+OTI transgenic T cells were injected into HLA-DRB*0401 transgenic hosts conditioned with 4 Gy irradiation. After 7 days mice were injected sub-cutaneously in the right or left flank with 30 ug ovalbumin (OVA) or 30 ug of OVA and 30 ug of human myelin basic protein (MBP) in incomplete Freud's adjuvant A. Paired FACS plots show OTI cells identified by CD45.1 in the right and left inguinal lymph nodes of the same mouse. The left plot shows the data from an uninjected flank (no peptide) and the right shows data from the flank injected with OVA peptide B. Paired FACS plots show OTI cells in the right and left inguinal lymph nodes of the same mouse. The left plot shows the data from the flank injected with OVA and the right shows data from the flank injected with OVA+MBP peptides C. Cumulative data from 3 independent experiments showing % CD45.1+ cells (left panel) and absolute number of CD45.1 cells in the inguinal lymph node of the flank that received OVA or OVA+MBP (n=9).
Figure 13:
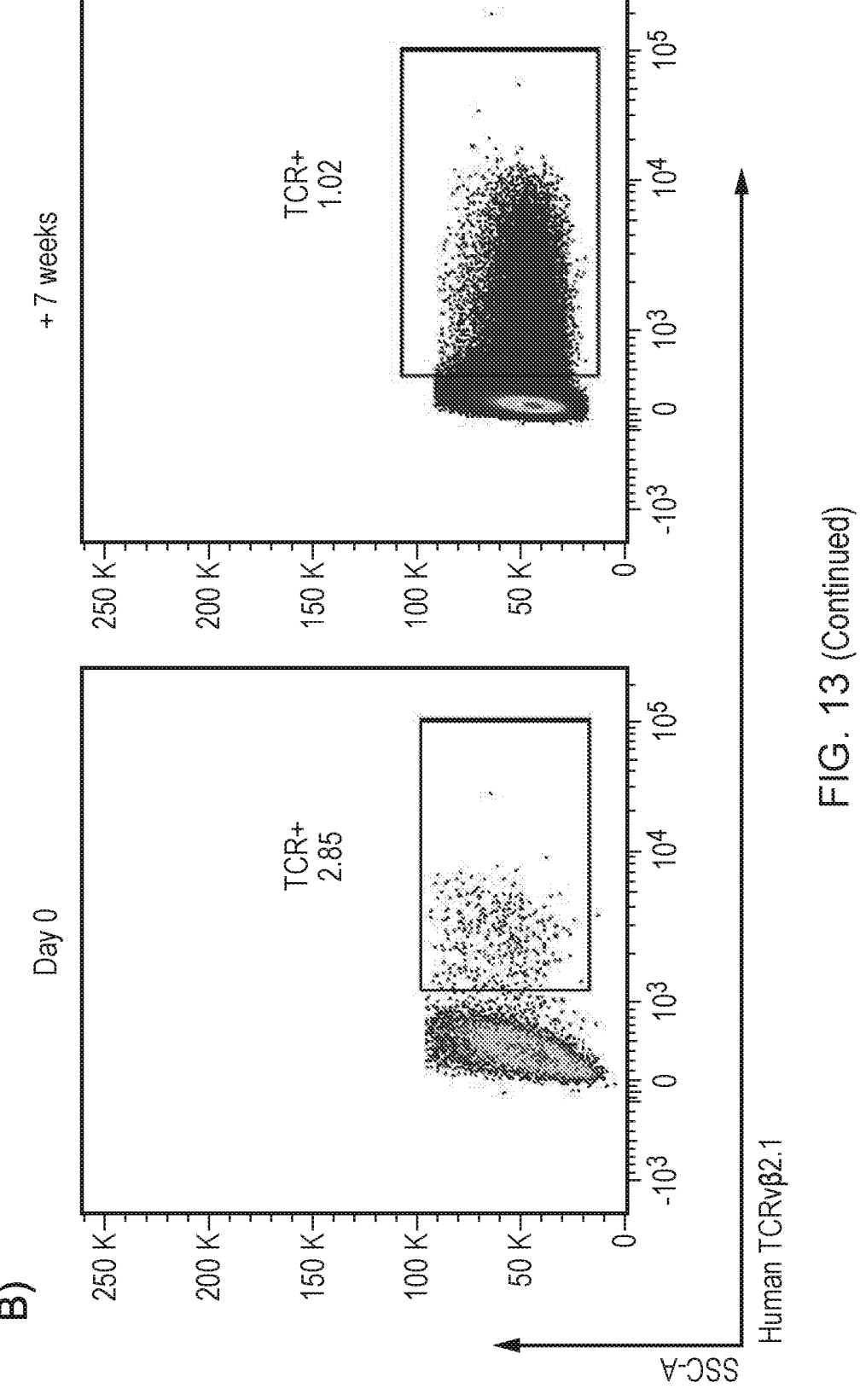
Figure 13:
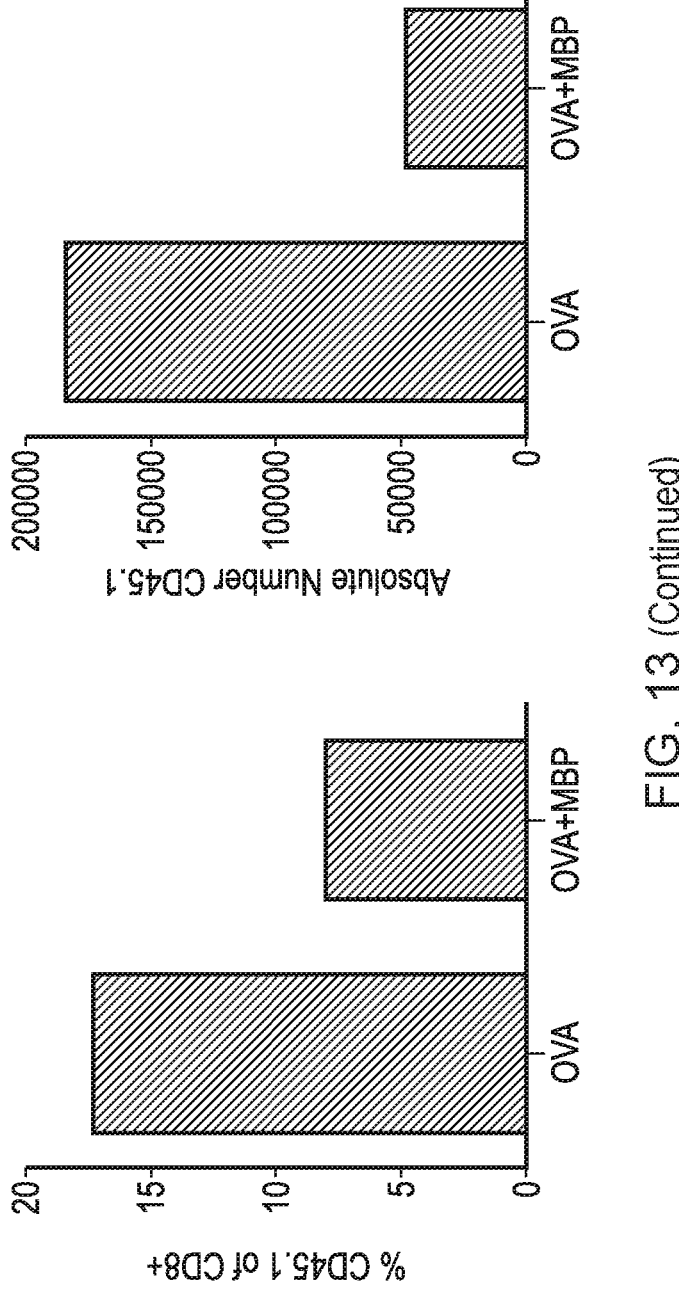

The results in FIG. 13 show persistence of Tregs and an antigen-specific suppressive effect 7 weeks post-administration.

Example 14—Expression and Functional Studies with Codon-Optimized MS2-3C8

Figure 14:
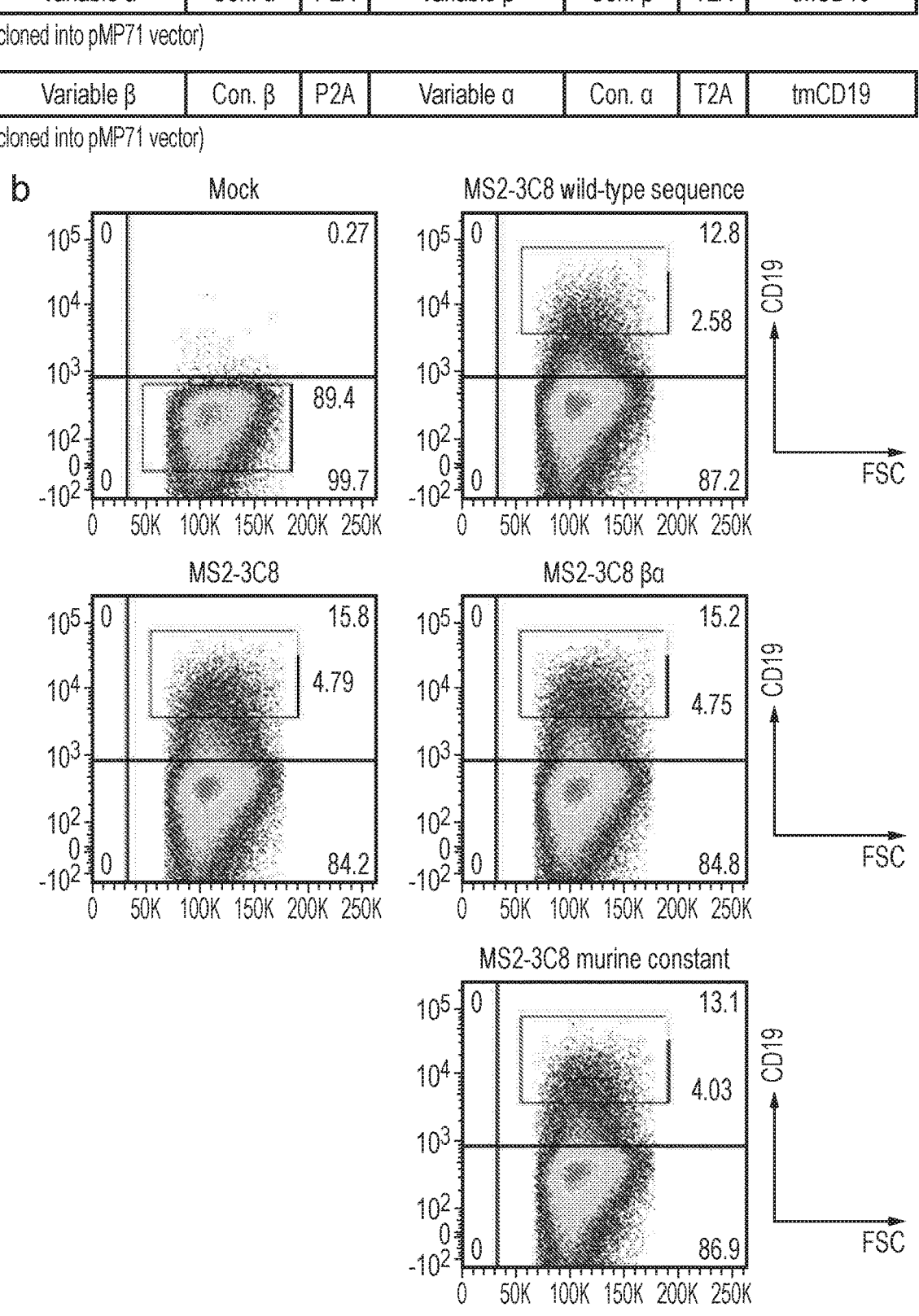
FIG. 14—Schematic representation of the retroviral vectors for the MS2-3C8 TCRs and MS2-3C8 TCRs expression and functional studies. (a) Top panel: The following TCRs were cloned into the retroviral pMP71 vector using the alpha chain—P2A—beta chain—T2A—truncated murine CD19 (tmCD19) configuration: MS2-3C8 wild-type sequence; MS2-3C8 and MS2-3C8 murine constant. Bottom panel: The MS2-3C8 ba TCR variant was cloned into the retroviral pMP71 vector using the beta chain—P2A—alpha chain—T2A—truncated murine CD19 configuration. Truncated murine CD19 was used as a marker of transduction efficiency. All TCRs, except MS2-3C8 wild-type sequence, contained codon optimised variable and constant domains. (b) Representative example of 3 independent experiments showing Jurkat cells (not expressing an endogenous TCR) transduced with the retroviral constructs encoding the indicated TCRs. Top panel: CD19 expression levels. Bottom panel: CD3 expression levels and TRBV20 (IMGT nomenclature) expression levels in gated $CD19^{high}$ cells. CD3 is used as a surrogate marker for TCR cell surface expression. Cells were stained with anti-TRBV20 Abs to determine variable beta chain expression. (c) Representative example of 4 independent experiments showing MACS sorted CD4+ human T cells transduced with the retroviral constructs encoding the indicated TCRs. Top panel: CD19 expression levels. Bottom panel: The percentage of CD4+ cells expressing TRBV20 in gated $CD19^{high}$ cells. Cells were stained with anti-TRBV20 Abs to determine variable beta chain expression. (d) Representative example of 4 independent experiments showing human CD4+ T cells transduced with the indicated TCRs and stimulated with APCs loaded with saturating concentrations of relevant peptide or control peptide. Shown is the frequencies of gated $CD19^{high}$ T cells that produced IL2 and/or IFNg as determined by intracellular cytokine staining 18 h after stimulation in the presence of BFA. APCs were CHO cells expressing CD80 and CD86 and HLA-DRB1*401. (e) Suppression assay assessing production MBP-specific pro-inflammatory cytokine. FACS-sorted effector CD4 T cells ($CD25^{low}CD127^{high}$) were transduced with MS2-3C8 and donor-matched FACS-sorted Tregs ($CD4+CD25^{high}CD127^{low}$) were transduced with MS2-3C8 or mock-transduced. Up to 50,000 MS2-3C8- expressing Tregs and 50,000 T effectors per well were co-cultured for 3 days with 5,000 APCs loaded with the relevant MBP-peptide in a 96-well plate. IL-2 and IFN-γ concentrations in the culture medium were measured by ELISA.
Figure 14:
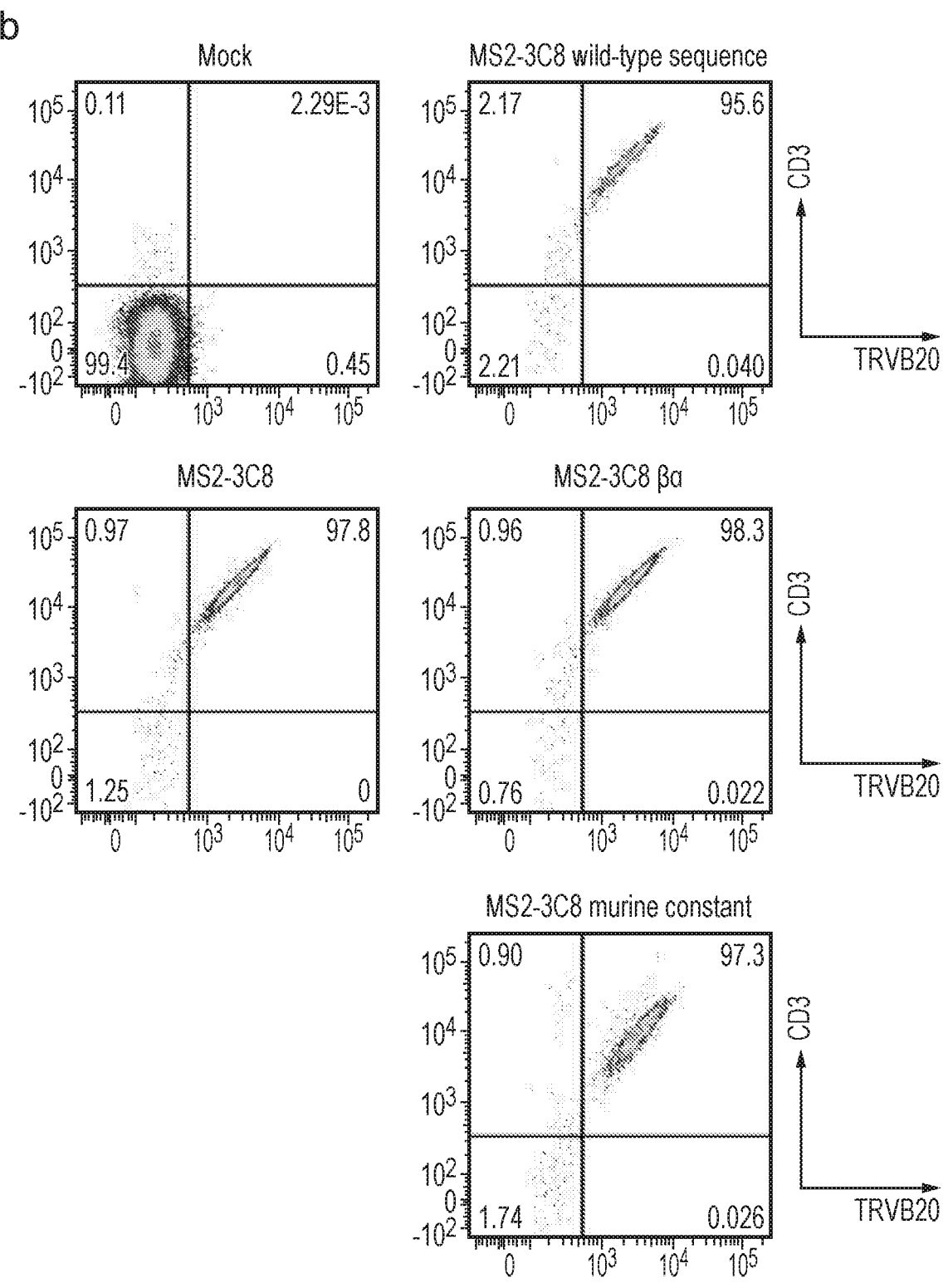
Figure 14:
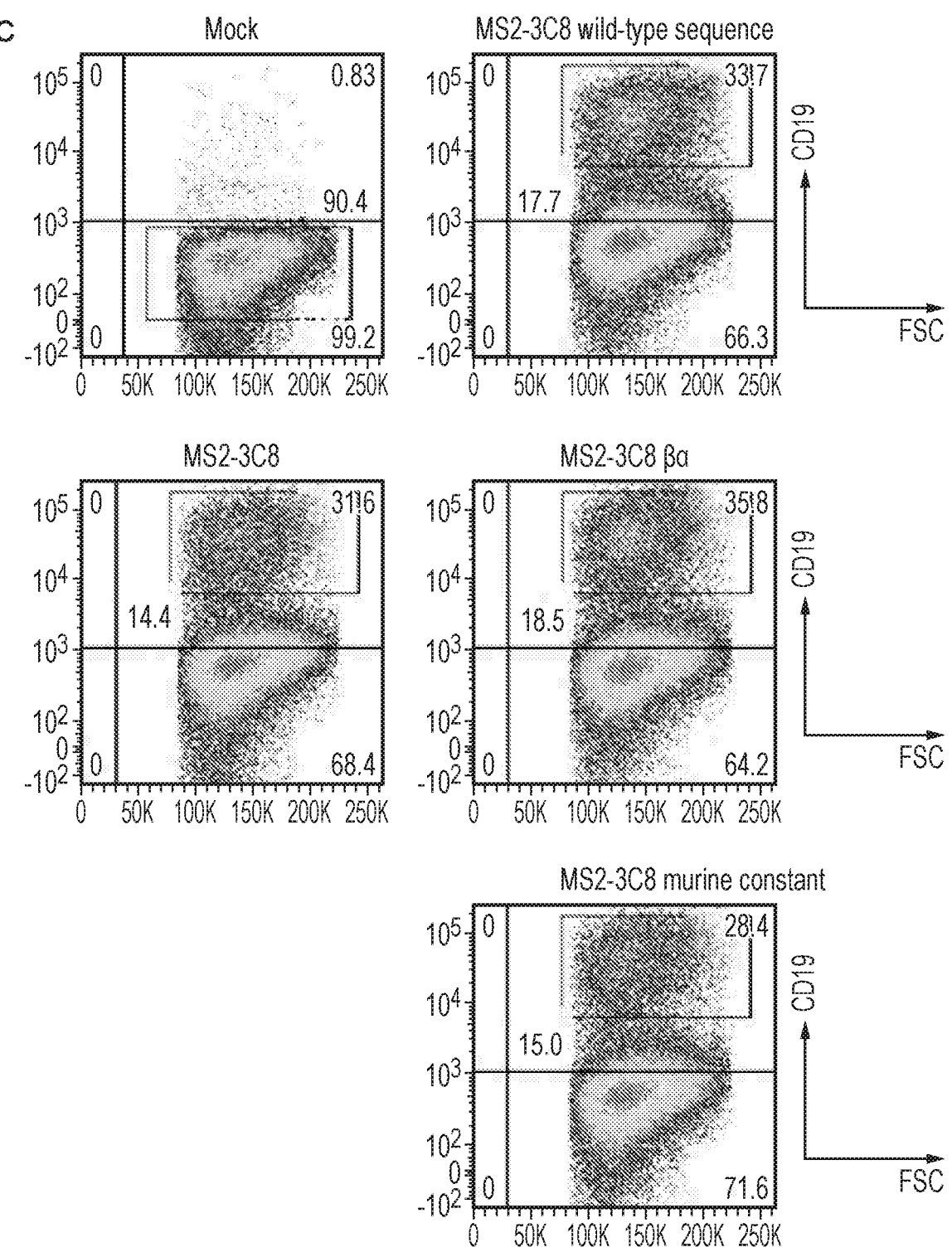
Figure 14:
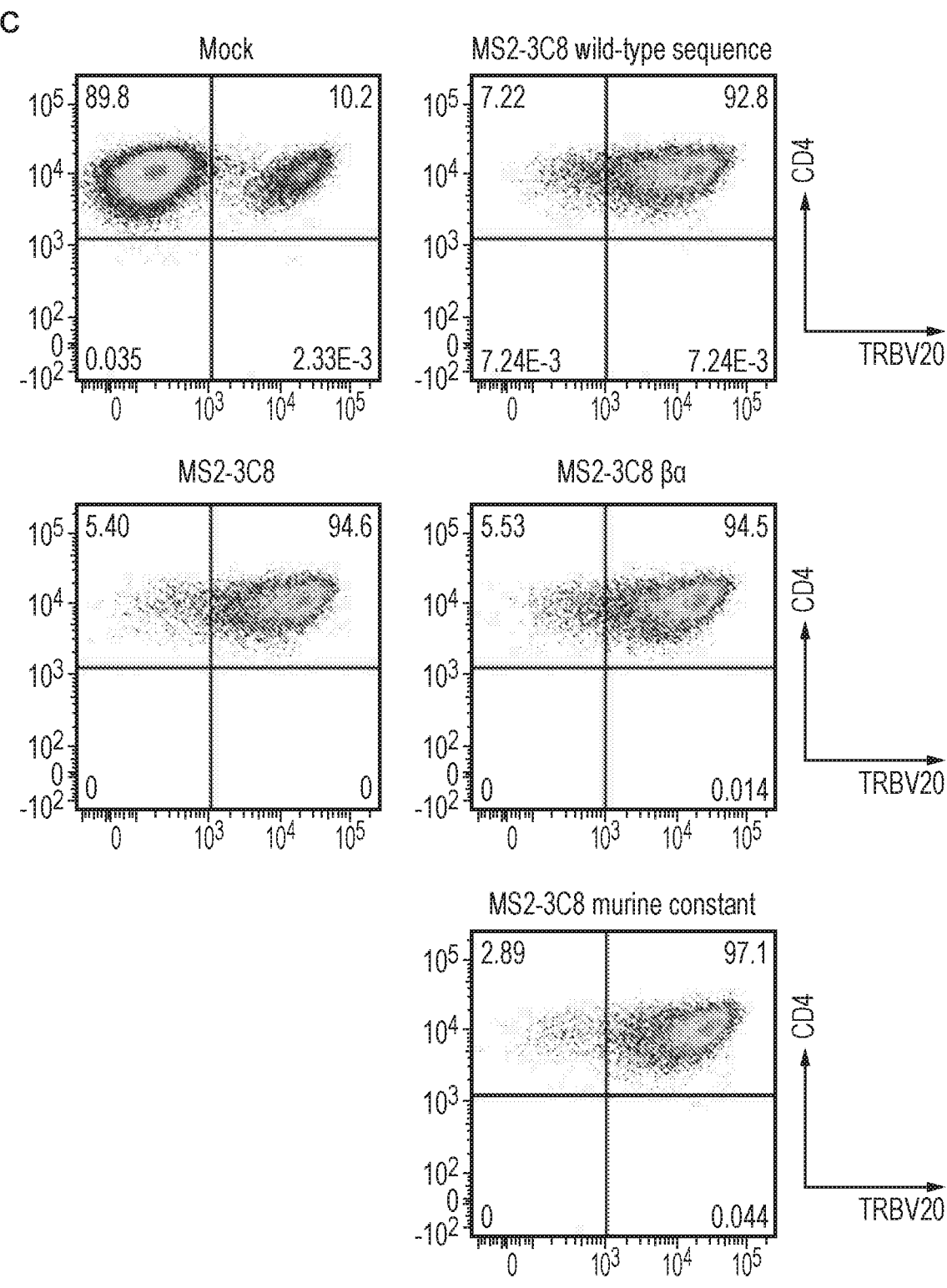
Figure 14:
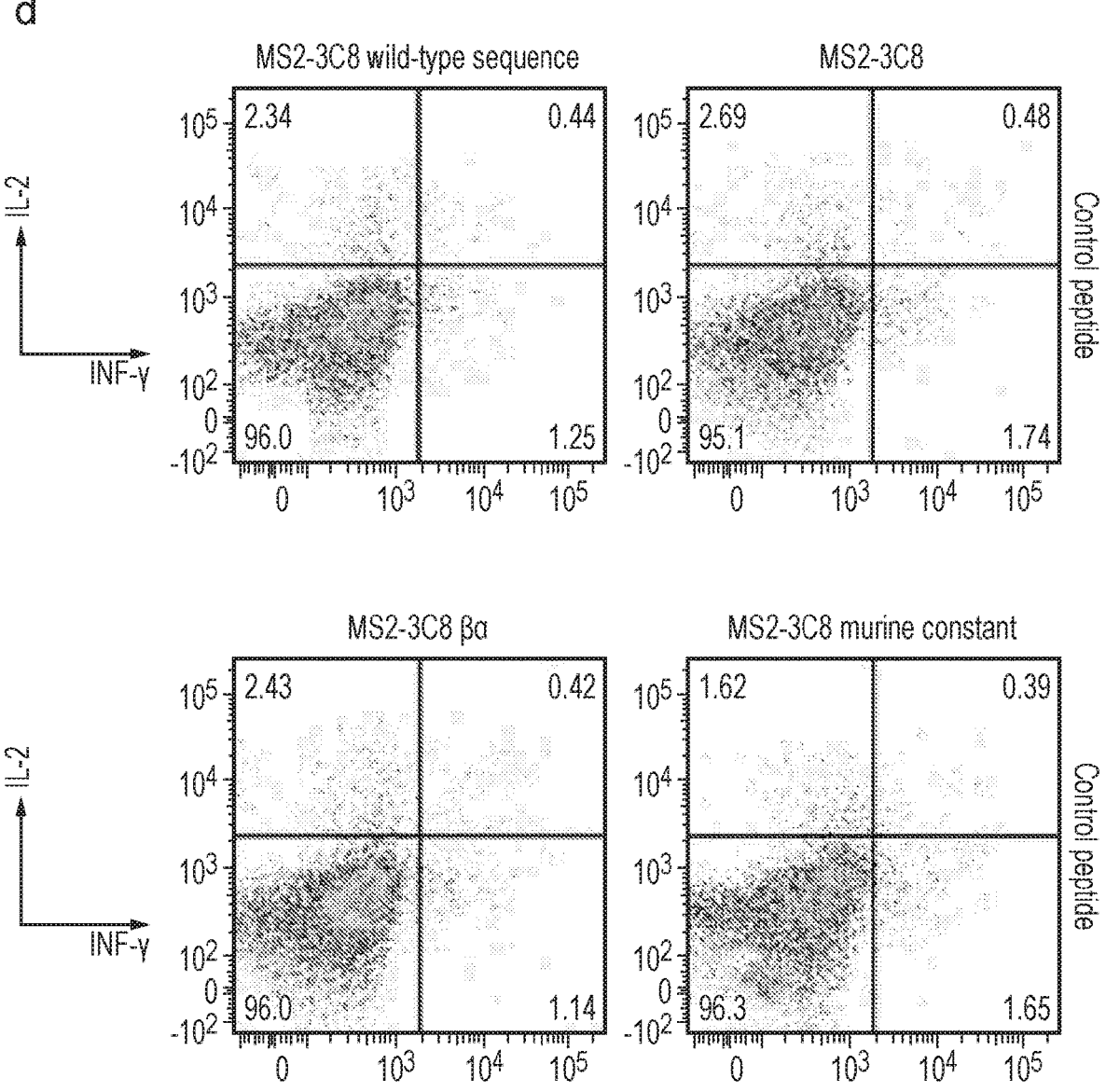
Figure 14:
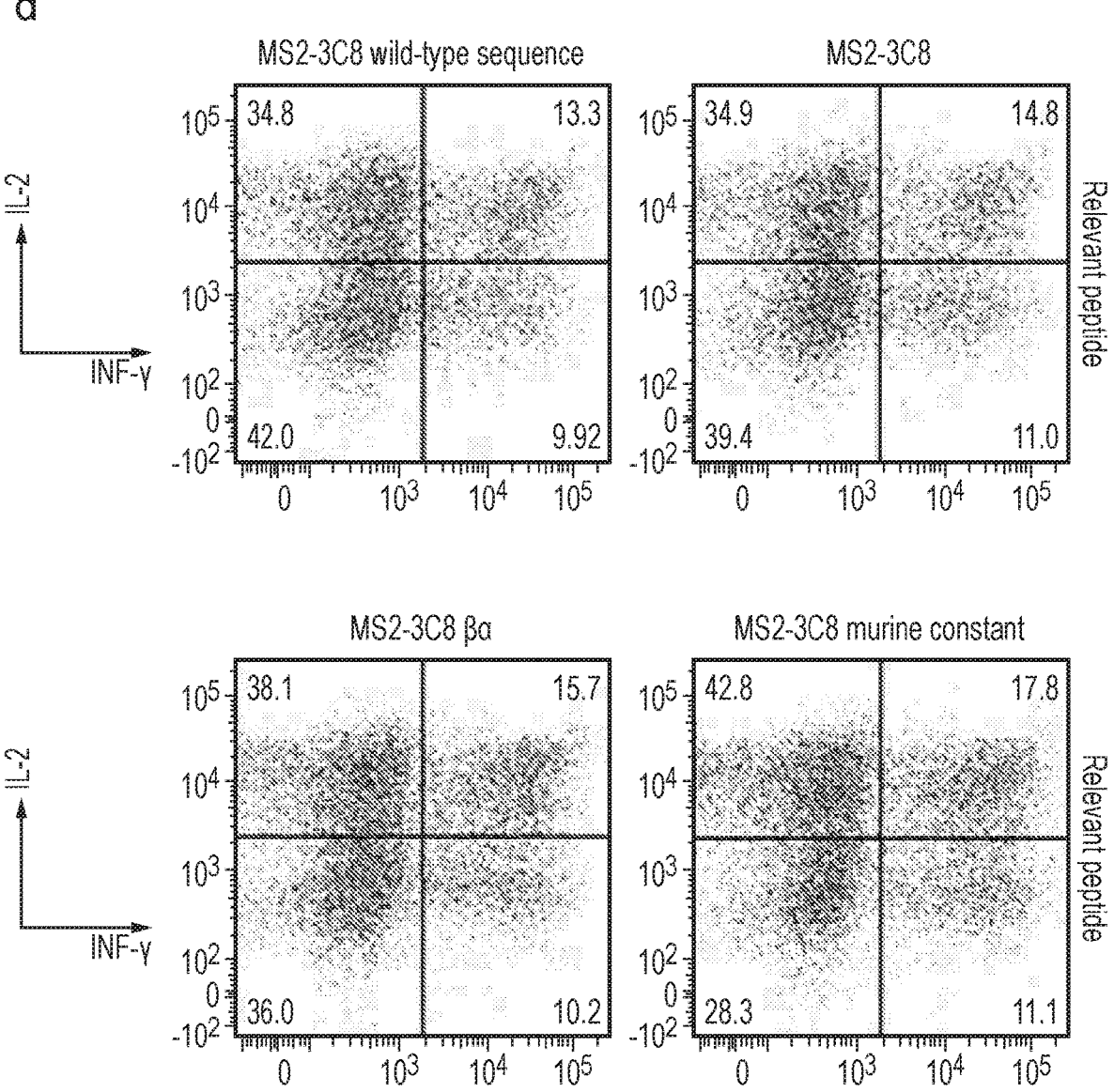
Figure 14:
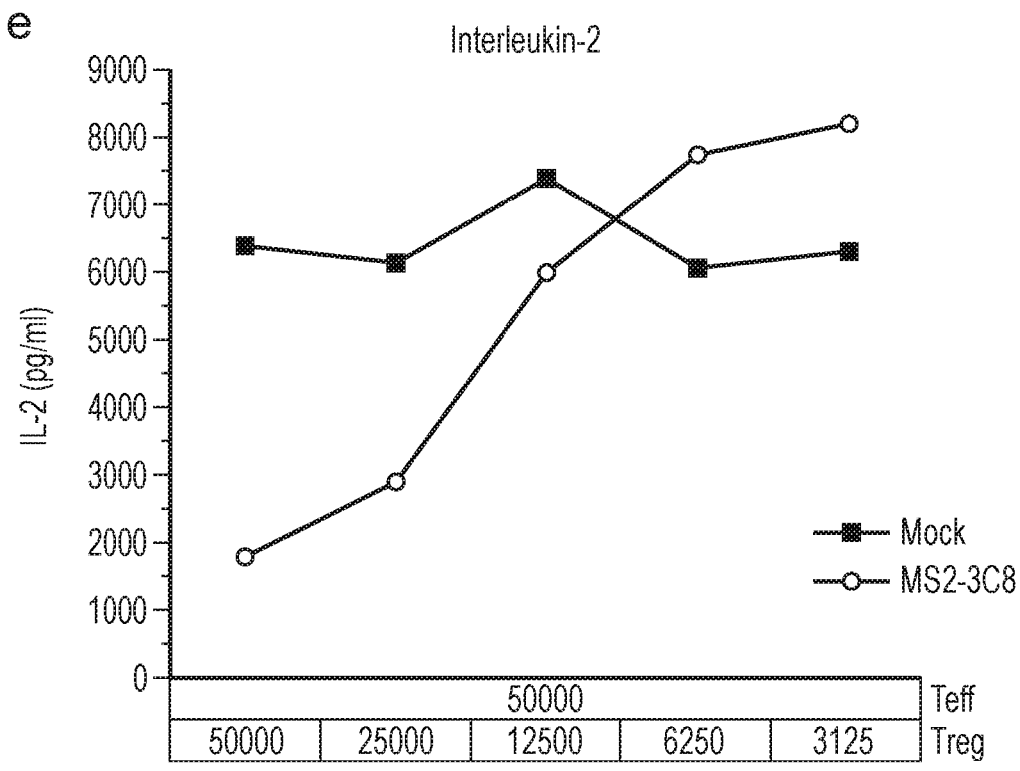
Figure 14:
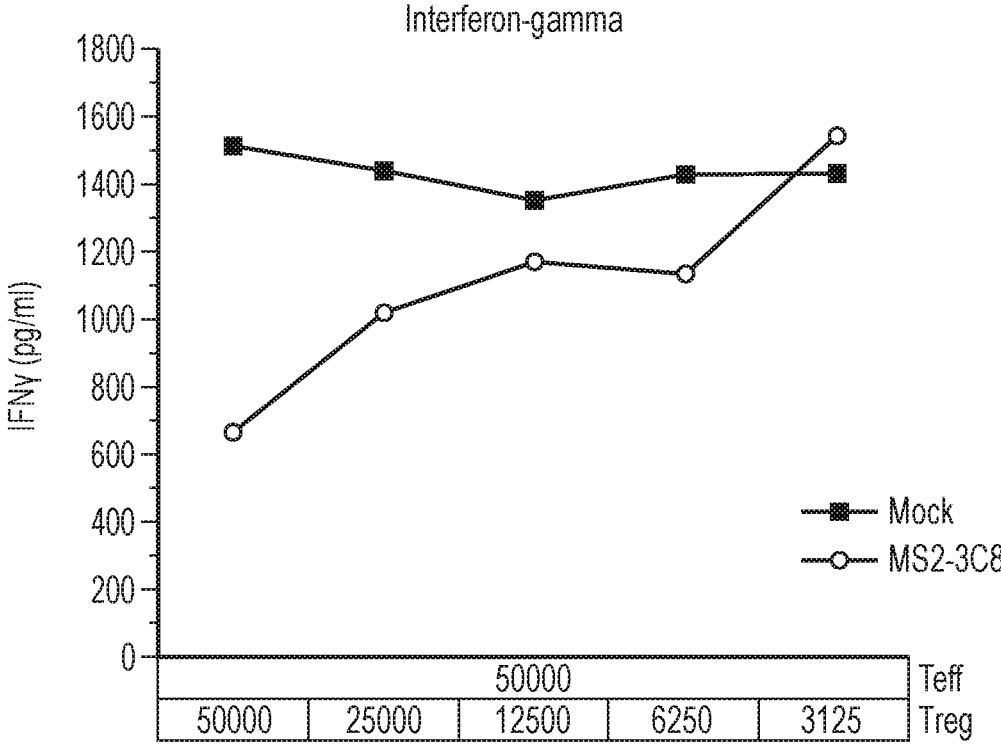

Codon-optimized sequences for MS2-3C8 TCR were cloned into the retroviral pMP71 vector using the alpha chain—P2A—beta chain—T2A—truncated murine CD19 (tmCD19) or beta chain—P2A—alpha chain—T2A—truncated murine CD19 (tmCD19) configuration (FIG. 14A).

The MS2-3C8 TCRs were productively expressed in Jurkat cells (FIG. 14B) and CD4+ human T cells (FIG. 14C). Results were compared to MS2-3C* wild-type sequences and MS2-3C8 TCR with murine constant domain.

Human CD4+ T cells transduced with codon-optimized MS2-3C8 TCR, wild-type MS2-3C8 TCR or MS2-3C8 TCR with murine constant domain and stimulated with APCs loaded with saturating concentrations of relevant peptide were capable of antigen-specific cytokine responses (FIG. 14D).

A suppression assay assessing production MBP-specific pro-inflammatory cytokine was also performed showing antigen-specific suppression data for the MS2-3C8 TCR (FIG. 14E).

Example 15—Antigen-Specific Suppression of with a Reference MBP TCR Transduced Tregs CD80+CD86+DR4+ CHO cells were loaded with peptide and irradiated before being resuspended at $0.1 \times 10^6$ cells/ml. Transduced responder T cells were stained with CFSE cell trace dye in warmed PBS at 37 degrees for 3 minutes before addition of equal volumes of warm FBS and a further 3 minute incubation.

Cells were washed in 5× volume of complete media before being counting and resuspended at $1 \times 10^6$ transduced cells/ml. The transduction efficiency of Tconv and Treg were determined by flow cytometry. Regulatory T cells are removed from culture, washed and resuspended at $1 \times 10^6$ transduced cells/ml in complete RPMI. Cells were plated 1 Treg:0.1 CHO cells: and varying ratios of Tconv. Proliferation was determined by analysing dilution of carboxyfluorescein succinimidyl ester (CFSE)-stained T con.

The data in FIG. 15 show that TCR-transduced Tregs suppress proliferation in an antigen-specific manner. Supernatants were collected from the culture media and were assayed for IL-2 by ELISA. The data presented in FIG. 15 show that TCR-transduced Treg suppress IL-2 production in an antigen-specific manner.

The expression cassette used in this reference experiment encoded FOXP3 and the reference MBP TCR in a 5'-3' orientation.

Example 16A—Treg Expressing Exogenous FOXP3 Engraft, Persist and Retain FoxP3, CD25 and TCR Expression Thy1.1+CD4+CD25+ or CD45.1+CD4+CD25+ Treg were isolated from lymph nodes and splenocytes of HLA-DRB*0401 transgenic mice by bead sort. CD45.1+ Treg were transduced with TCR and Thy1.1+ Treg were transduced with TCR+murine FOXP3. 1 day after transduction TCR or TCR+FOXP3 transduced cells were injected in a 1:1 ratio into HLA-DRB*0401 transgenic hosts conditioned with 4 Gy irradiation. FACS plots show the ratio of CD45.1: Thy1.1 of injected cells and their respective FOXP3 expression.

After 7 weeks flow cytometry was used to identify engrafted cells by staining for TCR. The ratio of CD45.1: Thy1.1 within the TCR+ population was determined and the phenotype of engrafted CD45.1 (Treg transduced with TCR) or Thy1.1 (Treg transduced with TCR+FOXP3) cells was examined by staining for FOXP3 and CD25.

Thy1.1+CD4+CD25+ Treg were isolated from lymph nodes and splenocytes of HLA-DRB*0401 transgenic mice by bead sort. Treg were transduced TCR, TCR+murine FOXP3 or cultured with virus-free supernatant (mock). 1 day after transduction TCR or TCR+FOXP3 transduced cells were injected into HLA-DRB*0401 transgenic hosts conditioned with 4 Gy irradiation. 7 weeks later flow cytometry was used to determine the engraftment of transduced Treg FIG. 15, A shows the transduction efficiency determined through expression of human variable 2.1 and murine Foxp3 on d1 post-transduction. FIG. 15, B shows splenocytes from mice that received Treg transduced with TCR or TCR+FOXP3 stained with Thy1.1 to identify transferred cells (top panel) and FOXP3 and TCR (bottom panel). FIG. 15, C shows cumulative data showing fold change in transduction efficiency (left panel) and fold change in absolute number of transduced cells (right panel) relative to day of injection for Treg transduced with TCR or TCR+FOXP3. FIG. 15, D shows a representative expression of FOXP3 within transduced cells 7 weeks after transfer. Graphs show cumulative of percentage FOXP3+ cells within the transduced population at week 7 (left) and the fold change in FOXP3+ cells relative to the day of injection.

Example 16B—Treg Expressing Exogenous FOXP3 Retain Treg Functionality after 7 Weeks In Vivo Whilst Tregs not Expressing Exogenous FOXP3 Acquire the Ability to Produce Effector Cytokines Splenocytes were cultured for 4 hours with CD86+HLA-DR4+CHO cells pulsed with irrelevant peptide or 10 uM MBP. Treg expressing exogenous FOXP3 retain Treg functionality after 7 weeks in vivo as demonstrated by lack of effector cytokine production, whilst Tregs not expressing exogenous FOXP3 acquire the ability to produce effector cytokines (FIG. 16).

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cellular immunology or related fields are intended to be within the scope of the following claims.

The invention claimed is:

1. An engineered Treg comprising a T cell receptor (TCR), wherein the TCR comprises an α chain and a β chain, wherein the α chain of the TCR comprises three CDRs having the following amino acid sequences:

```
CDR1α-
                              (SEQ ID NO: 3)
TISGTDY

CDR2α-
                              (SEQ ID NO: 4)
GLTSN

CDR3α-
                              (SEQ ID NO: 1)
TVYGGATNKLI;
``` and wherein the β chain of the TCR comprises three CDRs having the following amino acid sequences:

```
CDR1β-
                              (SEQ ID NO: 5)
DFQATT

CDR2β-
                              (SEQ ID NO: 6)
SNEGSKA

CDR3β-
                              (SEQ ID NO: 2)
SARGGSYNSPLH,
``` wherein the α chain of the TCR comprises a human constant region amino acid sequence having at least 95% sequence identity to SEQ ID NO: 26 and/or the β chain of the TCR comprises a human constant region amino acid sequence having at least 95% sequence identity to SEQ ID NO: 27.

2. An engineered Treg according to claim 1, wherein:
(a) the variable region of the α chain of the TCR comprises an amino acid sequence having at least 80% sequence identity to SEQ ID NO: 7; and
(b) the variable region of the β chain of the TCR comprises an amino acid sequence having at least 80% sequence identity to SEQ ID NO: 8.

3. An engineered Treg according to claim 1, wherein the β chain of the TCR comprises a human constant region amino acid sequence which comprises a cysteine residue at the position corresponding to position 22 as shown in SEQ ID NO: 27.

4. An engineered Treg according to claim 1, wherein the constant region domains of the α chain and β chain of the TCR each comprise an additional cysteine residue that enables the formation of an extra disulphide bond between the α chain and the β chain.

5. An engineered Treg according to claim 1, wherein:
(a) the α chain of the TCR comprises an amino acid sequence having at least 80% sequence identity to SEQ ID NO: 9; and
(b) the β chain of the TCR comprises an amino acid sequence having at least 80% sequence identity to SEQ ID NO: 10.

6. An engineered Treg according to claim 1, wherein the Treg is derived from a T cell isolated from a subject.

7. A pharmaceutical composition comprising an engineered Treg according to claim 1.

8. A method for treating multiple sclerosis in an HLADRB1*0401 subject which comprises the step of administering an engineered Treg according to claim 1 to the subject.

* * * * *